US010287313B2

(12) United States Patent
Damha et al.

(10) Patent No.: US 10,287,313 B2
(45) Date of Patent: May 14, 2019

(54) RNA MONOMERS CONTAINING 0-ACETAL LEVULINYL ESTER GROUPS AND THEIR USE IN RNA MICROARRAYS

(71) Applicants: THE ROYAL INSTITUTION FOR THE ADVANCEMENT OF LEARNING/MCGILL UNIVERSITY, Montreal (CA); WISCONSIN ALUMNI RESEARCH FOUNDATION, Madison, WI (US); Saima Akhtar, Niskayuna, NY (US)

(72) Inventors: Masad Damha, St-Hubert (CA); Jeremy Lackey, Montreal (CA); Debbie Mitra, Ottawa (CA); Marvin Wickens, Madison, WI (US); Franco Cerrina, Madison, WI (US); Mark Somoza, Weidling (AT)

(73) Assignees: The Royal Institution for the Advancement of Learning/McGill University, Montreal (CA); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/983,504

(22) Filed: Dec. 29, 2015

(65) Prior Publication Data
US 2016/0340382 A1 Nov. 24, 2016

Related U.S. Application Data

(63) Continuation of application No. 13/061,022, filed as application No. PCT/CA2009/001244 on Sep. 4, 2009, now Pat. No. 9,249,175.

(60) Provisional application No. 61/094,525, filed on Sep. 5, 2008, provisional application No. 61/181,562, filed on May 27, 2009.

(51) Int. Cl.
| | |
|---|---|
| *C07H 21/02* | (2006.01) |
| *C12Q 1/68* | (2018.01) |
| *C07H 19/067* | (2006.01) |
| *C07H 19/167* | (2006.01) |
| *C12Q 1/6806* | (2018.01) |
| *C12Q 1/6837* | (2018.01) |

(52) U.S. Cl.
CPC .......... *C07H 21/02* (2013.01); *C07H 19/067* (2013.01); *C07H 19/167* (2013.01); *C12Q 1/6806* (2013.01); *C12Q 1/6837* (2013.01); *Y02P 20/55* (2015.11)

(58) Field of Classification Search
CPC .... C07H 21/02; C07H 19/067; C07H 19/167; C12Q 1/6806; C12Q 1/6837; Y02P 20/55
See application file for complete search history.

(56) References Cited

U.S. PATENT DOCUMENTS 6,503,711 B1 * 1/2003 Krull .................... C12Q 1/6825
250/458.1

FOREIGN PATENT DOCUMENTS

CN 101104954 A 1/2008

OTHER PUBLICATIONS

Ramsay, "DNA chips: State-of-the art", Nature Biotechnology 1998, 16:40-44.
Reese, "Oligo- and poly-nucleotides: 50 years of chemical synthesis", Org. Biomol. Chem. 2005, 3:3851-3868.
Pitsch et al., "Fast and Reliable Automated Synthesis of RNA and Partially 2'-O-Protected Precursors ('Caged RNA') Based on Two Novel, Orthogonal 2'-O-Protecting Groups", Helv. Chim. Acta 1999, 82: 1753-1761.
Iwai et al., "5'-Levulinyl and 2'-tetrahydrofuranyl protection for the synthesis of oligoribonucleotides by the phosphoramidite approach" Nucleic Acids Res. 1988, 16:9443-9456.
Manoharan, "RNA interference and chemically modified small interfering RNAs" Curr. Opin. Chem. Biol. 2004, 8:570-579.
Beaucage, "Solid-phase synthesis of siRNA oligonucleotides" Curr. Opin. Drug Discov. Devel. 2008, 11: 203-216.
Damha et al., "An improved procedure for derivatization of controlled-pore glass beads for solid-phase oligonucleotide synthesis", Nucleic Acids Res. 1990, 18:3813-3821.
Hogrefe et al. "Deprotecton of methylphosphonate oligonucleotides using a novel one-pot procedure", Nucleic Acids Res. 1993, 21(9): 2031-2038.
Pon et al., "Hydroquinone-O,O'-diacetic acid ('Q-linker') as a replacement for succinyl and oxalyl linker arms in solid phase oligonucleotide synthesis", Nucleic Acids Res. 1997, 25: 3629-3635.
Moorcroft et al., "In situ oligonucleotide synthesis on poly(dimethylsiloxane): a flexible substrate for microarray fabrication", Nucleic Acids Res. 2005, 33: 1-10.

(Continued)

*Primary Examiner* — Sarah Pihonak
*Assistant Examiner* — Jason Deck
(74) *Attorney, Agent, or Firm* — Harvest IP Law LLP

(57) ABSTRACT

The present invention is directed to RNA monomers comprising O-acetal levulinyl protecting groups at the 2' and/or the 5'-hydroxy functionalities of the ribose moiety. Said monomers may be incorporated into oligoribonucleotides or RNA polynucleotides. Furthermore, the invention is directed to methods for the synthesis of said RNA monomers, oligoribonucleotides and RNA polynucleotides, as well as methods for their deprotection and methods for the use of said compounds and compositions comprising said compounds. In particular, such compounds and compositions comprising them are used in methods for light-directed synthesis of RNA microarrays.

4 Claims, 17 Drawing Sheets
Specification includes a Sequence Listing.

(56) References Cited

OTHER PUBLICATIONS

Phillips et al., "In situ oligonucleotide synthesis on carbon materials: stable substrates for microarray fabrication", Nucleic Acids Res. 2008, 36: 1-9.
Warren et al., "Defining the sequence-recognition profile of DNA-binding molecules", Proc. Nat. Acad. Sci. USA 2006, 103: 867-872.
Gao et al., "A flexible light-directed DNA chip synthesis gated by deprotection using solution photogenerated acids", Nucleic Acids Res, 2001, 29: 4744-4750.
Hughes et al., "Expression profiling using microarrays fabricated by an ink-jet oligonucleotide synthesizer", Nature Biotech. 2001, 19:342-347.
Singh-Gasson et al., "Maskless fabrication of light-directed oligonucleotide microarrays using a digital micromirror array", Nature Biotechnology 1999, 17: 974-978.
Puckett et al., "Quantitative Microarray Profiling of DNA-Binding Molecules", J. Am. Chem. Soc. 2007, 129, 12310-12319.
Rastogi et al., "A new 2'-hydroxyl protecting group for the automated synthesis of oligoribonucleotides", Nucleic Acids Res. 1995, 23, 4872-4877.
Lackey et al., "Solid-Phase Synthesis and On-Column Deprotection of RNA from 2'- (and 3'-) O-Levulinated (Lv) Ribonucleoside Monomers" Org. Lett. 2007, 9, 789-792.
Happ, et al., "New Approach to the Synthesis of 2'(3')-O-Aminoacyl Oligoribonucleotides'" J. Org. Chem. 1987, 52, 5387-5391.
Heikkila, et al., "The 9-Fluorenylmethoxycarbonyl (Fmoc) Group for the Protection of Amino Functions of Cytidine, Adenosine, Guanosine and Their 2'-Deoxysugar Derivatives", Acta. Chem. Scan. Ser. B. 1983, B37, 263-265.
Markiewicz, "Tetraisopropyldisiloxane-1,3-diyl, a Group for Simultaneous Protection of 3'- and 5'-Hydroxy Functions of Nucleosides" J. Chem. Res. (S) 1979, 24-25.
Semenyuk et al., "Synthesis of RNA Using 2'-O-DMT Protection" J. Am. Chem. Soc. 2006, 128, 12356-12357.
Kelemen et al., "Hypersensitive substrate for ribonucleases", Nucleic Acids Res. 1999, 27, 3696-3701.
Ogilvie et al., "The Use of Silyl Groups in Protecting the Hydroxyl Functions of Ribonucleosides", Tetrahedron Lett. 1974, 15: 2861-2867.
Garcia et al., "Novel enzymatic synthesis of levulinyl protected nucleosides useful for solution phase synthesis of oligonucleotides", Tetrahedron Asymmetry 2003, 14: 3533-3540.
Zavgorodny et al., "1-Alkylthioalkylation of Nucleoside Hydroxyl Functions and Its Synthetic Applications: A New Versatile Method in Nucleoside Chemistry",Tetrahedron Lett. 1991, 32, 7593-7596.
Parley et al., "First Evaluation of Acyloxymethyl or Acylthiomethyl Groups as Biolabile 2'-O-Protections of RNA", Org. Lett. 2006, 8, 3869-3872.
Markiewicz, "Tetraisopropyldisiloxane-1,3-diyl, a Group for Simultaneous Protection of 3'- and 5'-Hydroxy Functions of Nucleosides", J. Chem. Res. (M) 1979, 181-197.
Ogilvie, et al., "N-Levulination of Nucleosides", Tetrahedron Lett. 1982, 23, 2615-2618.
Hagen et al., "Synthesis of 2'(3')-O-(Aminoacyl) Trinucleotides Incorporating All Four Common Bases", J. Org. Chem. 1988, 53, 5040-5045.
Co-Pending Chinese Patent Application 200980144324.X, a National Phase Application Based on PCT/CA2009/001244, First Office Action (English Translation), dated Jan. 24, 2014.
English Abstract of Chinese Patent Application Publication CN101104954A, Publication Date Jan. 16, 2008 (Cited as Reference #3 in the First Office Action of Co-Pending Chinese Patent Application 200980144324.X, which is a National Phase Application Based on PCT/CA2009/001244).
Wu et al., Molecular Genetics and Genetic Engineering, Henan Medical University Press, Dec. 12, 1997, pp. 164-165 (Cited as Reference #4 in the First Office Action of Co-Pending Chinese Patent Application 200980144324.X, which is a National Phase Application Based on PCT/CA2009/001244), (English Translation not available).
Co-Pending Chinese Patent Application 200980144324.X, Second Office Action (English Translation), dated Dec. 12, 2014.

* cited by examiner

FIG. 4A

| Amidite | Synthesis | Deprotection | |
|---|---|---|---|
| 2'-TBS, B=U; A^Bz; C^Bz; G^ibu | - 0.1M amidite<br>- 1 min coupling<br>- DCI activator | 1) 3:1 EtOH/NH$_4$O<br>(16hr, 55 °C)<br>2) 1 M TBAF<br>(24 hr, r.t.) | |
| 2'-TOM, B=U; A^Ac; C^Ac; G^Ac | - 0.1M amidite<br>- 1 min coupling<br>- DCI activator | 1) 3:1 EtOH/NH$_4$O<br>(16hr, 55 °C)<br>2) 1 M TBAF<br>(24 hr, r.t.) | |
| 2'-ALE, B=U; A^Lv; C^Lv; G^dmf | - 0.1M amidite<br>- 1 min coupling<br>- DCI activator | ALE On-line<br>1) 2:3 TEA/MeCN<br>2) 0.5 M H.H.<br>3:2 pyr/HOAc, 1hr<br>3) 1M TBAF (24 hr)<br>ALE Base<br>1) EtOH/NH$_4$OH,<br>1 hr | TOM TBDMS ALE ALE<br>On-line Base |

RNA MONOMERS CONTAINING 0-ACETAL LEVULINYL ESTER GROUPS AND THEIR USE IN RNA MICROARRAYS

RELATED APPLICATIONS

This application is a continuation application to U.S. application Ser. No. 13/061,022, filed on Sep. 30, 2011, now U.S. Pat. No. 9,249,175, which is a National Stage Application of PCT/CA2009/001244, filed on Sep. 4, 2009, which in turn claims priority to U.S. Provisional Patent Application No. 61/094,525 filed on Sep. 5, 2008 and U.S. Provisional Patent Application No. 61/181,562 filed on May 27, 2009; all of which are herein incorporated by reference.

GOVERNMENT INTERESTS

This invention was made with United States government support under grant No. HG002375 awarded by the NIH. The United States government has certain rights in this invention.

FIELD OF THE INVENTION

The present invention provides arrays of immobilized oligonucleotide probes for analyzing molecular interactions of biological interest, and therefore relates to diverse fields impacted by the nature of molecular interaction, including chemistry, biology, medicine, and medical diagnostics.

BACKGROUND

Microarray technology is readily used in biological research as it provides unprecedented information on nucleic acids in a wide range of applications such as gene expression and genotyping (Ramsay, 1998, Nature Biotechnology 16: 40-44; U.S. Pat. No. 5,837,832). Like DNA, RNA microarrays have also emerged as combinatorial tools as a result of the increasing interest in the use of RNAi and RNA aptamers. The fabrication of such microarrays has evolved from spotting cDNA onto filter paper to more advanced methods such as photolithography with masks or micromirror arrays. While microarrays may be fabricated through immobilization or spotting of pre-synthesized oligonucleotides, the in situ synthesis of DNA microarrays has become the preferred technique as it provides unparalleled chip complexity in an efficient and cost effective manner. However, unlike DNA, the construction of RNA microarrays is limited to spotting as they are far more challenging to synthesize in situ. In addition RNA is more susceptible to enzymatic and chemical hydrolysis.

In general, unlike DNA, there are challenges associated with synthesizing RNA oligonucleotides as a result of the distinct 2'-hydroxyl group present in RNA. The 2'-hydroxyl must be appropriately protected in order to prevent phosphodiester bond isomerization or degradation and to allow for efficient monomer coupling during oligonucleotide synthesis (Reese, 2005, Org. Biomol. Chem. 3: 3851-3868). To date, there have been many attempts to design protecting groups that embody the conditions required for the construction of high quality oligoribonucleotides. The most widely used 2'-protecting group is the 2'-O-t-butyldimethylsilyl (TBDMS) group, introduced in the oligonucleotide area by Ogilvie et al., 1974, Tetrahedron Lett. 15: 2861-2867. This protecting group is removed at the end of RNA chain assembly by fluoride ions. Other silyl protecting groups such as 2'-O-TOM (2'-O-triisopropylsilyloxymethyl) have been used in the synthesis of RNA (Pitsch et al., 1999, Helv. Chim. Acta 82: 1753-1761). Alternate protecting groups are the photolabile group 2'-(2-nitrophenyl)ethoxycarbonyl, 2'-(2-nitrophenyl)ethylsulfonyl and 2'O—(O-nitrobenzyl) substituents and the acid labile acetals such as the 2'-tetrahydropyranyl, 2'-O-Fpmp (1-(2-fluorophenyl)-4-methoxypiperidin-4-yl), 2'-O-Cpep (1-(4-chlorophenyl)-4-ethoxypiperidin-4-yl), 2'-O-4-MABOM (2'-O-[4-(N-methylamino)benzyloxy]methyl, and 2'-ACE (2'-O-bis(2-acetoxyethoxy)methyl). Synthesis of 3'- and 5'-O-levulinyl-2'-deoxy- and 2'-O-alkylribonucleosides has been described by Javier et al., 2003, Tetrahedron 14: 3533-3540. The levulinyl group has been employed for protection of the 5'-hydroxyl group in the synthesis of oligoribonucleotides by the phosphoramidite approach (Iwai and Ohtsuka, 1988, Nucleic Acids Res. 16: 9443-9456). In all cases the synthesis of oligoribonucleotides is an elaborate multistep process, which entails assembly of the oligonucleotide chain, deprotection of the base labile nucleobase protecting groups, cleavage from the support, followed by removal of the 2'-hydroxyl protecting group.

At present there is a dearth of reports on the fabrication of RNA microarrays in the literature. Generally RNA microarrays are synthesized through immobilization of a pre-synthesized RNA strand in its native form, which requires expensive synthesis and purification of modified RNA (i.e., thiol, biotin or amino terminated end), which subsequently limit chip complexity. In addition, such methods leave RNA oligonucleotides vulnerable to RNA degradation as they are in the deprotected form. An alternative strategy uses surface RNA-DNA ligation chemistry to create RNA microarrays from 5T-phosphate modified DNA microarrays. This strategy involves expensive and elaborate procedures that are limited by reliability and complexity. There are no examples in the literature of an in situ synthesis of RNA microarrays.

RNA interference (RNAi) therapeutics represents a fundamentally new way to treat human diseases (Manoharan, 2004, Curr. Opin. Chem. Biol. 8: 570-579). However, achieving targeted tissue and cellular delivery, stabilization in vivo, and cost effective large scale synthesis of RNA are significant bottlenecks in the development of RNAi technology.

There is a need to develop synthetic strategies that permits both the growth and deprotection of RNA chains that remain attached to a solid polymer support or to a glass or chip surface. The present invention addresses these and related needs.

BRIEF SUMMARY

Provided are RNA monomers and protecting groups that can be used with these monomers. In particular, a novel 2'-O-acetal levulinyl ester (also referred to herein as ALE, or 2'-ALE) protecting groups for the 2'-hydroxyl group of ribonucleosides are provided.

In general, the methods of the present invention involve forming and/or providing a synthetic RNA molecule, where the RNA molecule has at least two protecting groups, and where at least one of the protecting groups is a 2'-O-ALE protecting group. The synthetic RNA molecules may include additional protecting groups, including: a nucleobase having a protecting group, a 2'-hydroxyl protecting group, a phosphorus protecting group, and combinations thereof. In preferred embodiments of this invention, the RNA monomers have two or more protecting groups. One or more of the protecting groups can be deprotected through interaction with light. In particular, useful for the practice of the invention are ribonucleotides containing photolabile 5'-2-(2-nitrophenyl)propoxycarbonyl (NPPOC) and base labile 2'-O-acetal-levulinyl ester (ALE) protecting groups.

The RNA monomers and protecting groups of the present invention can be used for in situ synthesis of RNA molecules on solid substrate. Also provided are compositions and methods for a maskless light-directed in situ synthesis of RNA microarrays. In preferred embodiments, deprotection of the RNA strands takes place while the oligomers are attached to the solid substrate, for example to the microarray surface. Various applications for these RNA microarrays are provided.

BRIEF DESCRIPTION OF THE DRAWINGS

FIG. 4A shows 24% denaturing (8.3 M Urea) PAGE analysis.

FIG. 8B shows a graphical representation of the coupling time for rU phosphoramidite 14a.

DETAILED DESCRIPTION OF THE PRESENTLY PREFERRED EMBODIMENTS

Figure 1:
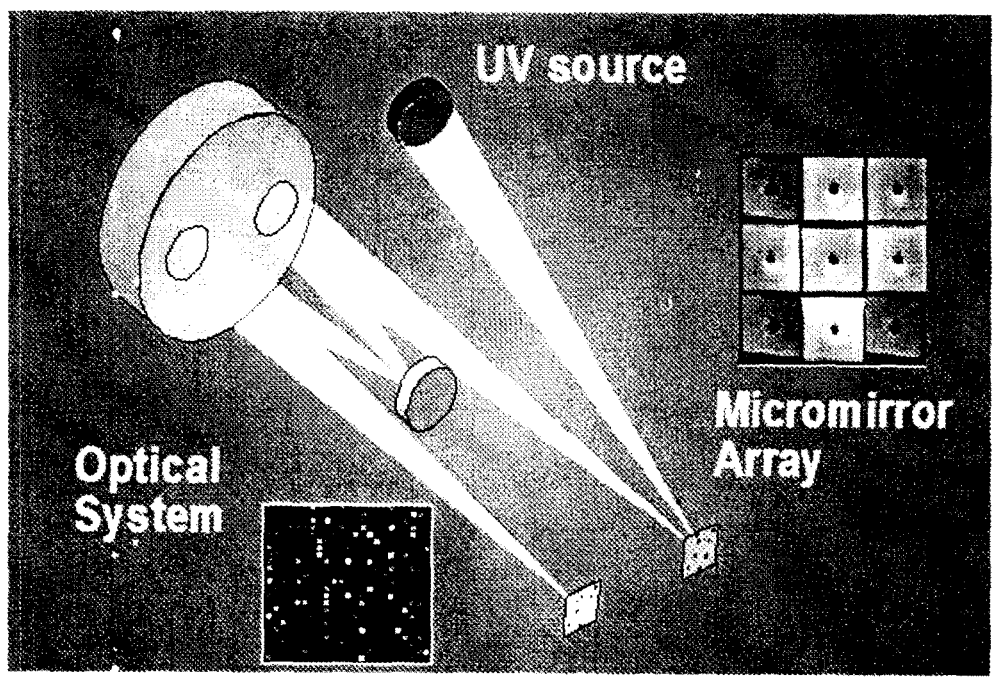
FIG. 1 illustrates the schematics of light-directed synthesis of RNA microarrays using a maskless array synthesizer (MAS).

This invention relates generally to the field of biology, and particularly to techniques for the analysis of nucleic acids using arrays. The present invention provides compositions and methods for the synthesis of RNA in situ, on solid substrates. In some embodiments, the present invention provides novel compositions and methods for the synthesis of arrays of oligoribonucleotide probes in the form of RNA (micro)arrays, or RNA chips.

Generally, the nomenclature and the laboratory procedures described below are those well known and commonly employed in the art. Standard techniques are used for DNA and RNA isolation, purification, amplification, and cloning. Enzymatic reactions involving DNA ligase, DNA polymerase, restriction endonucleases, and the like are generally performed according to the manufacturer's specifications. These techniques and various other techniques are generally performed according to Sambrook et al., 1989, Molecular Cloning—A Laboratory Manual, Cold Spring Harbor Laboratory Press, Cold Spring Harbor, N.Y.; Ausubel et al., 1993, Current Protocols in Molecular Biology, Volumes 1-3, John Wiley & Sons, Inc., New York, N.Y.; and Kriegler, 1990, Gene Transfer and Expression: A Laboratory Manual, Stockton Press, New York, N.Y., each of which is incorporated herein by reference in its entirety. The importance of RNA, RNA control, and RNA interactions in general, are disclosed in Gesteland et al., 2006, The RNA World, $3^{rd}$ ed., Cold Spring Harbor Laboratory Press, Cold Spring Harbor, N.Y.; and in Sonenberg et al., 2000, Translational Control of Gene Expression, Cold Spring Harbor Laboratory Press, Cold Spring Harbor, N.Y., both of which are incorporated herein by reference.

Various aspects related to the practice of the present invention are disclosed in U.S. Pat. No. 5,672,695 ("Modified ribozymes"); U.S. Pat. Nos. 5,861,501 and 6,111,095 ("Capped synthetic RNA, analogs, and aptamers"); U.S. Pat. No. 6,222,030 B1 ("Solid phase synthesis of oligonucleotides using carbonate protecting groups and alpha-effect nucleophile deprotection"); U.S. Pat. No. 6,295,153 B1 ("Method and apparatus for synthesis of arrays of DNA probes"); U.S. Pat. No. 6,426,184 B1 ("Method and apparatus for chemical and biochemical reactions using photogenerated reagents"); and in U.S. Patent Application Publication No. US 2007/0100136 A1 ("Monomer compositions for the synthesis of RNA, methods of synthesis, and methods of deprotection"); all of which are incorporated herein by reference. Recent advances in RNA synthesis have been summarized in a review by Beaucage, 2008, Curr. Opin. Drug Discov. Devel. 11: 203-261.

A "nucleotide" and a "nucleotide moiety" refer to a sub-unit of a nucleic acid (RNA, DNA, or an analogue thereof) which may include, but is not limited to, a phosphate group, a sugar group and a nitrogen containing base, as well as analogs of such sub-units. Other groups (e.g., protecting groups) can be attached to the sugar group and nitrogen-containing base group. A "ribonucleotide" is any of various nucleotides in which the carbohydrate component is ribose. A ribonucleotide is a structural unit of RNA.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangeable in most instances. One skilled in the art would have the understanding that additional modification to the nucleoside may be necessary.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to, collectively, as "purine and pyrimidine bases and analogs thereof"). Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as levulinyl, acetyl, difluoroacetyl, trifluoroacetyl, isobutyryl, benzoyl, 9-fluorenylmethoxycarbonyl, phenoxyacetyl, dimethylformamidine, $N_1N$-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-rrethyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

A "nucleotide monomer" refers to a molecule which is not incorporated in a larger oligo- or poly-nucleotide chain and which corresponds to a single nucleotide sub-unit. Nucleotide monomers may also have activating or protecting groups, if such groups are necessary for the intended use of the nucleotide monomer. An "RNA monomer" is a nucleotide monomer in which the carbohydrate component is ribose.

An "oligonucleotide", "oligomer", or "oligo" generally refers to a nucleotide multimer of about 2 to 100 nucleotides in length, while a "polynucleotide" includes a nucleotide multimer having any number of nucleotides greater than 1. The terms "oligonucleotide" and "polynucleotide" are often used interchangeably, consistent with the context of the sentence and paragraph in which they are used in. An "oligoribonucleotide" or an "RNA oligonucleotide" is an oligonucleotide consisting of ribonucleotides. An "RNA polynucleotide" is a polynucleotide consisting of ribonucleotides.

A "polynucleotide intermediate" is a molecule occurring between steps in chemical synthesis of a polynucleotide, where the polynucleotide intermediate is subjected to further reactions to get the intended final product, for example a protected polynucleotide, which is then deprotected.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom (e.g., a sulfur atom, or the nitrogen atom of a mono- or di-alkyl amino group) or group (e.g., a methyl or other alkyl or functionalized alkyl groups).

A "group" includes both substituted and unsubstituted forms. Typical substituents include one or more lower alkyl, amino, imino, amido, alkylamino, arylamino, alkoxy, aryloxy, thioalkyl, alkylthio, arylthio, aryl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are typically chosen so as not to substantially adversely affect reaction yield (for example, not lower it by more than 20% (or 10%, or 5%, or 1%) of the yield otherwise obtained without a particular substituent or substituent combination). A "phospho" group includes a phosphodiester, phosphotriester, and H-phosphonate groups. In the case of either a phospho or phosphite group, a chemical moiety other than a substituted 5-membered furyl ring may be attached to 0 of the phospho or phosphite group which links between the furyl ring and the P atom.

A "protecting group" is used in the conventional chemical sense to reference a group, which reversibly renders unreactive a functional group under specified conditions of a desired reaction. Some protecting groups are well known to one skilled in the art. Examples of the protection/deprotection process as well as various protecting groups are described in Wuts and Greene, 2006, Greene's Protective Groups in Organic Synthesis, Wiley-Interscience, New York, N.Y. Any suitable protecting group known to one skilled in the art may be used. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "O-protecting group" refers to a protecting group where the protected group is a hydroxyl. In one embodiment, the present invention provides a novel protecting group for the 2'-hydroxyl of ribonucleosides, which is an acetal levulinyl ester (ALE) protecting group. In some embodiments, using the novel protecting group of the present invention in combination with at least one other protecting group, RNA molecules can be synthesized in situ.

In addition to applications in RNA microarray fabrication, the utility of the novel RNA monomers described here can be extended to routine synthesis of RNA on conventional solid supports such as controlled pore glass and polystyrene. In this case, the RNA strand is cleaved and released from the support after synthesis and the resulting synthetic RNA utilized in physicochemical or biological studies. There are several derivatives that may be included for such applications (see structures 1 to 4 below). The 2'-O-ALE and N-Lv/dmf protecting group combination of the present invention provides unique ribonucleoside 5'-DMTr 3'-phosphoramidite synthons (see general structure 5) for standard RNA synthesis that couple with excellent rates and efficiencies (>99%). Protecting groups in structures 1 through 5 are as follows: (1) 2'-O-TBDMS, B=Ade$^{Bz}$, Cyt$^{Bz}$, Gua$^{ibu}$, Ura; (2) 2'-O-TOM, B=Ade$^{Ac}$, Cyt$^{Ac}$, Gua$^{Ac}$, Ura; (3) 2'-ACE, B=Ade$^{Bz}$, Cyt^, Gua$^{ibu}$, Ura; (4) 2'-Lv, B=Ade$^{Lv}$, Cyt$^{Lv}$, Gua$^{dmf}$, Ura; (5) 2'-O-ALE, B=Ade$^{Lv}$, Cyt$^{Lv}$, Gua$^{dmf}$, Ura.

In addition, the ALE 2'-protecting group strategy provides two distinct advantages over previously reported synthons: (1) it prevents the common 2' to 3'-isomerization that can occur with acyl and silyl protecting groups, and (2) the removal of all protecting groups can be efficiently performed on the solid support, which simplifies post-synthesis deprotection of RNA chains and minimizes the potential for degradation of the oligomers by RNases.

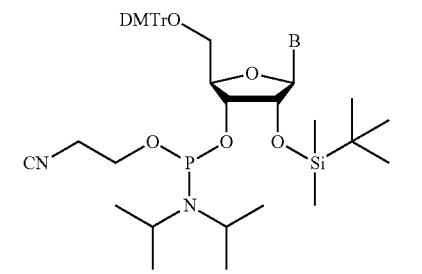

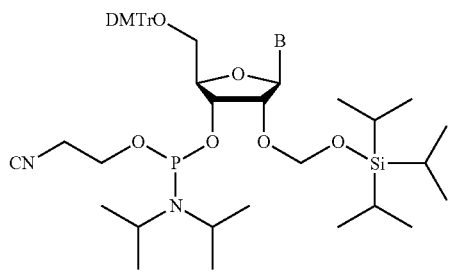

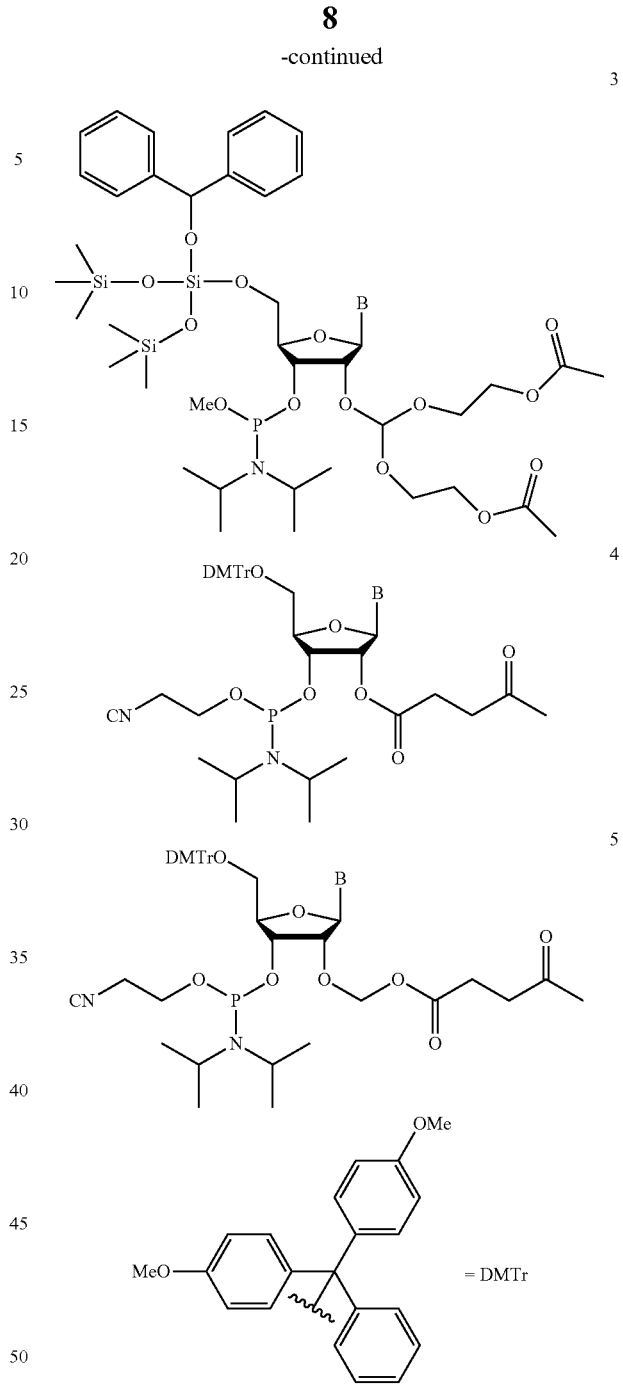

For example, novel 2'-O-ALE (Acetal Levulinyl Ester) phosphoramidite derivatives can be prepared and used in combination with cyanoethyl phosphate protecting groups for the solid-phase synthesis of a chimeric oligonucleotide strand, 5'-rN$_{19}$-dT-3'. The average coupling yield of the phosphoramidite is superior to one obtained with a 2'-TBDMS (1) or 2'-TOM (2) phosphoramidite reagents. Upon completion of the RNA chain assembly, the cyanoethyl phosphate protecting groups can be removed using a solution of triethylamine in acetonitrile (2:3 v/v). The 2'-O-ALE protecting groups of the present invention can be cleaved under hydrazinolysis conditions. Finally, the RNA oligonucleotide can be released from the Q-CPG support when treated with 1 molar tetrabutylammonium fluoride (TBAF) in trihydrofluoride (THF) or with triethylamine and 48% aqueous HF (3:1 v/v, 50° C.). When the latter conditions are used prior to hydrazinolysis, an oligonucleotide with its intact 2'-O-ALE groups is obtained. Alternatively, release of 2'-O-ALE protected RNA can be effected through the use of a light-sensitive linker that connects the RNA to the solid support (e.g., polystyrene or controlled pore glass). The released 2'-O-ALE protected RNA strand can be deprotected under hydrozinolysis conditions. Alternatively, the fully deprotected RNA chain can be obtained by treating the solid support with of triethylamine in acetonitrile (2:3 v/v) to cleave cyanoethyl phosphate protecting groups, followed by removal of all remaining protecting groups by treatment with a solution of concentrated aqueous ammonia and ethanol (3:1 v/v at room temperature) or ethylenediamine and ethanol (1:1 v/v).

This method is readily applicable to the synthesis of oligoribonucleotides with mixed composition (see examples illustrated in FIGS. 4-7).

For example, it was possible to synthesize a 21-mer RNA strand of mixed base composition utilizing the 5'-DMTr 2'-O-ALE RNA monomers (bases are protected with Lv for C and A, and dimethylformamidine for G). The strand is synthesized on a solid support (CPG, controlled pore glass appended with a fluoride sensitive Q-linker, or a light sensitive linker) and deprotected in two different ways. The first deprotection protocol involves subjecting the oligomer to triethylamine in acetonitrile to remove the cyanoethyl protecting groups. Then the 2'-O-ALE and base protecting groups (levulinyl on adenine and cytosine or dimethylformamide on guanine) are simultaneously removed by hydrazinolysis. TBAF treatment then releases the oligomer from the Q-linker derivatized CPG, described in Lackey et al., 2007, Org. Lett. 9: 789-792. The second deprotection protocol involves simply treating the CPG with ethanol/conc. aq. ammonia for 1 h at room temperature or ethylenediamine/ethanol (1:1 v/v) for 2 h at room temperature after the cyanoethyl phosphate group has been removed, and evaporating the resulting solution. These deprotecting protocols can be used in the synthesis of a 21-mer RNA strand containing all four nucleotide residues.

Embodiments of the present invention include methods for deprotecting one or more protecting groups of an RNA molecule. For example, 2'-O-ALE protecting groups can be removed using hydrazine hydrate or concentrated aqueous ammonia/alcohol solutions or ethylenediamine/alcohol solutions. The terms "simultaneous deprotection" or "deprotecting simultaneously" refer to a process which aims at removing different protecting groups in the same process and performed concurrently or substantially concurrently. However, as used herein, this term does not imply that the deprotection of the different protecting groups occur at the same time or with the same rate or same kinetics. The term "two-step deprotection" refers to a deprotection procedure that is performed in two steps, e.g. with a certain time delay between the steps. An example of a two-step deprotection procedure is deprotection of a base protecting moiety followed by photodeprotection of the NPPOC protecting group. It is contemplated that both simultaneous deprotection and a two-step deprotection reaction may be used in the practice of the present invention.

Photodeprotection of the NPPOC protecting group can be performed, for example, with irradiation of an immobilized ribonucleotide monomer at about 6.5 J/cm² with a fluence of approximately 50-150 mW/cm², leading to an exposure time of about 120-140 sec.

Some of the present inventors recently reported the use of the 2'-O-levulinyl (Lv) for the 2'-hydroxyl protection of ribonucleoside phosphoramidites (Lackey et al., 2007, Org. Lett. 9: 789-792). The 2'-O-Lv group could be removed on-column and the fully deprotected RNA could be subsequently released from a Q-CPG support when treated with 1 M TBAF in THF. In addition, oligouridylic acid could be released from the solid support with its 2'-O-Lv esters intact. These 2'-O-Lv RNAs showed greater stability in fetal bovine serum compared to the fully deblocked 21-mer. However, synthesis of the phosphoramidite monomer building blocks was low yielding due to difficult separation of 2' and 3'-Lv phosphoramidite regioisomers. The present invention solves this problem while retaining the advantages of the Lv group through the design of a novel acetal levulinyl ester (ALE) protecting group for the 2'-hydroxyl of ribonucleosides.

In various examples of the compositions and methods of the present invention, the schemes illustrating the synthesis of a variety of 2'-O-ALE phosphoramidites are shown below. In one example, this novel 2'-O-ALE rU phosphoramidite has been used for the solid-phase synthesis of a chimeric oligonucleotide strand, 5'-rU$_{11}$-dt-3' (see Scheme 5 below), and for the synthesis of a 12-mer chimeric strand (5'-rU11-dT-3').

In one embodiment of the present invention, a compound of formula (I) is provided:

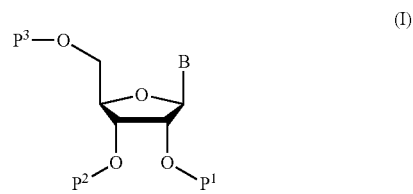

In the compound of formula (I), B is selected from the group consisting of a base and a base including a protecting group; $P^1$ is hydrogen or a protecting group;

$P^2$ is hydrogen or

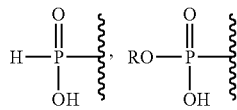

or salts thereof,
or

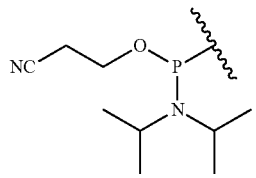

wherein R is methyl, 2-cyanoethyl, 2-chlorophenyl, 4-chlorophenyl;

$P^3$ is hydrogen or a protecting group.

Preferably, at least one protecting group is —CH$_2$OC(O)CH$_2$CH$_2$C(O)CH$_3$, also referred to as "2'-O-acetal levulinyl ester", "2'-O-ALE", "2'-acetal levulinyl ester", "2'-ALE", "acetal levulinyl", or "ALE". The ALE group is stable to acid, fluoride, mild base and photolysis. The ALE group can be removed with hydrazine, aqueous ammonia or ethylenediamine in alcohol.

P¹ and P³ are oxygen protecting groups. Preferably, the P¹ and P³ protecting groups are removable via different reaction conditions such that each may be removed independently without removing the other. In other words, P³, for example, may be selectively removed while P¹ remains in place. In this way, the RNA chain may be synthesized by reacting at the O-5 oxygen while the O-2 oxygen remains protected.

Examples of O-protecting groups include, but are not limited to:

(A) base labile groups including —CH$_2$OC(O)CH$_2$CH$_2$-C(O)CH$_3$ (acetal levulinyl, ALE), —C(O)CH$_2$CH$_2$C(O)CH$_3$ (levulinyl, Lv);

(B) acid labile groups including acetal groups (ACE), 1-(2-fluorophenyl)-4-methoxypiperidin-4-yl (Fpmp), 1-(4-chlorophenyl)-4-ethoxypiperidin-4-yl (Cpep), 4-(N-dichloroacetyl-N-methylamino)benzyloxymethyl (4-MABOM), trityl ether groups including dimethoxytrityl (DMTr) and monomethoxytrityl (MMTr);

(C) reduction labile groups including 2-tert-butyldithiomethyl (DTM), allyl;

(D) fluoride labile group groups including tert-butyldimethylsilane (TBDMS), 2'-O-triisopropylsilyloxymethyl (2'-O-TOM), cyanoethylmethyl (CEM), and 2-(4-tolylsulfonyl)ethoxymethyl (TEM);

(E) photolabile groups including silyl ether groups, nitrobenzyl groups (including 2'-nitrobenzyl groups such as 2-(2-nitrophenyl)propoxycarbonyl (NPPOC), σ-methylnitorpiperonyloxycarbonyl (MeNPOC) and derivatives therein (including thioxanthone-nitrobenzyl group conjugates) and DMBOC (5'-O-dimethoxybenzoincarbonate group); and (F) other protecting groups suitable for use in solid phase synthesis of RNA.

Preferably P¹ is a base labile group or an acid labile group.

In the compound of formula (I), B is a base or a protected-base. The base is preferably a purine or pyrimidine base or analog thereof. Analogs include diaminopurine and its derivatives, inosine and its derivatives, alkylated purines or pyrimidines, acylated purines or pyrimidines, thiolated purines or pyrimidines. More specific analogs include, for example, 1-methyladenine, 2-methyladenine, N6-methyladenine, N6-isopentyladenine, 2-methylthio-N6isopentyladenine, N.N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, and the like. A "protected-base" is protected on at least one nitrogen by any suitable N-protecting group including levulinyl, acetyl, difluoroacetyl, trifluoroacetyl, isobutyryl, benzoyl, 9-fluorenylmethoxycarbonyl, phenoxyacetyl, dimethylformamidine, N,N-diphenyl carbamate, tert-butylphenoxyacetyl and the like. Preferably, the base is selected such that the compound of formula (I) is a derivative of adenine (A), cytosine (C), guanine (G), or uracil (U).

In the compound of formula (I), P³ may include: (i) Photolabile groups: nitrobenzyl groups, i.e. 2'-nitrobenzyl groups, such as NPPOC (2-(2-nitrophenyl)propoxycarbonyl), MeNPOC (α-methylnitorpiperonyloxycarbonyl), and derivatives therein, including thioxanthone-nitrobenzyl group conjugates. DMBOC (5'-O-dimethoxybenzoincarbonate group); (ii) Acid labile groups: trityl ether groups, i.e. DMTr (dimethoxytrityl), MMTr (monomethoxytrityl); (iii) Fluoride labile groups: Silyl ether groups (solid phase synthesis of RNA).

In the compound of formula (I), P¹ may include: (i) Base labile groups: ALE (acetal levulinyl), Lv (levulinyl); (ii) Acid labile groups: acetal groups (ACE), Fpmp (1-(2-fluorophenyl)-4-methoxypiperidin-4-yl), Cpep (1-(4-chlorophenyl)-4-ethoxypiperidin-4-yl), 4-MABOM (4-(N-dichloroacetyl-N-methylamino)benzyloxymethyl); (iii) Reduction labile groups: DTM (2-tert-butyldithiomethyl), allyl; (iv) Fluoride labile group groups: TBDMS (tert-butyldimethylsilane), TOM (triisopropyloxymethyl), CEM (cyanoethylmethyl), TEM (2-(4-tolylsulfonyl)ethoxymethyl.

Preferably P³ is a base labile or photolabile group, more preferably 2-(2-nitrophenyl)propoxycarbonyl (NPPOC).

In another embodiment of the present invention, a compound of a formula (VI) is provided:

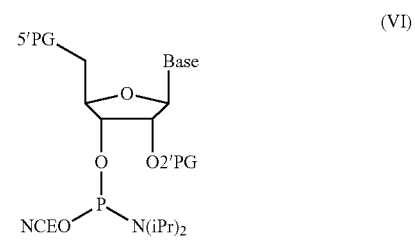

(VI)

This compound is an example of a monomer that can be used in the synthesis of RNA. PG refers to a protecting group.

In the compound of formula (VI), 5'-PG may include: (i) Photolabile groups: nitrobenzyl groups, i.e. 2'-nitrobenzyl groups, such as NPPOC (2-(2-nitrophenyl)propoxycarbonyl), MeNPOC (α-methylnitorpiperonyloxycarbonyl), and derivatives therein, including thioxanthone-nitrobenzyl group conjugates. DMBOC (5'-O-dimethoxybenzoincarbonate group); (ii) Acid labile groups: trityl ether groups, i.e. DMTr (dimethoxytrityl), MMTr (monomethoxytrityl); (iii) Fluoride labile groups: Silyl ether groups (solid phase synthesis of RNA).

In the compound of formula (VI), 2'-PG may include: (i) Base labile groups: ALE (acetal levulinyl), Lv (levulinyl); (ii) Acid labile groups: acetal groups (ACE), Fpmp (1-(2-fluorophenyl)-4-methoxypiperidin-4-yl), Cpep (1-(4-chlorophenyl)-4-ethoxypiperidin-4-yl), 4-MABOM (4-(N-dichloroacetyl-N-methylamino)benzyloxymethyl); (iii) Reduction labile groups: DTM (2-tert-butyldithiomethyl), allyl; (iv) Fluoride labile group groups: TBDMS (tert-butyldimethylsilane), TOM (triisopropyloxymethyl), CEM (cyanoethylmethyl), TEM (2-(4-tolylsulfonyl)ethoxymethyl.

In the compound of formula (VI), preferred monomers contain ALE (acetal levulinyl) as the 2'-PG. The 5'-PG include the photolabile NPPOC (2-(2-nitrophenyl)propoxycarbonyl) group and the acid labile DMTr or MMTr group. Bases are protected with the Lv group (Adenine, Cytosine) or the dmf group (guanine). Uracil requires no base protection.

A "linking moiety" is a group known in the art to connect nucleotide moieties in a polynucleotide or oligonucleotide compound.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. For example the term "alkyl" can refer to straight or branched chain hydrocarbon groups, such as methyl, ethyl, n-propyl, i-propyl, n-butyl, i-butyl, t-butyl, pentyl, hexyl, heptyl, octyl, and the like. Likewise, cycloalkyls have from about 3 to about 10 carbon atoms in their ring structure, and alternatively about 5, 6 or 7 carbons in the ring structure. The term "alkyl" is also defined to include halosubstituted alkyls and heteroatom substituted alkyls. Moreover, the term "alkyl" (or "lower alkyl") includes "substituted alkyls", which refers to alkyl moieties having substituents replacing hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen, thus: R—O—. In this function, R represents the alkyl group. An example would be the methoxy group $CH_3O$—.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." An aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like.

The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocyclyls).

The terms "hemiacetal", "thiohemiacetal", "acetal", and "thioacetal", are recognized in the art, and refer to a chemical moiety in which a single carbon atom is geminally disubstituted with either two oxygen atoms or a combination of an oxygen atom and a sulfur atom. In addition, when using the terms, it is understood that the carbon atom may actually be geminally disubstituted by two carbon atoms, forming ketal, rather than acetal, compounds.

The present invention includes nucleotide monomers and polynucleotide structures (e.g., synthetic ribonucleic acid) including nucleotide moieties, where the nucleotide monomers and nucleotide moieties each include various types of protecting groups. The nucleotide monomers and nucleotide moieties can be used in conjunction with methods, processes, and/or compositions of the present invention, for the deprotection of polynucleotides, and in particular RNA polynucleotides. Embodiments of the present invention enable quantitative or quasi-quantitative and rapid synthesis of the desired deprotected full-length polynucleotide product.

Figure 2:
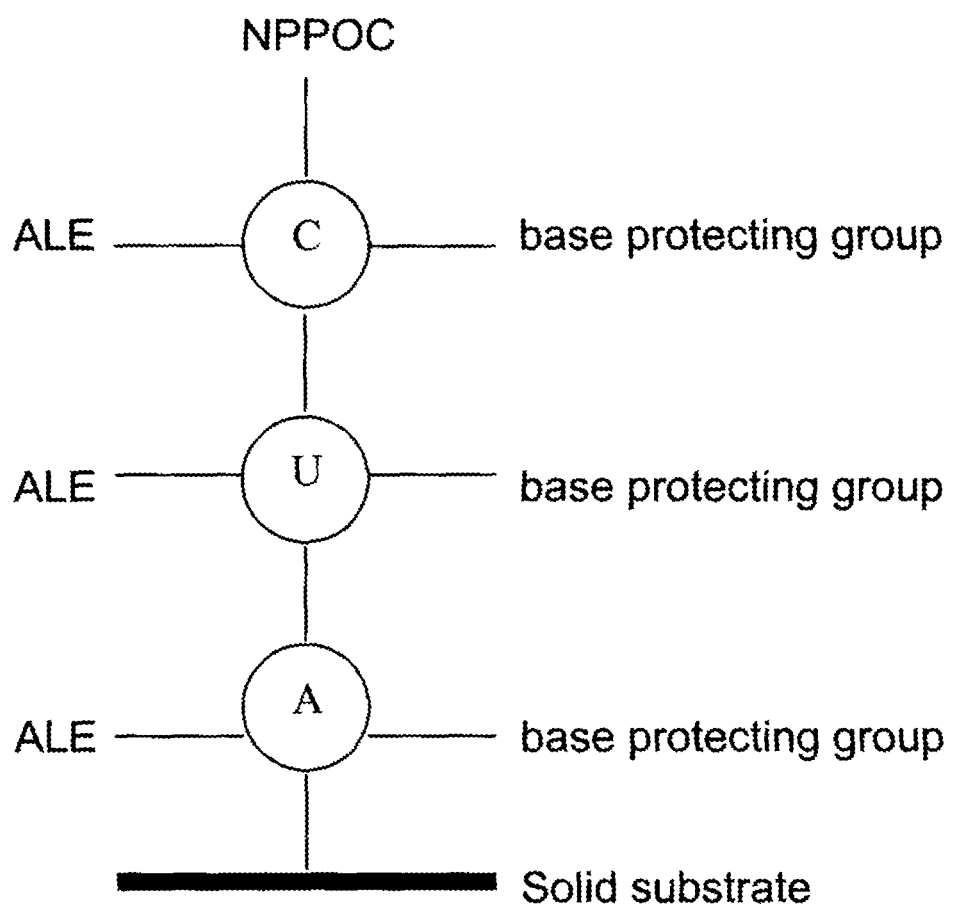
FIG. 2 illustrates one embodiment of the schematics of light-directed synthesis of RNA microarrays, in which a 3-mer oligonucleotide AUC is synthesized in situ on solid substrate.
Figure 3:
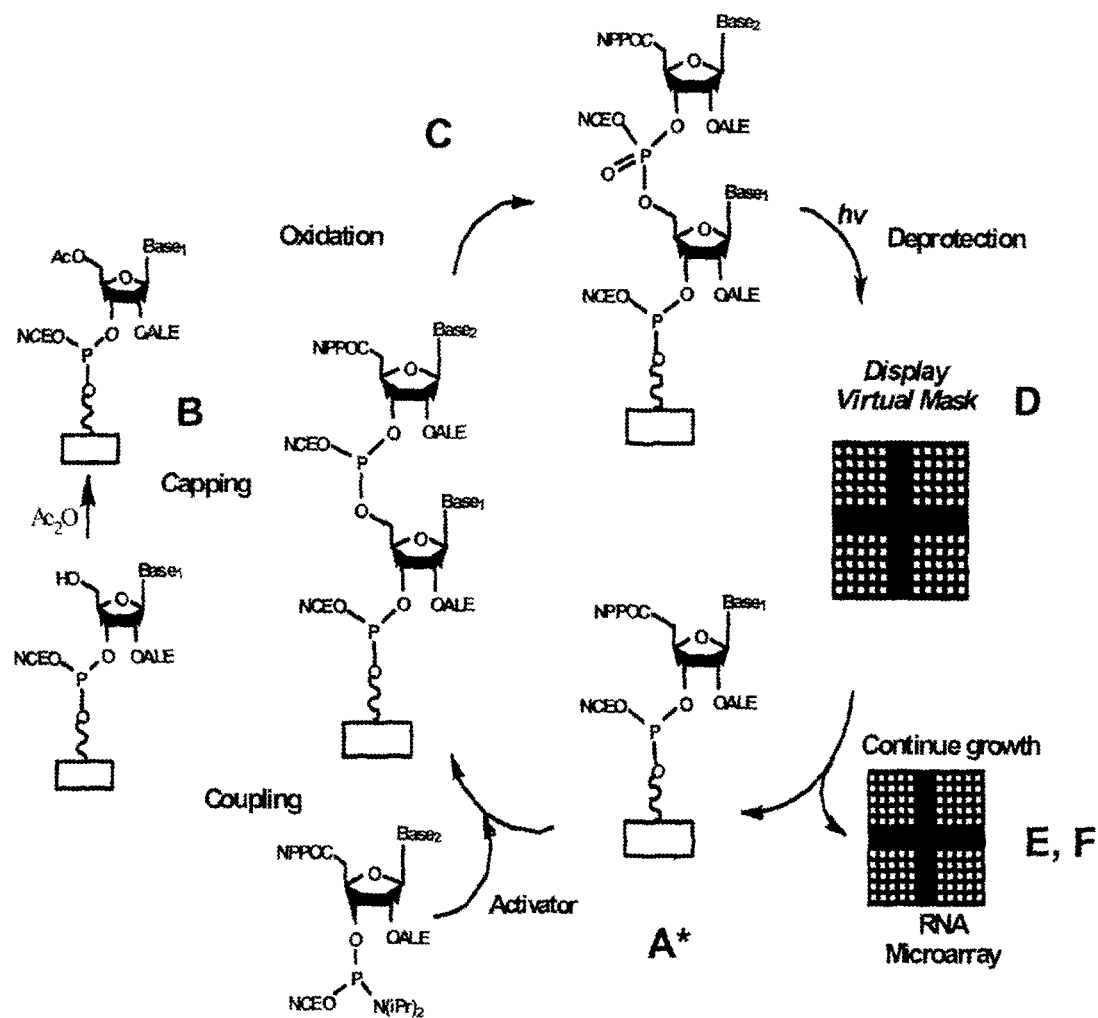
FIG. 3 illustrates another embodiment of the schematics of light-directed synthesis of RNA microarrays: A*, Coupling of first monomer via activator; B, Capping of unreacted 5'OH through acetylation; C, Oxidation of phosphite triester to more stable phosphate; D, Deprotection with light, 365 nm, mask displayed; E, Repetitive n+1 cycles lead to synthesis of oligomers; F, Deprotection of protecting groups under basic conditions.
Figure 4B:
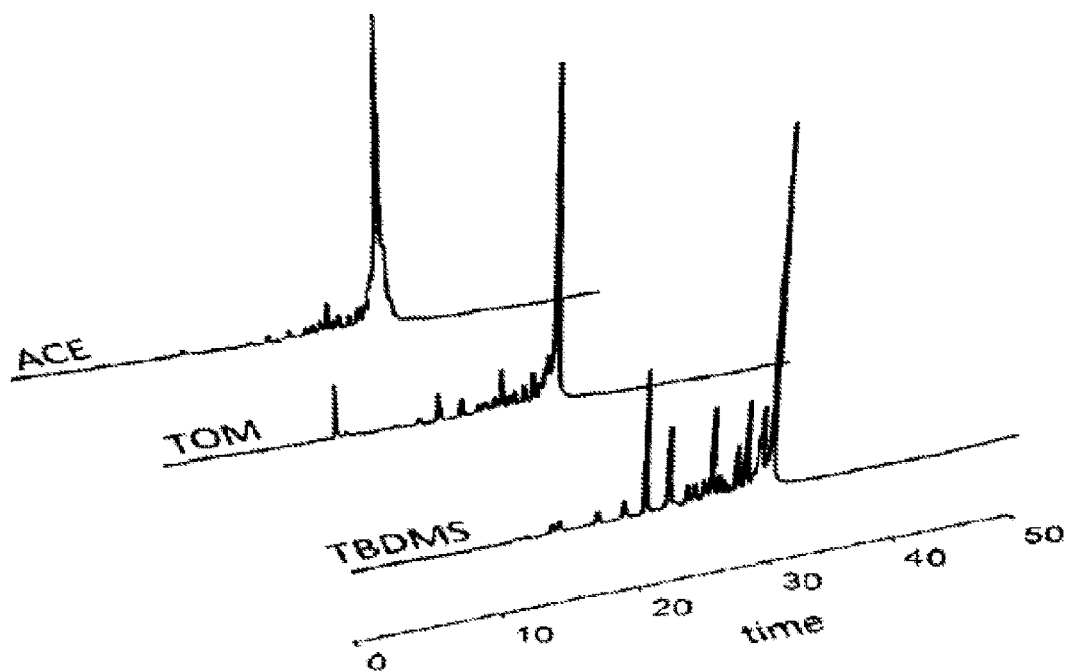
FIG. 4B shows Anion exchange HPLC of crude antisense siRNA strand synthesized using 2'-TOM, 2'-TBDMS and 2'-ALE using 1 min coupling times.

In the initial step of the synthesis, a partially protected ribonucleoside is covalently attached to a solid support to serve as the starting point for oligoribonucleotide synthesis. The ribonucleoside may be bound to the support through its 3'-hydroxyl group or its 5'-hydroxyl group, but is typically bound through the 3'-hydroxyl group. Preferably, the ribonucleoside has at least two protecting groups. Preferably, at least one of the protecting groups is a 2'-O-acetal levulinyl ester (ALE) protecting group; also preferably, for RNA synthesis on microarrays at least one other protecting group is a 5'-2-(2-nitrophenyl)propoxycarbonyl (NPPOC) protecting group; for RNA synthesis on a solid support such a controlled pore glass, polystyrene, polyvinyl or other polymer support used for standard RNA synthesis, the 5'-hydroxyl is preferably protected with the DMTr or MMTr group. Alternatively, the first nucleoside directly attached to the solid support may be bound through either the 2'OH and 3'OH groups since release of the final RNA chain will produce a oligonucleotide strand containing a ribonucleotide (with 2' and 3'OH) groups at its 3' end (Damha et al., 1990, Nucleic Acids Research 18: 3813-3821). A second ribonucleoside monomer is then coupled to the free 5'-hydroxyl group of the support-bound initial monomer, wherein for 3'-to-5' oligoribonucleotide synthesis, the second nucleoside monomer has a 3'-phosphorus containing moiety such as a phosphoramidite group a trityl (MMTr or DMTr) or photolabile protecting group at the 5' position. Alternatively, for 5'-to-3' oligonucleotide synthesis, the second ribonucleoside monomer has a phosphorus moiety at the 5' position and a trityl (MMTr or DMTr) or photolabile, ALE or levulinyl protecting group at the 3' position. This coupling reaction gives rise to a newly formed phosphite triester internucleotide linkage between the initial nucleoside monomer and the added monomer. This generates the dimer rNpN with its sugars and base protecting groups intact. Next, capping (e.g., using acetic anhydride) of any unreacted nucleoside and oxidation (e.g. using iodine, or t-butylperoxide) of the phosphite triester group are performed, to afford the more stable phosphate triester linkage (Damha and Ogilvie, 1993, In "Protocols for Oligonucleotide and Analogs: Synthesis and Properties" S. Agrawal (ed.), Methods in Molecular Biology pp. 81-114, The Humana Press Inc., Totowa, N.J.). Examples of the synthesis of RNA molecules are illustrated in FIGS. 2 and 3.

The synthetic strategy described herein allows for the "on column" deprotection of oligoribonucleotides. A strategy using all four 2'-O-ALE phosphoramidite synthons allows for the assembly and deprotection of desired RNA molecules on solid supports, such as glass or chip surfaces. Oligomers released with their 2'-O-ALE groups intact exhibit an increased stability to nucleases and improved cellular uptake as a consequence of the lipophilic character of their 2'-O-protected sugar moieties. Moreover, in this embodiment each 2'-O-ALE protecting group should be cleaved by intracellular carboxyesterases to generate the native siRNAs inside cells and potentially lead to novel siRNAi prodrugs.

The compositions of the present invention can be generated in a variety of ways. Nonlimiting examples of the synthesis of compositions useful for the practice of this invention are illustrated in the synthesis schemes shown below.

Scheme 1 below illustrates the preferred synthetic method by which 5'-NPPOC-2'-ALE RNA amidites and 5'-DMTr-2'-ALE RNA amidites can be generated.

Scheme 1

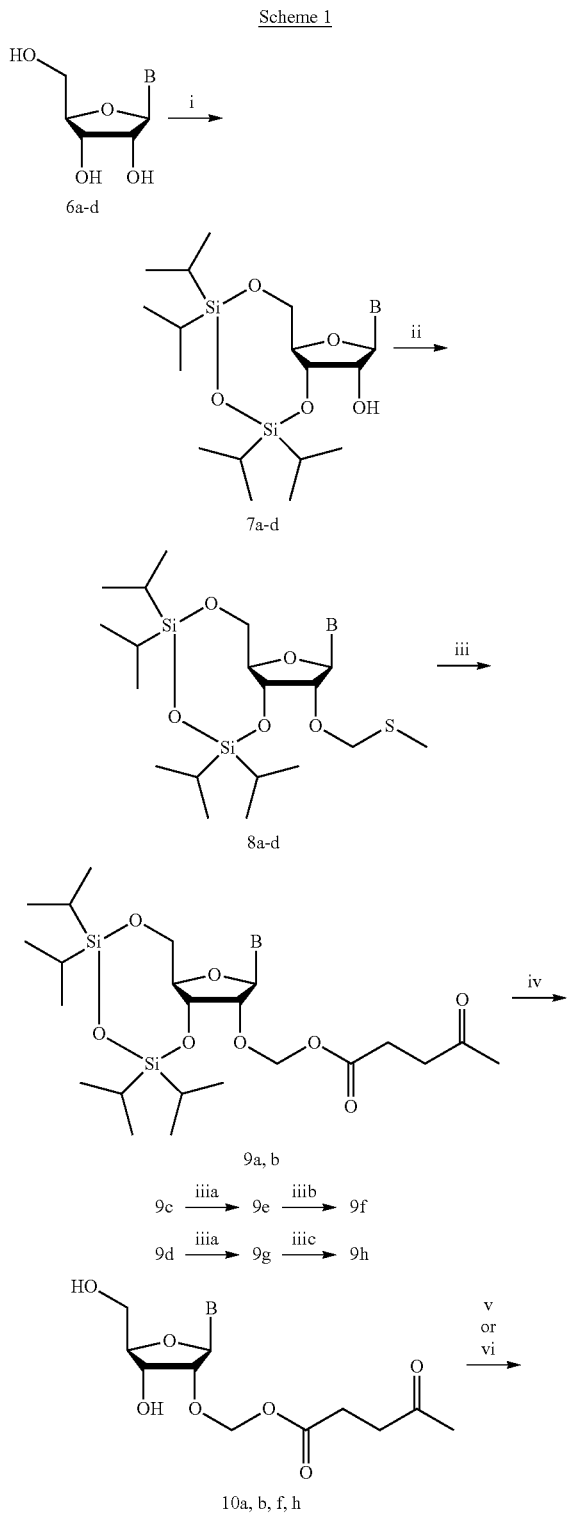

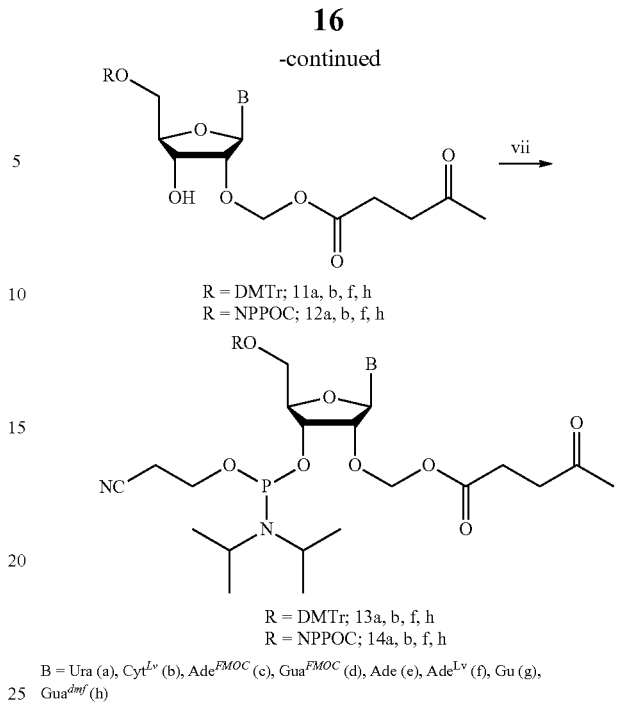

R = DMTr; 11a, b, f, h
R = NPPOC; 12a, b, f, h

R = DMTr; 13a, b, f, h
R = NPPOC; 14a, b, f, h

B = Ura (a), Cyt$^{Lv}$ (b), Ade$^{FMOC}$ (c), Gua$^{FMOC}$ (d), Ade (e), Ade$^{Lv}$ (f), Gu (g), Gua$^{dmf}$ (h)

In Scheme 1, the reagents used in each of the steps outlined are: (i) 1,3-dichloro-1,1,3,3-tetraisopropyldisiloxane (TIPDSCl), pyridine (py); (ii) dimethylsulfoxide (DMSO), acetic acid (AcOH) and acetic anhydride (Ac$_2$O); (iii) 1 M SO$_2$Cl$_2$, CH$_2$Cl$_2$, NaOLv, 15-Crown-5, CH$_2$Cl$_2$ (2 steps); for 3d, 1 M sulfuryl chloride (SO$_2$Cl$_2$), CH$_2$Cl$_2$, 4-Cl-styrene, Cs$_2$CO$_3$, levulinic acid; (iiia) 2:3 Net$_a$/py; (iiib) levulinic acid, 2-ethoxy-1-ethoxycarbonyl-1,2-dihydroquinoline (EEDQ), tetrahydrofuran (THF); (iiic) N,N-dimethylformamide dimethyl acetal, THF; (iv) NEt$_3$-3HF, THF; (v) DMTrCl, py; (vi) 5'-2-(2-nitrophenyl)propoxycarbonyl chloride (NPPOCCl)/py; (vii) CEtOP(Cl)NiPr$_2$, iPr$_2$NEt, CH$_2$Cl$_2$.

Referring to Scheme 1, Uridine (6a), N$^4$-Lv cytidine (6b), N$^6$-(9-fluorenylmethoxycarbonyl)adenosine (6c), and N$^2$-(9-fluorenylmethoxycarbonyl)guanosine (6d) were treated with 1,3-dichloro-1,1,3 3-tetraisopropyldisiloxane (TIPDSCl) in pyridine according to Markiewicz, 1979, Chem. Res. (S): 24-25, to give 7a-d in near quantitative yield. These materials were then reacted with DMSO, AcOH, and Ac$_2$O giving the 2'-O-thiomethyl ethers 8a-d in 63-88% yield (see, for example, Semenyuk et al., 2006, J. Am. Chem. Soc. 128: 12356-12357). Compounds 8a-c were treated with sulfuryl chloride (SO$_2$Cl$_2$) for 1 h, and the resulting 2'-O—CH$_2$Cl intermediates were combined with sodium levulinate (NaOLv) and 15-crown-5 ether to afford 9a-c in 78-94% yield. These conditions did not work well for 8d. Instead, this compound was reacted with SO$_2$Cl$_2$ in the presence 4-chloro-styrene to avoid side reactions on the guanine moiety. Without product isolation, this mixture was added to cesium carbonate and levulinic acid to provide 9d in 85% yield. At this point, the N-9-fluorenylmethoxycarbonyl ("FMOC") protected purines 9c and 9d were converted into the desired N-Lv (9f) and N-dimethylformamidine (dmf) (9h) derivatives. This "transient" FMOC protection was necessary as N-Lv and N-dmf groups on Ade and Gua, respectively, do not survive the conditions used to install the 2'-O-thiomethyl ether or 2'-O-ALE moieties (e.g., 7→8 and 8→9). Thus, compounds 9c, 9d were treated with 2:3 triethylamine/pyridine to remove the FMOC group in quantitative yield. Next, the resulting Ade 9e was reacted with 2-ethoxy-1-ethoxycarbonyl-1,2-dihydroquinoline (EEDQ) and levulinic acid to give the $N^6$-Lv Ade[37] 9f (86%), whereas Gua 9g was treated with N,N-dimethylformamide dimethyl acetal to give $N^2$-dmf Gua[38] 9 h in quantitative yield. Compounds 9a,b,f,h were then treated with $NEt_3$-3HF to afford 10a,b,f,h in nearly quantitative yields. To obtain monomers suitable for standard synthesis on controlled pore glass (CPG) solid supports, these nucleosides were treated with DMTrCl/pyr to afford 11a,b,f,h (78-90%), which were then 3'-phosphitylated under standard conditions to give 13a,b,f,h (70-90%). The corresponding 5'-O—NPPOC monomers were prepared from 10a,b,f,h by reaction with NPPOCCl/py and then CEtOP(Cl)N/$Pr_2$/DIPEA to afford 12a,b,f,h (30-65%) and 14a,b,f,h (85-88%), respectively.

Protection with the 9-fluorenylmethoxycarbonyl group (FMOC group) also remains an attractive option for RNA monomer protection. These can be removed at the end of synthesis by treatment with ethylenediamine/ethanol (Hogrefe et al. Nucleic Acids Res. 1993, 21(9): 2031-2038), or triethylamine/pyridine as demonstrated in the syntheses described in Scheme 1. Likewise, standard N-protection with acyl groups such as acetyl, benzoyl and isobutyryl groups may be used as they can be removed at the end of RNA synthesis with ethylenediamine under conditions we find also remove the 2'-ALE group. Shown in Scheme 2 below is a schematic illustration exemplifying the synthesis of N-FMOC-5'-DMTr-2'-ALE-3' amidites and N-FMOC-5'-NPPOC-2'-ALE-3' amidites.

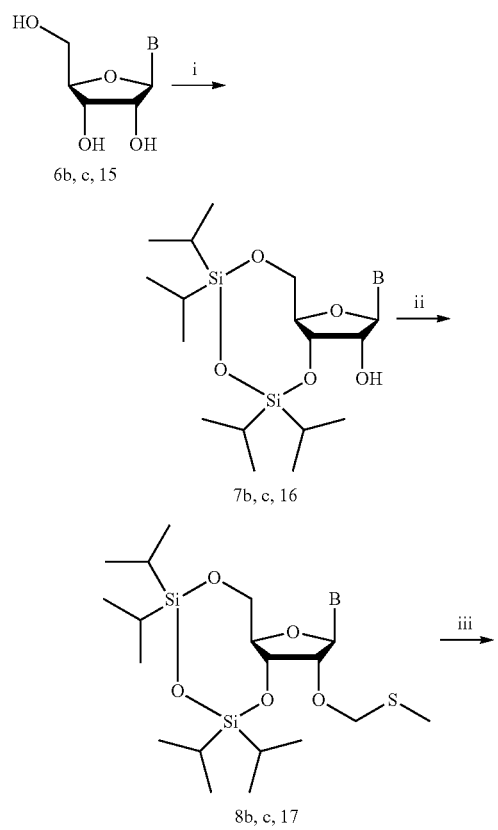

Scheme 2.

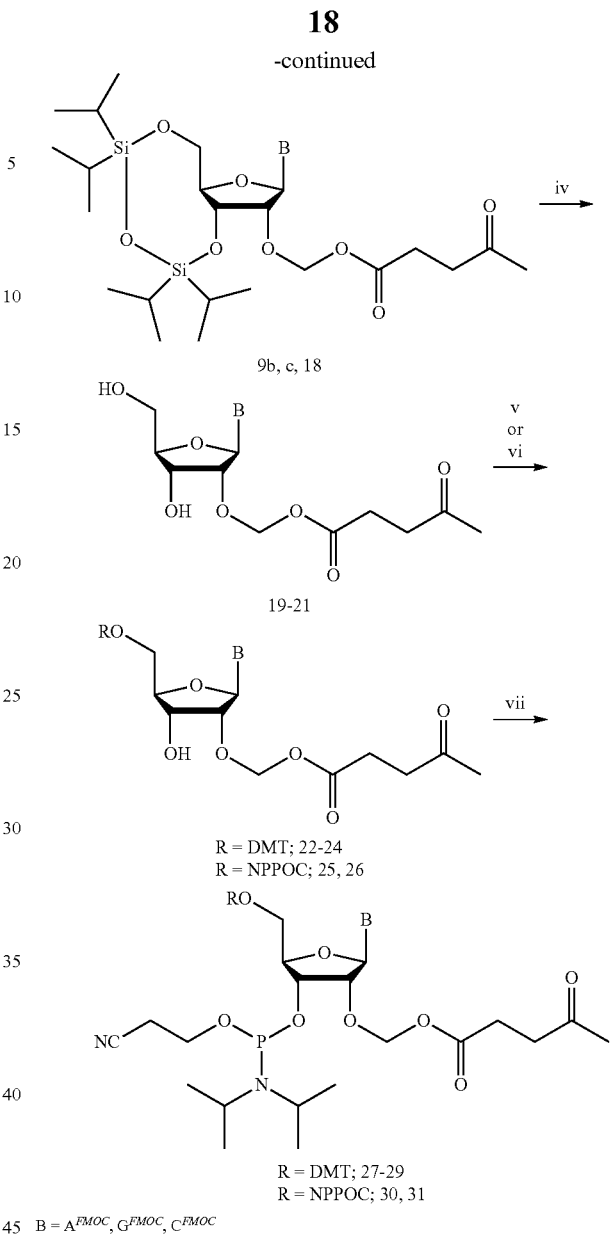

To demonstrate the utility of the phosphoramidites of the present invention, compound 13a was first activated with 4,5-dicyanoimidazole (DCI), and a coupling time of only 1 min was set for the preparation of a 12-mer chimeric oligonucleotide (5'-$rU_{11}$dT-3') starting from Q-linked dT-CPG (Yu and Pon, 1997, Nucleic Acids Res. 18: 3629-3635). The average coupling yield of phosphoramidite 7 was >98%, which is comparable to the average coupling yields of standard TBDMS RNA phosphoramidites under similar conditions.

Once the synthesis of the 2'-O-ALE oligomer was completed, the phosphate cyanoethyl groups were removed using 2:3 $NEt_3$/MeCN for 60 min. The 2'-O-ALE groups were then cleaved with 0.5 M hydrazine hydrate in 3:2 pyridine/acetic acid, r.t., 60 min. After a washing step, the oligomer was released from the Q-CPG solid support when treated with 1 M TBAF, at room temperature, overnight (Yu and Pon, 1997, Nucleic Acids Res. 18: 3629-3635). In performed experiments, its mass was confirmed by MALDI-TOF (calc. 3610. found 3611 [M+H+]). Despite their different coupling time (1 versus 10 min), both silyl and ALE phosphoramidite monomers afforded crude oligomers of excellent purity. This was confirmed via SDS-PAGE (24% PAGE) analysis of crude 5'-UUUUUUUUUUUdT-3' oligomers synthesized with 2'-ALE and 2'-TBDMS chemistry. Thus, 5'-UUUUUUUUUUUdT-3' could be synthesized from a phosphoramidite synthon 7 in excellent yields. In addition, a 21-mer 5'-GCUUGAAGUCUUUAAUUAAtt-3 (SEQ ID NO: 1) was also synthesized using phosphoramidite derivatives 14a,b,f,h, and 14a, 27-29 and full details of synthesis, purification and characterization are described below.

It is contemplated that the compositions and methods of the present invention may find a variety of uses. The development of novel chemistry for RNA monomer synthesis allows for compatibility of synthesis of RNA on solid substrates, for example on silanized glass surfaces, controlled pore glass (CPG), polystyrene, polyvinyl and other polymer supports. Embodiments of the present invention also include methods, processes, compositions, and structures that enable the synthesis of polynucleotides (e.g., RNA) with greater efficiency compared to previous methods. In particular, the present invention provides for methods, processes, compositions, and structures that overcome at least some of the problems of in situ RNA synthesis. In applications towards RNA microarray synthesis, preferred conditions would require that the protecting group deprotection is compatible with chemistry on glass substrates. More specifically, the conditions would facilitate simultaneous deprotection of the base protecting moieties and 2' protecting groups without nonselective cleavage of the oligoribonucleotides from the support.

Some advantages compared to present methods are indicated below. Although the chemistry is well established for the silyl ether protecting groups such as 2'-TBDMS and 2'-O-TOM, the glass substrate platform to be used in the microarray synthesis is sensitive to the fluoride conditions used to remove these 2'-protecting groups. As well, employing groups such as 2'-ACE requires stringent acidic and basic conditions of deprotection that may not be compatible with microarray fabrication. The 2'-O-4-MABOM group may be a potential substitute; however removal requires acid treatment which has been shown to cause internucleotide isomerization. Other acetal protecting groups such as 2'-O-Fpmp and 2'-O-Cpep may be used, though extended coupling times (i.e., over 10 min) would be required in the synthesis of longer length oligonucleotides. The use of a 2'-photolabile group is undesirable when used in conjunction with another photolabile group at position 5' (e.g., 5'-NPPOC), as they cannot be removed selectively from one another. Furthermore, other moieties such as the 2'-O-DTM (tert-butyldithiomethyl) group require a buffered solution of 1,4-dithioreitol, pH 7.5 and 55° C. for removal upon reduction. While this may be compatible with microarray synthesis, a disadvantage of monomers bearing a 2'-O-DTM group is their relative short shelf life. These limitations are addressed through the use of the acetal levulinyl (ALE) protecting group for the 2'-hydroxyl of cytidine (rC), guanosine (rG) and adenosine (rA), and uridine (rU). The rapid and very mild basic conditions required to remove the ALE protecting groups from the ribose and heterocyclic bases produces an intact and functional RNA strand directly attached to solid support surface such as a microarray surface. This chemistry has permitted the carrying out of the first in situ synthesis of RNA on microarrays, as described herein.

Embodiments of the present invention include the synthesis and use of RNA monomers presented in the form 5'-NPPOC-2'-ALE-3'-phosphoramidite for RNA synthesis and for in situ RNA microarray fabrication. The compound of formula VII above and/or functional homologs of the compound II such as 14a, 14b, 14f and 14h may thus be applied to microarray synthesis and generally to solid-phase synthesis of RNA.

The 5'-DMTr RNA monomers of the present invention, such as 13a, 13b, 13f and 13h, or 13a and 27-29 can be used for the synthesis of RNA oligos on solid substrate, for example for the synthesis of RNA oligonucleotide probes. The terms "oligonucleotide probes" are used for short, single stranded nucleotide multimers, generally used as probes in hybridization experiments (such as oligos bound to glass surfaces or nylon membranes). In particular, the present invention contemplates the use of oligoribonucleotide probes. The length of the oligos in the practice of the present invention can vary from about 30 RNA monomer units (i.e., 30-mers or 30-mer oligoribonucleotide probes) to about 100 RNA monomer units (i.e., 100-mers or 100-mer oligoribonucleotide probes). In one embodiment, the oligomers used in the practice of the present invention are 50-mers (i.e., 50-mer oligoribonucleotide probes). In yet another embodiment, the oligomers used in the practice of the present invention are 70-mers (i.e., 70-mer oligoribonucleotide probes). Longer oligoribonucleotide probes enable stronger hybridization, i.e. hybridization using higher stringency conditions, as described below. Hybridization using higher stringency conditions provides higher specificity and reduces non-specific binding.

The oligoribonucleotide probes may be immobilized on some type of solid support. The type of solid support can vary. For example, the solid support can be an article that includes one or more of porous substrates, non-porous substrates, three-dimensional surfaces, beads, planar surfaces, surfaces coated with gel-like materials, etched and otherwise structured surfaces, etc. Generally, the solid support should provide for a surface on which relatively high density of oligoribonucleotide probes can be attached. The substrate does not need to be flat, transparent nor uniform for successful synthesis in an MAS tool. The oligoribonucleotide sequences can be immobilized to the solid substrate using covalent attachments.

The oligoribonucleotide probes are immobilized on the solid support in the form of an array with a relatively high density. In one embodiment, array with preferred density of oligoribonucleotide probes immobilized on the solid support include arrays that may have at least 500,000 oligoribonucleotide probes per 1 $cm^2$ solid support surface. The relatively high density can be achieved using high density oligo array technology. For example, this can be conveniently achieved with a maskless array synthesizer with pixels as small at 2-15 microns, while gridded arrays require a pen that can deposit a spot with approximately 100 μm in diameter. The oligoribonucleotide probes thus occupy separate known sites in the array.

The oligoribonucleotide probes can be immobilized in the form of sets. For example, a set of oligoribonucleotide probes can be exactly complementary to a set of reference sequences, e.g. to a known genome. Another set of oligoribonucleotide probes can be identical to the first set of oligoribonucleotide probes but for at least one different nucleotide (i.e., one or more oligoribonucleotide probes can be modified to provide a desired mismatch vs. the set of reference sequences). Another set of oligoribonucleotide probes can be exactly identical to a set of reference sequences. Yet another set of oligoribonucleotide probes can be a reverse-complement to a set of known reference sequences. A variety of combinations of the above sets of arrays can also be immobilized on solid substrate, to provide a medley of various oligoribonucleotide probes that can be used for probing different properties of the complementary labeled polynucleotides that are hybridized to the array, as described below.

The polynucleotides of the present invention (one or more units) can be attached to suitable substrates that may have a variety of forms and compositions. The substrates can be in the form of solid supports with a variety of shapes, dimensions, and sizes. For example, the solid supports can be in the form of articles that include at least one of a porous substrate, a non-porous substrate, a three-dimensional surface, a bead, and a planar surface. The solid supports do not have to be equilateral, i.e. they can have asymmetrical sides. For example, solid support in the form of a cube can have three identical sides. Alternatively, solid support in the form of a cylinder can have two identical bases, and a wall of constant circular cross-section. The substrates may derive from naturally occurring materials, naturally occurring materials that have been synthetically modified, or synthetic materials. Examples of suitable support materials include, but are not limited to, nitrocellulose, glasses, silicas, teflons, and metals (e.g., gold, platinum, and the like). Suitable materials also include polymeric materials, such as plastics (for example, polytetrafluoroethylene, polypropylene, polystyrene, polycarbonate, and blends thereof, and the like), polysaccharides such as agarose (e.g., that available commercially as SEPHAROSE®, from Pharmacia) and dextran (e.g., those available commercially under the trade names SEPHADEX® and SEPHACYL®, also from Pharmacia), polyacrylamides, polystyrenes, polyvinyl alcohols, copolymers of hydroxyethyl methacrylate and methyl methacrylate, and the like.

Generally useful surfaces for microarray applications include silica based materials such as glass, silicon, and quartz. An alternative to glass substrates in microarray fabrication is that of the polymer based material PDMS (polydimethylsiloxane), which may be molded into microchannels through soft lithography (Moorcroft et al., 2005, Nucleic Acids Res. 33: 1-10). Since PDMS is incompatible with tetrahydrofuran and dichloromethane as a result of polymer swelling, alternative chemicals are used as substitutes in phosphoramidite chemistry, particularly that of the oxidizer, capping and deblocking reagents (detritylation in the case of DMTr-monomers). Carbon based materials have also been found to be stable substrates in the in situ light directed synthesis of microarrays (Phillips et al., 2008, Nucleic Acids Res. 36: 1-9), and these can be used as well. Essentially, any solid substrate materials that are compatible with the chemistry for light directed synthesis and phosphoramidite chemistry, and are robust to certain conditions (e.g., high temperature or pH variation) may be utilized in RNA microarray applications. Moreover, for solid-phase synthesis of RNA, materials such as controlled pore glass (CPG) may be employed.

RNA microarrays may be fabricated through various technologies, including but not limited to photolithography methods, photogenerated acid (PGA) chemistry with 5'-DMTr monomers, and ink-jet technology. In photolithographic methods, it is possible to synthesize oligonucleotide with up to 100 bases in length. Recently, inkjet microarray fabrication has shown capabilities of synthesizing oligonucleotide of up to 200 bases in length. In general, oligonucleotide synthesis may be carried on any DNA synthesizer pump system that is modified to the specifications required for the given microarray technology.

In one aspect, the compositions and methods of the present invention take advantage of the synthesis of photo-protected phosphoramidite monomers to generate high-density RNA arrays using the Maskless Array Synthesis (MAS) platform (Singh-Gasson et al., 1999, Nature Biotechnology 17: 974-978; Warren et al., 2006, Proc. Nat. Acad. Sci. USA 103: 867-872). In the light-directed RNA microarray synthesis strategy, standard phosphoramidite chemistry is used with modified monomers possessing photolabile protecting groups. The platform uses a maskless array synthesizer where deprotection and extension of each base may be activated in a site-specific fashion upon exposure to UV light, such as the technology used by NimbleGen Systems, Madison, Wis. A "MAS-derived microscope slide" refers to a microscopic slide on which an array of oligonucleotide probes (and oligoribonucleotide probes in particular) has been synthesized using a maskless array synthesizer. The location and number of sites are projected on the chip using lithographic-like method. Preferred designs may include alternates of frame pixels with empty "borders", such that the growth of each pixel is effectively isolated from the neighboring ones. Millions of individual pixels and thus independent sequences can be created on a chip, with densities in excess of 1 million per $cm^2$. In a preferred embodiment the MAS combines a custom illumination system, a Texas Instrument DLP chip, unique imaging optics and a microfluidic reaction cell where the oligonucleotides are synthesized. Deprotection of the RNA strands on MAS-derived microscope slides takes place while the oligomers are attached to the microarray, greatly simplifying and expediting the synthesis process. Designed arrays are used to explore RNA sequence-space—displaying randomized permutations of a single stranded RNA sequence, e.g. varying at as many as 10 positions. The arrays can be used with single-stranded, double-stranded, or otherwise structured RNA molecules. The sequence composition of the synthesized RNAs is controlled and defined by the researcher. In some examples, 5'-2-(2-nitrophenyl)propoxycarbonyl 2'-acetal-levulinyl RNA 3'-phosphoramidite monomers that are compatible with photolithographic synthesis have been synthesized. While the approach is superficially related to the construction of DNA microarrays, the conditions for RNA synthesis are considerably more stringent and require new approaches that cannot be predicted from standard practice of DNA microarray synthesis. The integrity of the bound RNA strands were confirmed through fluorescent hybridization experiments. This in situ synthesis allows for unparalleled chip complexity in an efficient and cost effective manner.

In some examples, homopolymer linkers are covalently attached to glass slides, and oligoribonucleotides are then synthesized on the homopolymers using phosphoamidite chemistry as described herein, to create a high-density RNA microarray.

The process of coupling and deprotection/oxidation is repeated until the oligonucleotide having the desired sequence and length is obtained (FIGS. 2 and 3). Following synthesis, the oligonucleotide may, if desired, be cleaved from the solid support.

The 5'-position of the RNA monomers may include both photolabile protecting groups and acid labile trityl groups in the preparation of RNA microarrays. For example, the photolabile 5'-nitrobenzyl protected RNA monomers may be used in the standard photolithographic synthesis method (Singh-Gasson et al., 1999), whereas 5'-DMTr monomers may be deprotected by photogenerated acid (PGA) (Gao et al., 2001, Nucleic Acids Res. 29: 4744-4750). Other microarray synthesis methods such as ink-jet strategies may also be employed using the derivatives described herein (Hughes et al., 2001, Nature Biotech. 19: 342-347).

Embodiments of the present invention include determining the presence or absence of target molecules in any sample. For example, certain target molecules may bind (hybridize) to the compositions of the present invention. Examples of samples that can be assayed include but are not limited to samples obtained from the environment, samples obtained from a human being or a non-human animal, and samples obtained from a water or food source. With a sample obtained from the environment, the existence of one or more target molecules in the environment can be determined. Target molecules may include: nucleic acids, for example, deoxyribonucleic acid (DNA); ribonucleic acid (RNA); oligonucleic acid; aptamer; peptide nucleic acid (PNA); morpholino; locked nucleic acid (LNA); glycol nucleic acid (GNA); and threose nucleic acid (TNA); peptides, proteins, polypeptides, and other proteinaceous molecules; small molecules, and other molecules that bind to the RNA molecules of the present invention. Suitable hybridization and washing conditions will depend on specific applications. In general, the higher the degree of similarity between two target molecules that need to be differentiated, the higher the stringency of hybridization and washing conditions should be. The target molecules can optionally be labeled.

The invention also relates to target molecules that selectively hybridize to the exemplified oligoribonucleotide sequences, including hybridizing to the exact complements of these sequences. The specificity of nucleic acids to hybridize complementary fragments is determined by the "stringency" of the reaction conditions. Hybridization stringency increases as the propensity to form nucleic acid duplexes decreases. In nucleic acid hybridization reactions, the stringency can be chosen to either favor specific hybridizations (high stringency), which can be used to identify, for example, full-length clones from a library. Less-specific hybridizations (low stringency) can be used to identify related, but not exact, target molecules (e.g., homologous, but not identical nucleic acid molecules) or segments.

The compositions and methods of the present invention may be used to comprehensively and quantitatively define the recognition landscapes of RNA binding molecules. These RNA binding molecules include, but are not restricted to, proteins, peptides, RNAs and DNAs, small molecules, and substrates for RNA-mediated catalysis. The methods described herein enable the detection of the binding of any class of molecule to immobilized RNAs, for example with the purpose of identifying RNAs to which they bind, quantitating that interaction, deriving RNAs with new properties, including catalysis.

It is contemplated that the compositions and methods of the present invention find utility in various analyses, including RNA-protein and RNA-peptide interactions. RNA-protein interactions determine when, where, and how much protein is made by a particular mRNA. To date, only a few RNA-protein interactions have been scrutinized in detail. For practical reasons, almost all studies focus on the higher-affinity binding sequences; yet in many instances, lower affinity sequences are biologically critical. Similarly, for understanding the specificity of any given protein or peptide, the methods uniquely enable to describe binding to a large array of sequences, thereby making it possible to assess the relative binding to target and non-target RNAs. Such studies will enable the design of compounds with designed specificities, and with the desired binding properties, as has been possible with DNA arrays. The methods described herein enable the determination of the full-spectrum of RNA recognition properties for a given protein or complex and to elucidate unambiguously the biological consequences of that recognition landscape in vivo. High density RNA microarrays, prepared using photolabile RNA monomers on a maskless array synthesizer, may be used to determine the affinity of a protein or complex for millions of different RNA sequences in a single, rapid experiment.

In general, RNA-nucleic acid duplexes are stabilized by: (1) the number of complementary base pairs, (2) the type of base pairs, (3) salt concentration (ionic strength) of the reaction mixture, (4) the temperature of the reaction, (5) the presence of certain organic solvents, such as formamide which decreases nucleic acid duplex stability, and (6) chemical modifications in the RNA strand that are known to enhance the melting temperature of the duplex, for example incorporation of LNA, and 2'-modified RNA monomers such as 2'-fluororibonucleosides, 2'-O-methylribonucleosides, etc. In general, the longer the probe, the higher the temperature required for proper annealing. A common approach is to vary the temperature: higher relative temperatures result in more stringent reaction conditions.

To hybridize under "stringent conditions" describes hybridization protocols in which nucleotide sequences in the two strands are at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer or oligonucleotide to hybridize only to its target sequence. Stringent conditions are sequence-dependent and will differ. One stringent condition example comprises hybridization in 1 M [Na+], 100 mM MES, 20 mM EDTA, and 0.01% Tween-20 at 45° C., with washes at 45° C. in 6×SSPE, 0.01% Tween-20, followed by a high-stringency wash consisting of 100 mM MES salt and free acid solution, 0.1M [Na+], 0.01% Tween-20. Preferably, the conditions are such that sequences at least about 65%, 70%, 75%, 85%, 90%, 95%, 98%, 99%, or 100% homologous to each other typically remain hybridized to each other. These conditions are presented as examples and are not meant to be limiting.

"Moderately stringent conditions" use washing solutions and hybridization conditions that are less stringent (Sambrook et al., 1989), such that a polynucleotide will hybridize to the entire, fragments, derivatives, or analogs of a target sequence. One example comprises hybridization in 6×SSC, 5×Denhardt's solution, 0.5% SDS and 100 µg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described in the art (Ausubel et al., 1993; Kriegler, 1990).

"Low stringent conditions" use washing solutions and hybridization conditions that are less stringent than those for moderate stringency (Sambrook et al., 1989), such that a polynucleotide will hybridize to the entire, fragments, derivatives, or analogs of a given oligonucleotide sequence. A nonlimiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 µg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross species hybridizations, are well-described (Ausubel et al., 1993; Kriegler, 1990).

In some examples, the compositions and methods of the present invention can be used in the synthesis of aptamers. Various aspects of the synthesis and functions of aptamers are disclosed in Warren et al., 2006, Macromolecular Interactions: Aptamers, In: Encyclopedia of Life Sciences, John Wiley & Sons, which is herein incorporated by reference.

After hybridization of the labeled target and/or reference sequences to the immobilized RNA oligomers, signal detection is performed. Detection of the signal can be performed in a variety of ways known in the art. In one standard example, the RNA microarrays are scanned using a standard laboratory confocal microscope, with its routine 2 µm or better resolution, and analyzed with software that allows automatic quantification of the approximately 768,000 fluorescent spots on the 17 mm$^2$ glass surface. The detected signal can be originating from one or more labels. Thus, the RNA molecules of the present invention can optionally be labeled. A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or proteins for which antisera or monoclonal antibodies are available. The present invention contemplates the use of labeled nucleic acids, such as labeled RNA.

Significant differences exist between DNA and RNA array synthesis. As a general observation, standard DNA synthesis conditions are not suitable for RNA synthesis. An important difference is the need for a protecting group for the 2'-OH group that is absent in DNA. Deprotection may be simultaneously performed, or it may be performed as a two-step deprotection procedure during RNA synthesis. This could not have been predicted on the basis of current knowledge. Synthesis modification requires that NPPOC group be deprotected at 6.5 J exposure versus 6 J. Also, DCI activator is preferably used during coupling of the phosphoramidite. Other activators such as ethyl-thiotetrazole do not give optimal coupling yields. Prior to hybridization the 2'-ALE protecting group must be removed. Thus decyanoethylation is preferably initially conducted, followed by removal of the 2'-ALE group using hydrazine hydrate. Preferably, a washing procedure is conducted to remove any undesired salts that may form during the deprotection, for example using 1:1 (v/v) pyr:HOAc. For hybridization, precaution must be taken to avoid exposure of RNA microarrays to RNases, thus preventing enzymatic degradation. It is recommended not to "blow" air on a slide, which is common practice when trying to visualize DNA microarrays. The enzymes from the moisture on one's breath may cause degradation. RNAse-free regents, for example DPC treated autoclaved H$_2$O, must be used to prepare all buffers for hybridization. In some embodiments, optimal hybridization is observed when 10 mM MgCl$_2$ (divalent cation) is used within the matrix of the buffer.

For the use of microarray synthesis alternative groups to ALE, such as the Lv group may be utilized in the protection of the 2'-hydroxyl. The 2'-ALE group is preferred due to advantages in relative ease of monomer synthesis and purification. The 2'-Lv chemistry developed for the solid-phase synthesis of RNA on controlled pore glass (CPG), while providing RNA efficiently, requires tedious purification of isomeric 2'-Lv and 3'-Lv ribonucleosides, which must be separated prior to 3'-phosphoramidite synthesis (Lackey et al, 2007, Org. Lett. 9: 789-792). No such complications arise with the ALE protecting group since it is unable to isomerize under the conditions to install the 3'-phosphoramidite moiety.

One advantage of this approach, compared to standard methods (e.g., conventional biochemistry or SELEX), is that quantitative information is obtained for binding to all RNA sequences, as has been achieved with duplex DNA. The methods of the present invention permit analysis of any set of more than a million sequences, and they are unconstrained by the restrictions of mask-based or spotted array methods. As many as 10$^6$ features can at present be displayed on a single array, permitting the analysis of affinities for 10$^6$ different RNA sequences simultaneously, and higher densities have been demonstrated. For RNA-binding DNA sequences, the approach is robust and reproducible over nine orders of magnitude: $K_d$S from $10^{-3}$ to $10^{-12}$ M can be determined.

Other advantages compared to present methods are indicated below. Previous attempts to create RNA arrays relied on RNA biosynthesis from DNA, followed by physical deposition on a surface; however, that approach can only access limited sequence-space and suffers from the well-known constraints of "spotted" arrays. These include, but are not limited to, variability due to non-uniform deposition of material during spotting, highly variable spreading and distribution of material on the surface, non-uniform adhesion and attachment of biomolecules and steady detachment of nucleic acid from surfaces upon long incubations. In addition, the density of features on spotted arrays fails to approach the millions of features that can be spatially resolved with high confidence on in situ synthesized nucleic acid arrays. The chemical synthesis approach of the present invention circumvents these problems and enables the scrutiny of specific proteins and multicomponent complexes in systematic and quantitative fashion. Conventional biochemical methods, even when combined with extensive mutagenesis, can analyze only a handful of sequences. Among such methods are EMSA, fluorescence polarization, filter binding and other methods well known to those skilled in the art. For all these approaches that measure the binding of a protein to a particular RNA, the methods impose severe restrictions on the number of RNAs that can be analyzed. For a 10 nt RNA, 31 separate RNA binding experiments must be performed to test a single substitutions; the total number of possible sequences is $4^{10}$. Methods such as SELEX (reiterative selections) allow access to a very large population of RNA molecules, but practically speaking, it is necessary to examine binding to only those that bind well. The methods of the present invention are not restricted in that fashion. Other existing approaches include co-immunoprecipitation (RIP-chip) studies, in which physical associations of an RNA with a binding partner are analyzed. These experiments provide little quantitative information, do not identify binding sites, and are biased by RNA abundance. The methods described herein circumvent all of these limitations; they provide comprehensive quantitative information, identify the particular sequences with which a protein or peptide interacts, and are unaffected by the natural abundance of the RNAs. Yet other existing approach is to test populations of RNAs that bind a particular protein by hybridizing those RNAs to a DNA microarray. This approach is restricted by the number of RNAs that can be analyzed, and in dynamic range. Determining RNA binding in this manner necessitates nearly micromolar concentrations of each member of a library, linear range of binding and dissociation of RNA molecules from the binding partner, and uniform hybridization to a DNA array. Typically, like SELEX assays, only the best binding sequences may be identified by such an approach. Similar to DNA binding profiles, this approach will fail to identify medium-to-weak binding sequences and will compress the texture in the best binding sequences. The recognition motifs that emerge from such experiments will necessarily be limited in their information content. Moreover, RNA molecules that do not adopt complex tertiary conformations will be more abundantly identified and the better binders that do not denature and hybridize to DNA arrays will, as a class, be underrepresented, even if they are the best binders in the RNA library. The ability of RNA molecules to adopt structure is what may limit other means of identifying RNA molecules by hybridization to DNA arrays and provides impetus to develop RNA-based microarrays.

Each feature of an RNA microarray may be composed of many copies of a specific RNA sequence. Each feature represents a different sequence and all the features on the microarray are designed to cover a diverse set of RNA sequences. Each feature/sequence on the microarray may form a different structure (e.g. single-stranded, double-stranded, bubble, bulge, G-quadruplex). Since the array is synthesized as single-stranded RNA, potential RNA structures are first induced on the array. Microarray slides are first immersed in 1×PBS and placed in a 90° C. water bath for 30 min to induce potential structure formation of the RNA. Slides are then transferred to a tube of wash buffer (saline/sodium phosphate/EDTA buffer, pH 7.5, 0.01% Tween-20) and scanned to check for low background. Microarrays are scanned by using a 3.25 μm scanner (ArrayWorx).

The array is then incubated with a blocking agent, such as non-fat dried milk, for an hour to prevent the purified protein from aggregating on the surface of the array (this treatment may vary for different proteins). The array is incubated with protein in an appropriate buffer (e.g. 200 mM KCl, 20 mM HEPES pH 7.0, 1 mM DTT, 5% glycerol, 0.005% Tween-20) along with a fluorescent antibody to the protein for an hour. The array is quickly washed with buffer to remove residual unbound protein and antibody, dried by centrifugation, and scanned.

Alternatively, the protein may be directly labeled with a fluorescent dye rather than requiring a fluorescently labeled antibody. Protein labeling can be performed through standard protocols (e.g. maleimide conjugation to solvent exposed cysteines).

Optimal detection of protein-RNA interactions may require optimization for array surface treatment, protein concentration, temperature, and the use of protein stabilizers. Protein aggregation on the array surface can cause high or saturating background fluorescence. Various blocking agents such as non-fat dried milk, bovine serum albumin, fetal bovine serum, or the like, can be used to reduce non-specific interactions and aggregation of the protein of interest.

Another challenge may be low-threshold detection of specific protein binding to RNA on the RNA array. To address this, several parameters can be optimized. Usual concentrations tested are 0.1 nM-to-1 μM, with the lowest concentrations tested first. Salt concentrations, salt buffer composition (e.g. NaCl, KCl, potassium phosphate, or potassium glutamate), and buffer pH needs to be optimized. Initial hybridizations are usually performed at room temperature, but decreasing the temperature to 4° C. may improve the stability of some protein-RNA complexes. This has been shown to be effective for many protein-DNA interactions on similar microarrays.

Non-specific protein binding is typically resolved by reducing the protein concentration or increasing the salt concentration in the buffer. Poly-dl-dC and heparin which mimic DNA charge distribution or salmon sperm DNA which is composed of actual DNA fragments (~200-2,500 bp) can be included in the buffer at concentrations ranging from 0.05 to 1 mg/mL in the experiments, similar to EMSA and ChIP-chip protocols.

The binding of each protein will be idiosyncratic. Key issues that must be dealt with for each protein include: optimal salt concentration, pH, and divalent metal ions; adherence to the surface; nonspecific binding to the RNA or the moiety used to attach it to the surface. It is possible to control for these factors in multiple ways. A variety of buffer compositions and incubation conditions may be tested using derivatized slides to determine the most optimal binding/reaction environment. Sample buffers that can be used with the microarrays include: 1) 50 mM NaCl, 20 mM Tris pH 7.0, 1 mM DTT, 5 mM $MgCl_2$, 0.01% Triton-X; 2) 200 mM KCl, 50 mM HEPES pH 7.5, 10% glycerol, 0.1 mg/mL BSA; 3) 125 mM Potassium glutamate, 50 mM phosphate buffer pH 8.0, 3 mg/mL BSA; 4) 1×PBS, 0.1 mg/mL salmon sperm, 0.0002% Tween-20.

In some embodiments of the present invention, provided are compositions and methods for the analyses of RNA-RNA interactions. The interactions of RNAs with one another are critical in biology. Ribosomes, spliceosomes, viral genomes, microRNAs—all of these rely on interactions between RNA molecules. Often, the interactions involve not merely base-pairing but novel atomic interactions. The RNA arrays described herein enable the analysis of RNA-RNA interactions by methods analogous to those described above for proteins. For example, an RNA corresponding to the microRNAs, let-7, is shown to hybridize to its natural binding site in the human ras 3'UTR. Another example of RNA-RNA interaction involves the use of a structured RNA population on the array. In this case, the binding of a tetraloop (a stem-loop containing 4 nts in the loop) with the so-called tetraloop receptor, to which it binds tightly, is examined. The interaction provides a common means, in nature, of bringing two duplex RNAs together. The tetraloop binds to the receptor RNA and not to control RNAs. Similarly, one of skilled in the art will be able to determine the specificity of interactions between structured RNAs, or one RNA that is structured and another that is not. The binding may similarly be idiosyncratic, though not as much as for proteins.

One embodiment of an RNA-RNA hybridization protocol is as follows. Obtain fluorescently labeled RNA for hybridization (e.g. by purchase or using standard RNA labeling protocols). Dilute labeled RNA to ~50 nM in a standard buffer (e.g. 50 mM NaCl, 20 mM Tris pH 7.0, and 1 mM DTT). Wash microarray surface with the standard buffer. Incubate the labeled RNA with the microarray overnight (16-20 hours) with rotation at 45° C. (if RNA is greater than 20 nucleotides). If RNA is less than 20 nucleotides incubate at room temperature or 4° C. If fluorescently labeled RNA is a mixture of sequences, or the RNA sequence is known to form a secondary structure, heat the labeled RNA sample to 95° C. for 5 minutes before incubating with the microarray.

Non-specific DNA, such as salmon sperm, can be added to incubation mixture to decrease non-specific microarray binding by labeled RNA. Remove labeled RNA and wash microarray surface with the standard buffer. Dry microarray by centrifugation and scan with a standard microarray scanner (e.g. ArrayWorx 3.25 µm resolution scanner). Similar to the RNA-protein binding methods described above, controls and optimization of the methods may be performed.

In some embodiments of the present invention, provided are compositions and methods for the analyses of small molecule-RNA interactions. Small organic and inorganic molecules bind tightly to RNA. For example, Mg ions commonly stabilize RNA structures or interactions between RNA chains; aminoglycosides bind avidly to define RNA structures. However, the determination of the specificity of these molecules is challenging, for the same reasons as described for protein-RNA interactions. The value of such analysis is two-fold. First, the specificities of known compounds can be evaluated comprehensively. Second, new compounds can be derived that bind more tightly than parental molecules, with full knowledge of their binding properties. Such an approach has yielded DNA-binding molecules that bind tightly and with high specificity. One value of this novel form of analysis is that it enables the development of small molecules that activate, repress or localize individual RNAs; interfere with their interactions with specific regulatory components; attract specific proteins to the RNA.

Experimental techniques including inducing potential RNA structures on the microarray and incubating the microarray with the small molecule remain the same as for that of a protein. In this case, however, it is more likely to directly fluorescently label the small molecule since antibodies are less common. Some small molecules fluoresce on their own or when bound to RNA, and so labeling may not be necessary in certain cases (e.g. ethidium bromide, sybr green, etc.). Optimization remains the same as for proteins, although small molecules are often less prone to aggregation on the surface. Experiments have already been performed to successfully define the sequence recognition properties of small molecule DNA binding ligands (Warren et al., 2006, Puckett et al., 2007). Thus, aspects of the methods that some of the inventors have developed to obtain high-resolution DNA sequence binding profiles of small molecule DNA ligands can also be used. In the past these methods have yielded high-quality, high-resolution profiles of small molecules as well as ternary complexes between DNA binding small molecules and their cognate site on the DNA (Warren et al., 2006). Similar procedures can be used with RNA.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

Example 1. Protocols for the Synthesis of 5'-O-2-(2-nitrophenyl)propoxycarbonyl-2'-O-acetal levulinylester-3'-O-2-cyanoethyl N,N-diisopropyl)phosphoramidite ribonucleosides Scheme 1 shows the synthesis of 2'-ALE ribonucleoside amidite derivatives. Aspects useful for the synthesis of the uridine amidite are described in Zavgorondy et al., 1991, Tetrahedron Lett. 7593; Rastogi and Usher, 1995, Nucleic Acids Res. 4872-4877; and in Parley et al., 2006, Org. Lett. 3869-3872. Aspects useful for the synthesis of 2'-ALE cytidine amidite are described in Zavgorondy et al., 1991, Tetrahedron Lett. 7593; Rastogi and Usher, 1995, Nucleic Acids Res. 4872-4877; and in Parley et al., 2006, Org. Lett. 3869-3872. Aspects useful for the synthesis of 2'-ALE adenosine amidite are described in Heikkilii and Chattopadhyaya, 1983, Acta. Chem. Scand. 263; Chladek et al., 1987, J. Org. Chem. 5387; and in Chladek et al., 1988, J. Org. Chem. 5040. Aspects useful for the synthesis of 2'-ALE guanosine amidite are described in Heikkilii and Chattopadhyaya, 1983, Acta. Chem. Scand. 263; Chladek et al., 1987, J. Org. Chem. 5387; and in Chladek et al., 1988, J. Org. Chem. 5040.

General remarks. $^1$H NMR spectra were recorded at 500 MHz and the chemical shifts were measured from the solvent peak as an internal standard (in $CDCl_3$, $CD_3CN$ or $DMSO-d_6$). $^{31}$P NMR spectra were recorded at 80 MHz and the chemical shifts were measured from 85% $H_3PO_4$ as an external standard. Mass spectra were recorded using ESI-TOF. Thin layer chromatography was performed on EM Science Kieselgel 60 F-254 (1 mm) plates. Silicycle 40-63 µm (230-400 mesh) silica gel was used for flash chromatography. Pyridine, acetonitrile, and dichloromethane (DCM) were distilled from $CaH_2$ after refluxing for several hours. THF was distilled from benzophenone and sodium after refluxing for several hours. All other anhydrous solvents were purchased from Sigma-Aldrich. Chemicals and reagents were purchased from Sigma-Aldrich. All anhydrous reactions were run under argon or nitrogen atmosphere in flame-dried glassware.

N4-levulinyl-cytidine (6b) was prepared according to Lackey, J. G.; Sabatino, D.; Damha, M. J. Org lett. 2007, 9, 789-792 and Ogilvie, K. K.; Nemer, M. J.; Hakimelahi, G. H.; Proba, Z. A.; Lucas, M. Tetrahedron Lett. 1982, 23, 2615-2618.

N6-(9-Fluorenylmethoxycarbonyl)-adenosine (6c) was prepared according to Happ, E.; Scalfi-Happ, C; Chladek, S. J. Org. Chem. 1987, 52, 5387-5391.

N2-(9-Fluorenylmethoxycarbonyl)-guanosine (6d) was prepared according to Heikkla, J., Chattopadhyaya. J. Acta. Chem. Scand. Ser. B, 1983, B37, 263-271 and Hagen, J.; Scalfi-Happ.; Happ, E.; Chladek, S. J. Org. Chem. 1988, 53, 5040-5045.

The preparation of 3',5'-O-(1,1,3,3-tetraisopropyldisiloxane-1,3-diyl) ribonucleosides (7a-d) were carried out according to Markiewicz, W. T. J. Chem. Res. (S) 1979, 24-25; Markiewicz, W. T J. Chem. Res. (M) 1979, 181-197.

For example, uridine (41 mmol) is dissolved in 100 mL of pyridine. The Markiewicz reagent (43 mmol) is added dropwise under a dry nitrogen environment over 25 min. After 3 hrs, the reaction has gone to completion. It is quenched with 20 mL of brine, and then concentrated to an oil under reduced pressure. This residue is then redissolved in 200 mL of dichloromethane (DCM) and washed once with 50 mL of brine. The aqueous layer is then washed 3× with 50 mL of DCM. Organic extracts are then pooled and dried over $MgSO_4$, filtered and concentrated. The resulting sticky foam is then coevaporated 3× with 30 mL of benzene and pumped on high vacuum to give a white foam in near quantitative yield. This material is used without further purification in the next synthetic step.

The preparation of 3',5'-O-(1,1,3,3-tetraisopropyldisiloxane-1,3-diyl)-2'-O-(methylthio)methyl ribonucleosides (8a-d) were carried out following modifications of the procedures reported by Semenyuk, A.; Földesi, A.; Johansson, T.; Estmer-Nilsson, C; Blomgren, P.; Brannvall, M.; Kirsebom, L. A.; Kwiatkowski, M. J. Am. Chem. Soc. 2006, 128, 12356-12357.

For example, 3'-5'-O-(1,1,3,3-tetraisopropyldisiloxane-1,3-diyl)-uridine (7a) (20 mmol) is dissolved in 30 mL of DMSO followed by the addition of 30 mL glacial acetic acid and 20 mL of acetic anhydride. This reaction mixture is stirred for 20 hr at room temperature and then heated for 4 hrs at 50° C. to drive the reaction to completion. The reaction is then cooled to room temperature and poured into a 2 L Erlenmeyer flask. This material is then stirred vigorously and a solution of $K_2CO_3$ (100 g in 1 L) is added. The white precipitate is filtered and dissolved in 200 mL of DCM. This material is transferred to a reparatory funnel and the excess aqueous material is removed. The organic material is dried over $MgSO_4$ and the solvent is removed under reduced pressure to give a yellowish foam. This material is purified by column chromatography (0-2% MeOH in DCM) and 3',5'-O-(1,1,3,3-tetraisopropyldisiloxane-1,3-diyl)-2'-O-(methylthio)methyl uridine (8a) is obtained in an 88% yield. The characterization of 8a is in agreement with Semenyuk, A.; Foldesi, A.; Johansson, T.; Estmer-Nilsson, C; Blomgren, P.; Brannvall, M.; Kirsebom, L. A.; Kwiatkowski, M. J. Am. Chem. Soc. 2006, 128, 12356-12357.

TABLE 1

Column chromatography and yields of compounds 8b-8d.

| Compound | mmol (starting) | Column conditions | Yield |
|---|---|---|---|
| 8b | 26 | 0→2% MeOH in DCM | 82 |
| 8c | 16 | 60:40 hexanes/EtOAc | 65 |
| 8d | 18 | 40:60 hexanes/EtOAc | 63 |

Spectroscopic and mass spectral data of compounds 8b, 8c and 8d.

N4-levulinyl-3',5'-O-(1,1,3,3-tetraisopropyldisiloxane-1,3-diyl)-2'-O-(methylthio)methyl cytidine (8b)

$^1$H NMR (500 MHz, DMSO-d6): δ 10.94 (s, 1H), 8.07 (d, 1H, J=9.5), 7.18 (d, 1H, J=9.5), 5.65 (s, 1H), 5.00-4.96 (m, 2H), 4.32 (d, 1H, J=5.5), 4.22 (d, 1H, J=16.5), 4.18-4.14 (m, 1H), 4.09-4.07 (1H, m), 3.93-3.90 (1H, d, J=16.5), 2.72-2.69 (m, 2H), 2.59-2.56 (m, 2H), 2.09 (s, 3H), 2.10 (s, 3H), 1.05-0.95 (m, 28H). $^{13}$CNMR (125 MHz, DMSO-d6): 207.7, 207.2, 173.8, 163.2, 154.8, 143.9, 95.8, 89.7, 81.8, 77.7, 73.7, 67.8, 60.0, 34.1, 31.0, 30.3, 28.6, 17.9, 17.8, 17.6, 17.5, 17.4, 13.4, 13.2, 13.1, 13.0, 12.6. ESI-TOF calc for $C_{26}H_{45}N_3O_3SSi_2$ 666.30+ (+Na$^+$). found 666.32.

N6-(9-Fluorenylmethoxycarbonyl)-3',5'-O-(1,1,3,3-tetraisopropyldisiloxane-1,3-diyl)-2'-O-(methylthio)methyl adenosine (8c)

$^1$H NMR (500 MHz, CDCl$_3$): δ 9.45 (s, 1H), 8.77 (s, 1H), 8.34 (s, 1H), 7.74-7.72 (m, 2H), 7.61-7.58 (m, 2H), 7.38-7.35 (m, 2H), 7.26-7.22 (m, 2H), 6.06 (s, 1H), 5.05, 4.98 (abq, 1H each, J=11, 11.5), 4.72-4.69 (m, 1H), 4.67-4.59 (m, 2H), 4.38-4.31 (m, 1H), 4.21, 4.02 (abq, 1H each, J=13.5, 13.5), 4.17-4.14 (m, 1H), 2.17 (s, 3H), 1.11-0.94 (m, 28H). $^{13}$CNMR (125 MHz, CDCl$_3$): δ 153.1, 151.6, 150.7, 149.8, 143.9, 143.7, 141.5, 141.5, 141.2 128.0, 128.0, 127.9, 127.4, 125.3, 125.2, 122.9, 120.3, 120.2, 88.8, 82.0, 75.0, 69.1, 68.0, 59.9, 47.15, 17.7, 17.6, 17.5, 17.45, 17.4, 17.38, 17.32, 17.3, 17.2, 17.1, 13.7, 13.6, 13.2, 13.0, 12.9. ESI-TOF calc for $C_{39}H_{53}N_5O_7SSi_2$ 814.32 (+Na$^+$). found 814.28.

N2-(9-Fluorenylmethoxycarbonyl)-3',5'-O-(1,1,3,3-tetraisopropyldisiloxane-1,3-diyl)-2'-O-(methylthio)methyl guanosine (8d)

$^1$H NMR (500 MHz, CDCl$_3$): δ 11.29 (s, 1H), 8.32 (s, 1H), 7.98 (s, 1H), 7.75-7.73 (m, 2H), 7.57-7.54 (m, 2H), 7.41-7.37 (m, 2H), 7.31-7.26 (m, 2H), 5.86 (s, 1H), 4.98, 4.94 (abq, 1H each, J=11.5, 11.5), 4.63-4.56 (m, 1H), 4.52-4.49 (m, 1H), 4.44 (d, 1H, J=5), 4.25-4.20 (m, 2H), 4.13-4.10 (m, 1H), 4.00-3.97 (m, 1H), 2.14 (s, 3H), 1.10-0.92 (m, 28H). $^{13}$CNMR (125 MHz, CDCl$_3$): δ 155.8, 153.7, 147.6, 146.8, 143.1, 141.5, 136.6, 128.3, 127.5, 125.0, 121.7, 120.4, 87.92, 82.0, 78.2, 74.6, 68.7, 68.5, 59.9, 46.9, 17.7, 17.5, 17.4, 17.3, 17.25, 17.2, 17.1, 13.7, 13.6, 13.2, 13.1, 12.8. ESI-TOF calc for $C_{39}H_{53}N_5O_3SSi_2$ 830.32 (+Na$^+$). found 830.32.

General Procedure for the Preparation of 3',5'-O-(1,1,3,3-tetraisopropyldisiloxane-1,3-diyl)-2'-O-acetal levulinyl ester nucleosides (9a,b, c)

As an example, the synthesis of 9a is provided.

3',5'-O-(1,1,3,3-tetraisopropyldisiloxane-1,3-diyl)-2'-O-acetal levulinylester uridine (9a)

Compound 8a (17 mmol) is freeze dried in dry benzene. It is then dissolved with 170 mL DCM under a dry nitrogen environment and is cooled to 0° C. 17 mL of a freshly prepared 1 mol/L solution of sulphuryl chloride is then added dropwise over 15 minutes. The reaction is stirred for an additional 30 minutes and then warmed to room temperature. It is then stirred for an additional 30 minutes. The solvent is then removed under reduced pressure and is repressurized with dry nitrogen giving a yellow foam. This material is then redissolved with 85 mL of DCM and sodium levulinate (43 mmol) is added to the stirring solution followed by the addition of 15-crown-5 (10 mmol). The reaction mixture is stirred for 2 hr and then is diluted with 250 mL of DCM. The solution is then washed once with 150 mL of water. The aqueous layer is then washed with 3×100 mL of DCM. The organic extracts are pooled and dried over $MgSO_4$. After filtration, the solvent is removed under reduced pressure to give yellowish foam. This crude material is then purified by column chromatography (0→1% MeOH in $CH_2Cl_2$) giving 9a as a white foam in 86% yield. The same chromatography conditions apply to 9b, 78% yield. For 9c use 70:30 hexanes/EtOAc→60:40 hexanes/EtOAc, 94% yield.

Spectroscopic and Mass Spectral Data of Compounds 9a, 9b and 9c.

3',5'-O-(1,1,3,3-tetraisopropyldisiloxane-1,3-diyl)-2'-O-Acetal levuliny ester uridine (9a)

$^1$H NMR (400 MHz, DMSO-d6): δ 11.39 (s, 1H), 7.62 (d, 1H, J=8.4), 5.56 (s, 1H), 5.52 (d, 1H, J=8), 5.38, 5.36 (abq, 1H each, J=6.4, 6.4), 4.41 (d, 1H, J=4.8), 4.30-4.26 (m, 1H), 4.15 (H, J=12.4), 3.31-3.88 (m, 2H), 2.71-2.69 (m, 2H), 2.48-2.46 (m, 2H), 2.08 (s, 3H), 1.03-0.93 (m, 28H). $^{13}$C NMR (125 MHz, DMSO-c/6): 172.6, 164.0, 150.7, 140.5, 101.8, 90.0, 88.2, 82.5, 80.6, 68.8, 60.4, 37.9, 30.2, 28.4, 18.0, 17.9, 17.8, 17.7, 17.6, 17.55, 17.5, 17.4, 13.4, 13.0, 12.9, 12.6. ESI-TOF calc for $C_{27}H_{46}N_2O_{10}Si_2$ 637.27 (+Na$^+$). found 637.26.

N4-levulinyl-3',5'-O-(1,1,3,3-tetraisopropyldisiloxane-1,3-diyl)-2'-O-acetal levuliny ester cytidine (9b)

$^1$H NMR (400 MHz, DMSO-c/6): δ 10.98 (s, 1H), 8.02 (d, 1H, J=7.6), 7.16 (d, 1H, J=7.2), 5.64 (s, 1H), 5.45 (s, 1H), 4.31 (d, 1H, J=4.8), 4.21-4.15 (m, 2H), 4.02 (d, 1H, J=10), 3.90 (d, 1H, 13.2), 2.72-2.69 (m, 4H), 2.58-2.55 (m, 2H), 2.51-2.48 (m, 2H), 2.09 (s, 3H), 2.08 (s, 3H), 1.04-0.95 (m, 28H). $^{13}$C NMR (125 MHz, DMSO-d6): 207.8, 207.4, 173.7, 172.5, 163.1, 154.8, 144.2, 95.8, 90.2, 87.9, 81.7, 80.7, 70.6, 68.0, 37.7, 31.0, 30.3, 30.2, 28.4, 18.0, 17.9, 17.8, 17.7, 17.6, 17.5, 17.4, 13.2, 13.0, 12.6. ESI-TOF calc for $C_{32}H_{53}N_3O_{11}Si_2$ 734.32 (+Na$^+$). found 734.30.

N6-(9-Fluorenylmethoxycarbonyl)-3',5'-O-(1,1,3,3-tetraisopropyldisiloxane-1,3-diyl)-2'-O-acetal levuliny ester adenosine (9c)

$^1$H NMR (400 MHz, CDCl$_3$): δ 8.71 (s, 1H), 8.52 (s, 1H), 8.27 (s, 1H), 7.76 (d, 2H, J=7.6), 7.63 (d, 2H, J=7.2), 7.42-7.38 (m, 2H), 7.32-7.26 (m, 4H), 6.04 (s, 1H), 5.58, 5.40 (abq, 1H each, J=6.4, 6.4), 4.95-4.91 (m, 1H), 4.67 (d, 1H, J=4.4), 4.62 (d, 1H, J=6.8), 4.34-4.31 (t, 1H, J=6.8), 4.19, 3.99 (abq, 1H each, J=13.6, 13.2), 4.10 (d, 1H, J=9.2), 2.74-2.71 (m, 2H), 2.58-2.55 (m, 2H), 2.10 (s, 3H), 1.09-1.00 (m, 28H). $^{13}$C NMR (125 MHz, CDCl$_3$): δ 206.6, 172.6, 152.9, 151.2, 150.6, 149.5, 143.7, 142.0, 141.6, 120.0, 127.4, 125.3, 122.9, 120.3, 89.1, 88.6, 81.6, 81.4, 77.5, 77.15, 77.0, 76.9, 69.5, 68.0, 60.0, 47.1, 37.9, 30.0, 28.2, 17.7, 17.5, 17.4, 17.3, 17.2, 17.1, 13.6, 13.2, 13.0, 12.9. ESI-TOF calc for $C_{43}H_{57}N_5O_{10}Si_2$ 882.36 (+Na$^+$). found 882.34.

General Procedure for the Preparation of 3',5'-O-(1,1,3,3-tetraisopropyldisiloxane-1,3-diyl)-2'-O-acetal levulinyl ester nucleosides (9d, 9e, 9g, 9f, 9h)

N2-(9-Fluorenylmethoxycarbony)-3',5'-O-(1,1,3,3-tetraisopropyldisiloxane-1,3-diyl)-2'-O-acetal levulinyl ester guanosine (9d)

In flask A, compound 8d (9.5 mmol) is freeze dried in dry benzene. It is then dissolved in 95 mL DCM under a dry nitrogen environment and is cooled to 0° C. 9.5 mL of a freshly prepared 1 mol/L solution of sulphuryl chloride is then added dropwise over 15 minutes. This is immediately followed by the addition of 10.45 mol 4-Cl-styrene. This reagent is used to quench the chloromethylether by-product. The reaction is stirred for an additional 30 minutes and then warmed to room temperature. It is then stirred for an additional 30 minutes. In flask B, cesium carbonate (14.25 mmol) is suspended in 20 mL of dry DMF followed by the addition of levulinic acid (28.5 mmol). The reaction mixture is refluxed for 2 hr and then cooled to room temperature. Flask A is then canulated into flask B. The reaction mixture is then stirred for 2 hours. Upon completion of the reaction, the solution is then washed 3×100 mL of 5% NaHCO$_3$. The aqueous layer is then washed with 3×100 mL of DCM. The organic extracts are pooled and dried over MgSO$_4$. After filtration, the solvent is removed under reduced pressure to give reddish gew. This crude material is then purified by column chromatography 2% MeOH in DCM giving 9d as a white foam in 85% yield. Spectroscopic and mass spectral data of compound 9d: $^1$H NMR (400 MHz, CDCl$_3$) δ 10.53 (s, 1H), 9.43 (s, 1H), 8.02 (s, 1H), 7.78 (d, J=7.5, 2H), 7.67-7.53 (m, 2H), 7.42 (t, J=7.5, 2H), 7.34 (t, J=7.4, 2H), 6.05 (s, 1H), 5.54, 5.43 (abq, 2H, J=6.4, 6.41), 4.72-4.58 (m, 2H), 4.51 (dd, J=4.6, 9.2, 1H), 4.40 (d, J=4.6, 1H), 4.34 (t, J=6.5, 1H), 4.20, 4.00 (d, 1H each, J=13.1, 13.3), 4.12 (d, J=9.2, 1H), 2.63-2.59 (m, 2H), 2.50-2.45 (m, 2H), 2.06 (s, 3H), 1.20-0.86 (m, 28H). $^{13}$C NMR (125 MHz, CDCl$_3$): δ 209.2, 172.6, 155.9, 154.2, 147.7, 147.3, 143.2, 141.6, 128.3, 127.5, 125.0, 124.9, 121.7, 120.3, 88.37, 88.2, 81.5, 81.1, 69.1, 67.9, 59.8, 47.0, 30.3, 28.5, 17.7, 17.5, 17.4, 17.3, 17.2, 13.6, 13.2, 12.8. ESI-TOF calc for $C_{43}H_{57}N_5O_{11}Si_2$ 898.36 (+Na$^+$). found 898.46.

3'5'4)-(1,1,3,3-tetraisopropyldisiloxane-1,3-diyl)-2'-O-acetal levulinyl ester adenosine (9e)

Dissolve 5.4 mmol of 9c in 60 mL of a dry solution of 2:3 triethylamine/pyridine. Stir the reaction at room temperature until completion, approximately 8 hr. When the reaction is finished, evaporate to dryness and perform flash chromatography in a gradient of 0→4% MeOH in DCM. The final product, 9e will appear as a white foam, >99% yield. Spectroscopic and mass spectral data of compound 9e: $^1$H NMR (500 MHz, CDCl$_3$) δ 8.28 (s, 1H), 8.08 (s, 1H), 7.26 (s, 1H), 6.01 (s, 1H), 5.65-5.660 (m, 2H), 5.41 (d, J=6.5, 1H), 4.92 (dd, J=4.8, 9.3, 1H), 4.66 (d, J=4.8, 1H), 4.19 (d, J=13.2, 1H), 4.09 (d, J=9.3, 1H), 4.01 (dd, J=2.5, 13.2, 1H), 2.78-2.71 (m, 2H), 2.63-2.57 (m, 2H), 2.14 (s, 3H), 1.04 (m, 28H). $^{13}$C NMR (125 MHz, CDCl$_3$) δ 206.58, 172.58, 155.51, 153.24, 153.19, 149.43, 139.72, 120.63, 88.95, 88.69, 81.52, 81.48, 69.48, 60.18, 37.94, 29.99, 28.20, 17.67, 17.57, 17.53, 17.44, 17.32, 17.27, 17.15, 13.60, 13.18, 13.01, 12.88. ESI-TOF calc for $C_{23}H_{47}N_5O_3Si_2$ 660.30 (+Na$^+$). found 660.32.

3',5'-O-(1,1,3,3-tetraisopropyldisiloxane-1,3-diyl)-2'-O-acetal levulinyl ester guanosine (9g)

Dissolve 6 mmol of 9d in 65 mL of a dry solution of 2:3 triethylamine/pyridine. Stir the reaction at room temperature until completion, approximately 8 hr. When the reaction is finished, evaporate to dryness and perform flash chromatography in a gradient of 0→5% MeOH in DCM. The final product, 9g will appear as a white foam, >99% yield. Spectroscopic and mass spectral data of compound 9g: $^1$H NMR (500 MHz, CDCl3) δ 12.07 (s, 1H), 7.82 (s, 1), 6.22 (s, 2H), 5.89 (s, 1H), 5.68, 5.44 (abq, 1H each, J=6.4, 5.44), 4.62-4.50 (m, 1H), 4.50-4.40 (m, 1H), 4.27-4.16 (m, 1H), 4.10 (d, J=9.1, 1H), 4.02-3.95 (m, 1H), 2.85-2.48 (m, 4H), 2.17 (s, 3H), 1.20-0.83 (m, 28H). $^{13}$C NMR (125 MHz, CDCl3) δ 207.11, 172.68, 159.52, 153.83, 151.12, 89.06, 88.31, 81.54, 81.47, 68.93, 60.01, 37.82, 30.12, 28.27, 17.74, 17.69, 17.56, 17.53, 17.51, 17.42, 17.36, 17.30, 17.25, 17.11, 13.66, 13.16, 13.08, 12.76. ESI-TOF calc for $C_{23}H_{47}N_5O_9Si_2$ 676.29 (+Na$^+$). found 676.46.

N6-levulinyl-3',5'-O-(1,1,3,3-tetraisopropyldisiloxane-1,3-diyl)-2'-O-acetal levulinyl ester adenosine (9f). Dissolve 5.4 mmol of 9e in 60 mL of THF. Add 21.4 mmol of EEDQ followed by the addition of 27 mmol levulinic acid. Stir the reaction mixture at room temperature for 1 hr then heat at 60° C. for 5 hours. When the reaction is complete, quench it with 20 mL of 5% NaHCO$_3$ and dilute the reaction mixture with 200 mL of ethyl acetate. Wash the organic layer 3×50 mL 5% NaHCO$_3$. Dry the organic layer with MgSO$_4$, filter and evaporate. Purify the reaction mixture by column chromatography, 0→3% MeOH in DCM. The product 9f is obtained as a white foam, 86% yield in addition to a small N6-bislevulinylated impurity that is inseparable by column chromatography at this stage. Spectroscopic and mass spectral data of compound 9f: $^1$H NMR (500 MHz, CDCl$_3$) δ 8.79 (s, 1H), 8.35 (s, 1H), 7.83 (s, 1H), 5.72 (d, J=7.5, 2H), 5.06 (d, J=6.4, 1H), 4.71-4.65 (m, 1H), 4.30 (d, J=4.3, 1H), 4.06 (s, 1H), 3.66 (d, J=12.7, 2H), 3.46 (d, J=11.8, 1H), 3.14 (s, 1H), 2.93-2.83 (m, 2H), 2.63-2.55 (m, 3H), 2.49-243 (m, 1H), 2.42-2.37 (m, 1H), 2.10-2.02 (m, 2H), 1.92 (s, 3H), 1.86 (s, 3H). $^{13}$C NMR (125 MHz, DMSO) δ 207.75, 207.39, 173.68, 172.53, 163.06, 154.81, 144.22, 95.77, 90.23, 87.88, 81.72, 80.64, 67.99, 60.11, 37.87, 37.65, 30.98, 30.23, 30.20, 28.40, 17.99, 17.87, 17.82, 17.74, 17.59, 17.51, 17.42, 13.28, 13.01, 12.97, 12.56. ESI-TOF calc for C$_{33}$H$_{53}$N$_5$O$_{10}$Si$_2$ 758.33 (+Na$^+$). found 758.32.

N2-dimethylformamidine-3',5'-O-(1,1,3,3-tetraisopropyldisiloxane-1,3-diyl)-2'-O-acetal levulinyl ester guanosine (9h)

Dissolve 1.9 mmol of 9g in 20 mL of THF. Add 7.6 mmol of dimethylformamidine dimethylacetal to the stirring reaction and stir overnight at room temperature. Evaporate the reaction mixture to dryness and purify by column chromatography, 0→5% MeOH in CHCl$_3$, the final product, 9h, is obtained as a white foam >99%.

Spectroscopic and mass spectral data of compound 9h. $^1$H NMR (500 MHz, CDCl$_3$) δ 9.01 (s, 1H), 8.60 (s, 1H), 7.87 (s, 1H), 5.99 (s, 1H), 5.62, 5.54 (abq, 1H each, J=4.1, 4.0), 4.51 (s, 1H), 4.38 (s, 1H), 4.28-4.16 (m, 1H), 4.11 (d, 1H, J=9.2), 4.04-3.93 (m, 1H), 3.20 (s, 3H), 3.10 (s, 3H), 2.75-3.60 (m, 2H), 2.57-2.43 (m, 2H), 2.12 (s, J=1.9, 3H), 1.26-0.81 (m, 28H). $^{13}$C NMR (125 MHz, CDCl$_3$) δ 206.35, 206.31, 172.38, 158.42, 157.92, 157.12, 149.49, 135.60, 135.54, 121.07, 88.52, 87.63, 81.56, 81.44, 69.04, 59.99, 41.58, 37.86, 35.43, 35.36, 29.95, 28.18, 17.69, 17.54, 17.50, 17.36, 17.26, 17.10, 13.67, 13.17, 13.14, 12.75. ESI-TOF calc for C$_{31}$H$_{52}$N$_6$O$_9$Si$_2$ 731.33 (+Na$^+$). found 731.38.

Synthesis of 2'-O-Acetal Levulinyl Ester Uridine (10a)

Compound 9a (10.1 mmol) is dissolved in 30 mL dry THF and stirred under nitrogen atmosphere. NEt$_3$:3HF (15.1 mmol) is added dropwise and the reaction is monitored by TLC (5% MeOH in CH$_2$Cl$_2$). After 2 hrs, 10a precipitates as a white solid. It is filtered off and washed with 100 mL of ether and dried under high vacuum in near quantitative yield. Compounds 10b, 10f and 10h were prepared in a similar manner.

Spectroscopic and Mass Spectral Data of Compounds 10a, 10b and 10f and 10h.

2'-O-Acetal Levulinyl Ester Uridine (10a)

$^1$H NMR (500 MHz, DMSO-d6): δ 11.34 (s, 1H), 7.88 (d, 1H, J=8), 5.84 (d, 1H, J=5), 5.64 (d, 1H, J=8.5), 5.30 (d, 1H, J=6), 5.28 (d, 1H, J=10.5), 5.21 (d, 1H, J=7), 5.13 (t, 1H, J=5), 4.21 (t, 1H, J=5.5), 4.10 (t, J=5.5), 3.83-3.82 (m, 1H), 3.63-3.30 (m, 2H), 2.67 (t, 2H, J=6), 2.43 (t, 2H, J=6), 2.08 (s, 3H). $^{13}$CNMR (125 MHz, DMSO-d6): δ 207.3, 172.5, 163.8, 151.3, 141.2, 102.6, 88.5, 86.9, 85.6, 81.4, 69.3, 61.2, 37.9, 30.2, 28.4. ESI-TOF calc for C$_{15}$H$_{20}$N$_2$O$_9$ 395.12 (+Na$^+$). found 395.23.

N4-Levulinyl-2'-O-Acetal Levulinyl Ester Cytidine (10b)

$^1$H NMR (400 MHz, DMSO) δ 10.96 (s, 1H), 8.38 (d, 1H, J=7.6), 7.15 (d, 1H, J=9.5), 5.81 (s, 1H), 5.38 (d, 1H, J=6.4), 5.31 (d, 1H, J=8), 5.25 (d, 1H, J=6), 5.20 (s, 1H), 4.16 (s, 1H), 4.07 (d, 1H, J=4.8), 3.86 (s, 1H), 3.75-3.72 (m, 1H), 3.60-3.56 (m, 1H), 2.71-2.44 (m, 8H), 2.09 (s, 3H), 2.08 (s, 3H). $^{13}$C NMR (125 MHz, DMSO) δ 207.68, 207.4, 173.8, 172.5, 163.1, 155.2, 145.8, 96.0, 89.2, 88.4, 84.9, 82.1, 68.2, 60.2, 37.9, 37.7, 31.1, 30.3, 28.4. ESI-TOF calc for C$_{20}$H$_{27}$N$_3$O$_{10}$ 492.17 (+Na$^+$). found 492.20.

N6-levulinyl-2'-O-acet_al Levulinyl Ester Adenosine (10f)

$^1$H NMR (500 MHz, CDCl3) δ 8.79 (s, 1H), 8.35 (s, 1H), 7.83 (s, 1H), 5.72 (d, J=7.5, 2H), 5.06 (d, J=6.4, 1 H), 4.71-4.64 (m, 2H), 4.30 (d, J=4.3. 1H), 4.06 (s, 1H), 3.71-3.62 (m, 1H), 3.51-3.45 (m, 1H), 3.14 (s, 1H), 2.92-2.82 (m, 1H), 2.63-2.56 (m, 1H), 2.53-2.43 (m, 2H), 2.42-2.34 (m, 2H), 2.14-1.99 (m, 4H), 1.92 (s, 3H), 1.86 (s, 3H). $^{13}$C NMR (125 MHz, CDCl3) δ 207.7, 207.6, 207.5, 207.5, 172.2, 172.1, 152.1, 150.2, 150.1, 143.7, 123.5, 89.2, 88.22, 82.9, 72.2, 63.3, 54.0, 38.0, 37.9, 32.2, 30.2, 29.8, 29.4, 27.9. ESI-TOF calc for C$_{21}$H$_{27}$N$_5$O$_9$ 516.18 (+Na$^+$). found 516.27.

N2-dimethylformamidine-2'-O-acetal levulinyl ester guanosine (10h)

$^1$H NMR (500 MHz, DMSO) δ 11.46 (s, 1H), 8.54 (s, 1H), 8.15 (s, 1H), 5.92 (d, J=5.6, 1 H), 5.29 (d, J=6.3, 1H), 5.23 (d, J=6.5, 1H), 4.77-4.66 (m, 1H), 4.29 (s, 1H), 3.91 (s, 1H), 3.74-3.46 (m, 2H), 3.15 (s, 3H), 3.03 (s, 3H), 2.57 (t, J=6.5, 3H), 2.28 (t, 2H, J=6.2), 2.04 (s, 3H). $^{13}$C NMR (125 MHz, DMSO) δ 207.3, 172.4, 158.8, 158.1, 157.9, 150.43 137.5, 119.7, 88.5, 86.4, 85.7, 81.5, 69.7, 61.7, 41.4, 37.7, 35.4, 30.1, 28.2. ESI-TOF calc for C$_{21}$H$_{27}$N$_5$O$_9$ 489.45 (+Na$^+$). found 489.25.

General procedure for the preparation of 5'-O-(4,4'-dimethoxytrityl)-2'-O-acetal levulinyl ester ribonucleosides (11a,b,f,h)

As an example, the synthesis of 5'-O-(4,4'-dimethoxytrityl)-2'-O-acetal levulinyl ester uridine (11a) is provided. Compound 10a (7.3 mmol) is dissolved 10 mL of pyridine under a nitrogen atmosphere followed by the addition of DMTrCl (8.8 mmol). The reaction is stirred at room temperature until the reaction is complete, 3 h. The reaction is then quenched with 2 mL of 5% NaHCO$_3$ and the reaction is concentrated under vacuum. It is then redissolved in 50 mL DCM and washed with 25 mL of 5% NaHCO$_3$. The aqueous layer is then washed 2×50 mL DCM. The organic extracts are combined and dried over MgSO$_4$ and filtered. The solvent is removed by evaporation and the material is purified by column chromatography 0→3% MeOH in DCM. The final product 11a, appears as a white foam, 90% yield.

TABLE 2

Column chromatography and yields of compounds 11b, 11f, 11h.

| Compound | mmol (starting) | Column conditions | Yield |
|---|---|---|---|
| 11b | 3.5 | 0→2% MeOH in DCM (0.5% TEA) | 82 |
| 11f | 8 | 0→2% MeOH in DCM (0.5% TEA) | 85 |
| 11h | 5 | 0→3% MeOH in DCM (0.5% TEA) | 78 |

Spectroscopic and Mass Spectral Data of 11a,b,f,h.

5'-O-(4,4'-dimethoxytrity)-2'-O-acetal levulinyl ester uridine (11a)

$^1$H NMR (500 MHz, DMSO) δ 11.39 (s, 1H), 7.69 (d, J=8.1, 1H), 7.36 (d, 2H, J=7.3), 7.30 (t, 2H, J=7.6), 7.23 (dd, J=2.4, 9.0, 5H), 6.88 (d, J=8.9, 4H), 5.79 (d, J=3.7, 1H), 5.43-5.33 (m, 2H), 5.31 (d, J=8.1, 1H), 5.26 (d, J=6.5, 1H), 4.34-4.26 (m, 1H), 4.26-4.19 (m, 1H), 3.94 (S$_1$ 1H), 3.72 (s, 6H), 3.29-3.16 (m, 2H), 2.68 (t, 2H, J=6.6), 2.45 (t, 2H, J=6.5), 2.06 (s, 3H). $^{13}$C NMR (125 MHz, DMSO) δ 207.3, 172.5, 163.6, 158.8, 151.0, 145.3, 141.2, 136.0, 135.7, 130.4, 128.6, 128.5, 128.4, 127.4, 102.2, 88.6, 88.2, 86.5, 83.2, 81.2, 69.2, 67.7, 63.4, 55.7, 37.9, 30.1, 28.3, 25.8. ESI-TOF calc for $C_{36}H_{38}N_2O_{11}$ 697.25 (+Na$^+$). found 697.13.

N4-levulinyl-5'-O-(4,4'-dimethoxytrityl)-2'-O-acetal levulinyl ester cytidine (11b)

$^1$H NMR (400 MHz, DMSO) δ 10.97, 8.24 (d, 1H, J=8), 7.37 (d, 2H, J=8.4), 7.31 (t, 2H, J=7.6), 7.24-7.20 (m, 5H), 6.96 (d, 1H, J=7.6), 6.88-6.86 (m, 4H), 5.79 (s, 1H), 5.43-5.41 (m, 1H), 5.36-5.33 (m, 2H), 4.30-4.26 (m, 1H), 4.18 (d, 1H, J=5.2), 3.99 (d, 1H, J=8), 3.72 (s, 6H), 3.32 (s, 2H), 2.70-2.68 (m, 4H), 2.58-2.56 (m, 2H), 2.41-2.39 (m, 2H), 2.09 (s, 3H), 2.08 (s, 1H). $^{13}$C NMR (125 MHz, DMSO) δ 207.6, 207.4, 173.7, 172.5, 163.0, 158.8, 154.94, 145.2, 136.2, 135.8, 130.4, 130.3, 128.6, 128.4, 127.5, 113.9, 96.0, 90.0, 89.9, 88.4, 88.3, 88.2, 86.6, 82.5, 81.9, 81.8, 68.3, 62.3, 62.2, 55.8, 55.7, 55.6, 55.5, 37.9, 37.6, 31.0, 30.2, 30.1, 28.4. ESI-TOF calc for $C_{41}H_{45}N_3O_{12}$ 794.30 (+Na$^+$). found 794.21.

N6-levulinyl-5'-O-(4,4'-dimethoxytrityl)-2'-O-acetal levulinyl ester adenosine (11f)

$^1$H NMR (500 MHz, CH$_2$Cl$_3$) δ 8.97 (s, 1H), 8.57 (s, 1H), 8.20 (s, 1H), 7.41 (d, 2H J=8), 7.31-7.30 (m, 7H), 6.80-6.79 (m, 4H), 6.18 (d, 1H, J=4.5), 5.42, 5.34 (abq, 1H each, J=6, 6), 5.23 (s, 1H), 5.07 (t, 1H, 5), 4.61-5.06 (m, 1H), 4.27-4.24 (m, 1H), 3.77 (s, 6H), 3.52-3.49 (m, 1H), 3.43-3.40 (m, 1H), 3.19-3.16 (m, 2H), 2.99 (d, 1H, J=5.5), 2.91-2.88 (m, 2H), 2.76-2.71 (m, 2H), 2.47-2.23 (m, 2H), 2.30 (s, 3H), 2.15 (s, 3H). $^{13}$C NMR (75 MHz, CD3CN) δ 207.51, 207.27, 172.34, 158.89, 145.21, 136.01, 130.25, 128.23, 128.05, 113.23, 88.73, 86.38, 84.12, 63.40, 55.18, 55.09, 37.51, 37.46, 31.47, 28.96, 27.88. ESI-TOF calc for $C_{42}H_{45}N_5O_{11}$ 818.31 (+Na$^+$). found 818.29.

N2-dimethylformamidine-5'-O-(4,4'-dimethoxytrityl)-2'-O-acetal levulinyl ester guanosine (11h)

$^1$H NMR (500 MHz, CD$_3$CN) δ 9.83 (s, 1H), 8.55 (s, 1H), 7.77 (s, 1H), 7.42 (d, J=7.7, 2H), 7.36-7.08 (m, 7H), 6.94-6.68 (m, 4H), 6.01 (d, J=4.6, 1H), 5.43, 5.31 (abq, 1H each, J=6.5, 6.6), 4.88 (t, J=4.8, 1H), 4.61-4.55 (m, 1H), 4.10 (s, 1H), 3.76 (s, 6H), 3.41-3.20 (m, 2H), 3.08 (s, 3H), 3.05 (s, 3H), 2.72-2.51 (m, 2H), 2.45-2.29 (m, 2H), 2.06 (s, 3H). $^{13}$C NMR (125 MHz, CD$_3$CN) δ 207.2, 172.4, 158.9, 158.6, 158.0, 157.7, 150.6, 145.2, 136.9, 136.0, 130.2, 130.1, 128.2, 128.1, 127.1, 120.5, 117.5, 113.2, 88.6, 86.4, 86.3, 83.7, 81.6, 70.1, 63.7, 55.1, 40.9, 37.4, 34.5, 29.0, 28.9, 27.9. ESI-TOF calc for $C_{40}H_{44}N_6O_{10}$ 791.31 (+Na$^+$). found 791.35.

General Procedure for the Preparation of 5'-O-2-(2-nitrophenyl)propoxycarbonyl-2'-O-acetal levulinyl ester nucleosides (12a,b,f,h)

The synthesis of 5'-O-2-(2-nitrophenyl)propoxycarbonyl-2'-O-acetal levulinyl ester uridine 12a is provided as an example. Compound 10a (7.3 mmol) is dissolved in 10 mL of THF followed by 10 mL of pyridine under a dry nitrogen atmosphere and the reaction mixture is cooled to 0° C. 2-(2-nitrophenyl)propoxylchloroformate (8.8 mmol) in 5 mL of pyridine is added dropwise to the stirred reaction and the reaction is monitored by TLC (ethyl acetate). After 3 hrs the reaction is complete. The reaction mixture is quenched with 5 mL of water and the solvent is removed under reduced pressure. The remaining residue is dissolved in 150 mL of DCM and washed with 50 mL of 5% NaHCO$_3$. The aqueous layer is washed 3× with 50 mL DCM. The organic extracts are pooled and dried over magnesium sulphate. After filtration, the solvent is removed under reduced pressure giving a yellowish foam. This crude material is purified by flash chromatography in a gradient of 3:2 ethyl acetate/hexanes→ethyl acetate. The final diasteriomeric mixture of 12a is obtained as a yellow foam in 65% yield.

TABLE 3

Column chromatography and yields of compounds 12b, 12f, 12h.

| Compound | mmol (starting) | Column conditions | Yield |
|---|---|---|---|
| 12b | 8 | 0→2% MeOH in DCM | 52 |
| 12f | 2.8 | 80:20 EtOAc/hexanes | 45 |
| 12h | 1.5 | 80:20 DCM/acetone | 30 |

Spectroscopic and Mass Spectral Data of Compounds 12b, 12f, 12h.

5'-O-2-(2-nitrophenyl)propoxycarbonyl-2'-O-acetal levulinyl ester uridine (12a)

$^1$H NMR (500 MHz, DMSO-d6) δ 5.82 (d, H-1'), 5.76 (d, H-T), 4.34-4.23 (m, 2'-OOCH$_2$—O—×2), 2.68-2.65 (2'-CH$_2$—C(O)), 2.63-2.61 (2'-CH$_2$—C(O)), 2.43-2.40 (m, 2'-O—C(O)—CH$_2$—), 2.36-2.33 (m, 2'-O—C(O)—CH$_2$—), 2.06 (s, 2'-C(O)—CH$_3$×2). ESI-TOF calc for $C_{25}H_{29}N_3O_{13}$ 602.17 (+Na$^+$). found 602.16.

N4-levulirtyl-5'-O-2-(2-nitrophenyl)propoxycarbonyl-2'-O-acetal levulinyl ester cytidine (12b)

$^1$H NMR (500 MHz, DMSO-d6): δ 5.88 (d, H-11, 5.77 (d, H-1'), 5.19-5.01 (m, 2'-O—CH$_2$—O—×2), 2.72-2.66 (m, N4-CH$_2$—C(O)—×2, 2'-CH$_2$—C(O)×2), 2.56-2.32 (m,

N4-C(O)—CH$_2$—×2, 2'-O—C(O)—CH$_2$—×2), 2.10-2.05 (m, 2'-C(O)—CH$_3$×2, N4-C(O)—CH$_3$×2). C$_{30}$H$_{36}$N$_4$O$_{14}$ 699.22 (+Na$^+$). found 699.2.

N6-levulinyl-5'-O-(2-nitrophenyl)propoxycarbonyl-2'-O-acetal levulinyl ester adenosine (12f)

$^1$H NMR (500 MHz, CDCl$_3$): δ 6.24-6.19 (m, H-1$^1$×2), 5.19-5.01 (m, 2'-O—CH$_2$—O—×2), 2.82-2.57 (m, N6-CH$_2$—C(O)—×2, 2'-CH$_2$—C(O)×2, N6-C(O)—CH$_2$—×2, 2'-O—C(O)—CH$_2$—×2), 2.20-1.80 (m, 2'-C(O)—CH$_3$×2, N4-C(O)—CH$_3$×2). C$_{31}$H$_{36}$N$_6$O$_{13}$ 723.23 (+Na$^+$). found 723.29.

N2-dimethylformamidine-5'-O-(2-nitrophenyl)propoxycarbonyl-2'-O-acetal levulinyl ester guanosine (12h)

$^1$H NMR (500 MHz, CDCl$_3$): δ 6.15-6.11 (m, H-1$^1$×2), 5.41 (d, 2'-O—CH—O—, J=6.5), 5.10-5.06 (m, 2'-O—CH$_2$—O—), 5.02 (d, Z—O—CH—O—, J=6.5), 2.82-2.79 (m, 2'-CH—C(O)×2), 2.69-2.63 (m, 2'-CH—C(O)×2) 2.44-2.34 (m, 2'-O—C(O)—CH$_2$—×2), 2.18 (s, 2'-C(O)—CH$_3$×2). C$_{29}$H$_{35}$N$_2$O$_{12}$ 696.23 (+Na$^+$). found 696.30.

General procedure for the preparation of 5'-O-(4,4'-dimethoxytrityl)-2'-O-acetal levulinyl ester 3'-O-2-cyanoethyl N,N-diisopropyl)phosphoramidites (13a, b,f,h)

The synthesis of 5'-O-(4,4'-dimethoxytrityl)-2'-O-acetal levulinyl ester uridine-3'-O-2-cyanoethyl N,N-diisopropyl) phosphoramidite (13a) is provided as an example. Compound 11a (5 mmol) is dissolved in 20 mL of dry THF under a dry nitrogen environment. Diisopropylethylamine (21 mmol) is then added followed by the dropwise addition of 2-cyanoethyl N,N-diisopropylchlorophosphoramidite (6 mmol). The reaction was monitored by TLC (5% MeOH in DCM) and was complete after 2 hrs. The reaction mixture was then diluted with 200 mL of DCM and washed once with 40 mL 5% NaHCO$_3$. The aqueous mixture was extracted 3× with 50 mL DCM. The pooled extracts were dried over MgSO$_4$ and filtered and evaporated under reduced pressure. This crude material was then purified on a short column neutralized with 0.5% triethylamine using a gradient of 6:4 ethyl acetate/hexanes (0.5% triethylamine)→7:3 ethyl acetate/hexanes (0.5% triethylamine). The final product, 13a is obtained as a white foam in 90% yield.

Characterization of Compounds 13a, 13b, 13f and 13h.

5'-O-(4,4'-dimethoxytrityl)-2'-O-acetal levulinyl ester uridine-3'-O-2-cyanoethyl N,N-diisopropyl) phosphoramidite (13a)

$^{31}$P NMR (80 MHz, CD$_3$CN): δ 151.24, 149.88. ESI-TOF calc for C$_{45}$H$_{55}$N$_4$O$_{12}$P, 897.36 (+Na$^+$). found 897.41.

N4-levulinyl-5'-O-(4,4'-dimethoxytrityl)-2'-O-acetal levulinyl ester cytidine-3'-O-2-cyanoethyl N$_1$N-diisopropyl)phosphoramidite (13b)

$^{31}$P NMR (80 MHz, CD$_3$CN): δ 151.30, 149.26. ESI-TOF calc for C$_{60}$H$_{62}$N$_5$O$_{13}$P, 994.41 (+Na$^+$). found 994.38.

N6-levulinyl-5'-O-(4,4'-dimethoxytrityl)-2'-O-acetal levulinyl ester adenosine-3'-O-2-cyanoethyl N,N-diisopropyl)phosphoramidite (13f)

$^{31}$P NMR (80 MHz, CD$_3$CN): δ 151.05, 150.52. ESI-TOF calc for C$_{51}$H$_{62}$N$_7$O$_{12}$P, 1018.42 (+Na$^+$). found 1018.35.

N2-dimethylformamidine-5'-O-(4,4'-dimethoxytrityl)-2'-O-acetal levulinyl ester guanosine-3'-O-2-cyanoethyl N,N-diisopropyl)phosphoramidite (13h)

$^{31}$P NMR (80 MHz$_1$ CD$_3$CN): δ 151.5, 150.9. ESI-TOF calc for C$_{49}$H$_{61}$H$_8$O$_{11}$P, 1014.42 (+Na$^+$). found 1014.38.

General Procedure for the Preparation of 5'-O-2-(2-nitrophenyl)propoxycarbonyl-2'-O-acetal levulinyl ester 3'-O-2-cyanoethyl N,N-diisopropyl)phosphoramidites (14a,b,f,g)

The synthesis of 5'-O-2-(2-nitrophenyl)propoxycarbonyl-2'-O-acetal levulinyl ester uridine-3'-O-2-cyanoethyl N,N-diisopropyl)phosphoramidite (14a) is provided as an example. Compound 12a (2.67 mmol) is dissolved in 10 mL of dry THF under a dry nitrogen environment. Diisopropylethylamine (10.7 mmol) is then added followed by the dropwise addition of 2-cyarioethyl N,N-diisopropylchlorophosphoramidite (3.2 mmol). The reaction was monitored by TLC (ethyl acetate) and was complete after 2 hrs. The reaction mixture was then diluted with 150 mL of DCM and washed once with 25 mL 5% NaHCO$_3$. The aqueous mixture was extracted 3× with 25 mL DCM. The pooled extracts were dried over MgSO$_4$ and filtered and evaporated under reduced pressure. This crude material was then purified on a short column neutralized with 0.5% triethylamine using a gradient of 3:2 ethyl acetate/hexanes (0.5% triethylamine) →ethyl acetate (0.5% triethylamine). The final product, 14a is obtained as a yellowish foam in 88% yield.

TABLE 4

Column chromatography and yields of compounds 13b, 13f, 13h.

| Compound | mmol (starting) | Column conditions | Yield |
| --- | --- | --- | --- |
| 13b | 6 | 7:3 ethyl acetate/hexanes (0.5% TEA) | 84 |
| 13f | 2.5 | 0 → 90% EtOAc in hexanes (0.5% TEA) | 81 |
| 13h | 1.1 | 0 → 100% EtOAc in hexanes (0.5% TEA) | 70 |

TABLE 5

Column chromatography and yields of compounds 14b, 14f, 14h.

| Compound | mmol (starting) | Column conditions | Yield |
| --- | --- | --- | --- |
| 14b | 9 | 4:1 ethyl acetate/hexanes (0.5% TEA) | 85 |
| 14f | 1.5 | 80:20 EtOAc/hexanes→70:30 EtOAc/hexanes (0.5% TEA) | 86 |
| 14h | 0.8 | EtOAc (1% TEA) | 85 |

Characterization of Compounds 14a, 14b, 14f and 14h.

5'-O-2-(2-nitrophenyl)propoxycarbonyl-2'-O-acetal levulinyl ester uridine-3'-O-2-cyanoethyl N,N-diisopropyl)phosphoramidite (14a)

$^{31}$P NMR (80 MHz, CD$_3$CN): δ 151.30, 150.89, 150.17, 149.98. ESI-TOF calc for C$_{34}$H$_{46}$N$_5$O$_{14}$P, 802.28 (+Na$^+$). found 802.23.

N4-levulinyl-5'-O-2-(2-nitrophenyl)propoxycarbonyl-2'-O-acetal levulinyl ester cytidine-3'-O-2-cyanoethyl N,N-diisopropyl)phosphoramidite (14b)

$^{31}$P NMR (80 MHz, CD$_3$CN): δ 151.15, 150.32, 150.10, 149.79. ESI-TOF calc for C$_{34}$H$_{46}$N$_5$O$_{14}$P, 802.28 (+Na$^+$). found 802.23. ESI-TOF calc for C$_{39}$H$_{53}$N$_6$O$_{15}$P, 899.33 (+Na$^+$). found 899.31.

N6-levulinyl-5'-O-2-(2-nitrophenyl)propoxycarbonyl-2'-O-acetal levulinyl ester adenosine-3'-O-2-cyanoethyl N,N-diisopropyl)phosphoramidite (14f)

$^{31}$P NMR (80 MHz, CD$_3$CN): δ 151.64, 151.41, 151.25, 151.03. ESI-TOF calc for C$_{40}$H$_{53}$N$_8$O$_{14}$P, 923.34 (+Na$^+$). found 923.31.

N2-dimethylformamidine-5'-O-2-(2-nitrophenyl)propoxycarbonyl-2'-O-acetal levulinyl ester guanosine-3'-O-2-cyanoethyl N,N-diisopropyl)phosphoramidite (14h)

$^{31}$P NMR (80 MHz, CD$_3$CN): δ 151.27, 151.06, 149.72, 149.59. ESI-TOF calc for C$_{40}$H$_{53}$N$_8$O$_{14}$P, 896.34 (+Na$^+$). found 896.37.

Characterization of Compounds 17-31 Prepared According to Scheme 2

N4-(9-Fluorenylmethoxycarbonyl)-3',5'-O-(1,1,3,3-tetraisopropyldisiloxane-1,3-diyl)-2'-O-(methylthio)methyl cytidine (17)

$^1$H NMR (500 MHz, CDCl$_3$): δ 5.92 (d, H-1'), 5.68 (d, 2'-O—CH—O—), 5.57 (d, 2'-O—CH—O), 2.10 (s, 2'-C(O)—CH$_3$). ESI-TOF calc for C$_{38}$H$_{53}$N$_3$O$_8$SSi$_2$ 780.31 (+Na$^+$). found (+Na$^+$).

N4-(9-Fluorenylmethoxycarbonyl)-3',5'-O-(1,1,3,3-tetraisopropyldisiloxane-1,3-diyl)-2'-O-acetal levulinylester cytidine (18)

$^1$H NMR (500 MHz, CDCl$_3$): δ 6.01 (d, H-1'), 5.33 (d, 2'-O—CH—O—), 4.99 (d, 2'-O—CH—O—), 2.79-2.74 (m, 2'-CH$_2$—C(O)), 2.71-2.65 (m, 2'-C(O)—CH$_2$—), 2.11 (s, 2'-C(O)—CH$_3$). ESI-TOF calc for C$_{42}$H$_{52}$N$_3$O$_{11}$Si$_2$ 858.35 (+Na$^+$). found 858.34 (+Na$^+$).

N6-(9-Fluorenylmethoxycarbonyl)-2'-O-acetal levulinyester adenosine (19)

$^1$H NMR (500 MHz, CDCl$_3$): δ 6.01 (d, H-1'), 5.35 (d, 2'-O—CH—O—), 4.95 (d, 2'-O—CH—O—), 2.80-2.76 (m, 2'-CH$_2$—C(O)), 2.70-2.66 (m, 2'-C(O)—CH$_2$—), 2.17 (s, 2'-C(O)—CH$_3$). ESI-TOF calc for C$_{31}$H$_{31}$N$_5$O$_9$ 640.21 (+Na$^+$). found 640.26 (+Na$^+$).

N2-(9-Fluorenylmethoxycarbonyl)-2'-O-acetal levulinyester guanosine (20)

$^1$H NMR (500 MHz, CDCl$_3$): δ 5.96 (d, H-1'), 5.44 (d, 2'-O—CH—O—), 5.36 (d, 2'-O—CH—O—), 2.78-2.72 (m, 2'-CH—C(O)), 2.63-2.57 (m, 2'-CH—C(O)), 2.46-2.40 (m, 2'-C(O)—CH—), 2.12 (s, 2'-C(O)—CH$_3$). ESI-TOF calc for C$_{31}$H$_{31}$N$_5$O$_{10}$ 656.21 (+Na$^+$). found 656.24 (+Na$^+$).

N4-(9-Fluorenylmethoxycarbonyl)-2'-O-acetal levulinyester cytidine (21)

$^1$H NMR (500 MHz, CDCl$_3$): δ 5.75 (d, H-1'), 5.60 (d, 2'-O—CH—O—), 5.44 (d, 2'-O—CH—O—), 2.81-2.78 (m, 2'-CH$_2$—C(O)), 2.56-2.54 (m, 2'-C(O)—CH$_2$—), 2.19 (s, 2'-C(O)—CH$_3$). ESI-TOF calc for C$_{31}$H$_{31}$N$_3$O$_{10}$ 616.20 (+Na$^+$). found 616.20 (+Na$^+$).

N6-5'-(4,4'-dimethoxytrityl)-2'-O-acetal levulinylester adenosine (22)

$^1$H NMR (500 MHz, CDCl$_3$): δ 6.20 (d, H-1'), 5.44 (d, 2'-O—CH—O—), 5.35 (d, 2'-O—CH—O—), 2.75-2.72 (m, 2'-CH$_2$—C(O)), 2.47-2.45 (m, 2'-C(O)—CH$_2$—), 2.15 (s, 2'-C(O)—CH$_3$). ESI-TOF calc for C$_{52}$H$_{49}$N$_5$O$_{11}$ 942.34 (+Na$^+$). found 942.30 (+Na$^+$).

N2-(4,4'-dimethoxytrityl)-2'-O-acetal levulinylester guanosine (23)

$^1$H NMR (500 MHz, CDCl$_3$): δ 5.99 (d, H-1'), 5.53 (d, 2'-O—CH—O—), 5.40 (d, 2'-O—CH—O—), 2.74-2.72 (m, 2'-CH$_2$—C(O)), 2.53-2.49 (m, 2'-C(O)—CH$_2$—), 2.12 (s, 2'-C(O)—CH$_3$). ESI-TOF calc for C$_{52}$H$_{44}$N$_4$O$_{12}$ 958.34 (+Na$^+$). found 958.29 (+Na$^+$).

N4-(4,4'-dimethoxytrityl)-2'-O-acetal levulinylester cytidine (24)

$^1$H NMR (500 MHz, CDCl$_3$): δ 5.92 (s, H-11, 5.67 (d, 2'-O—CH—O—), 5.57 (d, 2'-O—CH—O—), 2.79-2.75 (m, 2'-CH$_2$—C(O)), 2.58-2.55 (m, 2'-C(O)—CH$_2$—), 2.18 (s, 2'-C(O)—CH$_3$). ESI-TOF calc for C$_{51}$H$_{49}$N$_3$O$_{12}$ 918.29 (+Na$^+$). found 918.28 (+Na$^+$).

N6-(9-Fluorenylmethoxycarbonyl)-5'-O-2-(2-nitrophenyl)propoxycarbonyl-2'-O-acetal levulinylester adenosine (25)

$^1$H NMR (500 MHz, CDCl$_3$): δ 6.23-6.21 (m, H-1'×2), 5.44-5.35 (m, 2'-O—CH$_2$—O—×2), 2.77-2.75 (m, 2'-CH$_2$—C(O)×2), 2.48-2.46 (m, 2'-O—C(O)—CH$_2$—×2), 2.17 (s, 2'-C(O)—CH$_3$×2). ESI-TOF calc for C$_{41}$H$_{40}$N$_6$O$_{13}$ 847.27 (+Na$^+$). found 847.29 (+Na$^+$).

N2-(9-Fluorenylmethoxycarbonyl)-5'-O-2-(2-nitrophenyl)propoxycarbonyl-2'-O-acetal levulinylester guanosine (26)

$^1$H NMR (500 MHz, CDCl$_3$): δ 5.97 (s, H-1'×2), 5.50 (d, 2'-O—CH—O—), 5.45 (d, 2'-O—CH—O—), 5.38-5.36 (m, 2'-O—CH$_2$—O—), 2.75-2.68 (m, 2'-CH$_2$—C(O)×2), 2.54-2.45 (m, 2'-O—C(O)—CH$_2$—×2), 2.15 (s, 2'-C(O)—CH$_3$×2). ESI-TOF calc for C$_{31}$H$_{40}$N$_6$O$_{14}$ 863.23 (+Na$^+$). found 863.36 (+Na$^+$).

N6-(9-Fluorenylmethoxycarbonyl)-5'-O-(4, 4'-dimethoxytrityl)-2'-O-acetal levulinylester adenosine-3'-O-2-cyanoethyl N,N-diisopropyl)phosphoramidite (27)

ESI-TOF calc for $C_{61}H_{66}N_2O_{12}P$, 1142.41 (+Na$^+$). found 1142.44 (+Na$^+$); $^{31}$P NMR (80 MHz, CD$_3$CN): δ 151.16, 151.6.

N2-(9-Fluorenylmethoxycarbonyl)-5'-O-(4, 4'-dimethoxytrityl)-2'-O-acetal levulinylester guanosine-3'-O-2-cyanoethyl N,N-diisopropyl)phosphoramidite (28)

ESI-TOF calc for $C_{61}H_{66}N_2O_{13}P$, 1158.45 (+Na$^+$). found 1158.40 (+Na$^+$); $^{31}$P NMR (80 MHz, CD$_3$CN): δ 151.78, 150.59.

N2-(9-Fluorenylmethoxycarbonyl)-5'-O-(4, 4'-dimethoxytrityl)-2'-O-acetal levulinylester cytidine-3'-O-2-cyanoethyl N,N-diisopropyl)phosphoramidite (29)

ESI-TOF calc for $C_{60}H_{66}N_5O_{13}P$, 1118.44 (+Na$^+$). found 1118.38 (+Na$^+$); $^{31}$P NMR (80 MHz, CD$_3$CN): δ 151.88, 150.47.

N6-(9-Fluorenylmethoxycarbonyl)-5'-O-2-(2-nitrophenyl)propoxycarbonyl-2'-O-acetal levulinylester adenosine-3'-O-2-cyanoethyl N,N-diisopropyl)phosphoramidite (30)

ESI-TOF calc for $C_{50}H_{57}N_8O_{14}P$, 1047.37 (+Na$^+$). found 1047.51 (+Na$^+$); $^{31}$P NMR (80 MHz, CD$_3$CN): δ 151.01.

N2-(9-Fluorenylmethoxycarbonyl)-5'-O-2-(2-nitrophenyl)propoxycarbonyl-2'-O-acetal levulinylester guanosine-3'-O-2-cyanoethyl N,N-diisopropyl)phosphoramidite (31)

ESI-TOF calc for $C_{50}H_{57}N_8O_{15}P$, 1063.37 (+Na$^+$). found 1063.37 (+Na$^+$); $^{31}$P NMR (80 MHz, CD$_3$CN): δ 151.21, 151.06.

Example 2. Experimental Protocols for the Solid Phase Synthesis of RNA Strands Using 5'-DMTr-2'-ALE-3'-Phosphoramidite Monomers Synthesis A In this example, 1 μmol of the sequence 5'-GCU UGA AGU CUU UAA UUA Att-3' (SEQ ID NO: 1) was synthesized on an ABI 3400 using 5'-DMTr-2'-ALE-3'-phosphoramidite monomers 13a,b,f,g. The solid support used was Q-linked-dT CPG purchased from Glen Research. Standard oligoribonucleotide synthesis conditions were used with only one minute coupling times and 0.25 M DCI as an activator. Commercially available 2'-TBDMS and 2'-TOM monomers were also synthesized by standard conditions with one minute coupling times and 0.25 M DCI as an activator for comparison. These oligos were deprotected according to standard protocol. Upon completion of the 2'-ALE RNA synthesis, a portion of the material was first treated with 2:3 triethylamine/acetonitrile, 80 min, followed by treatment with 0.5 M hydrazine hydrate in 3:2 pyridine acetic acid for 60 min. The solid support bound fully deprotected oligo was then treated with 1 M TBAF for 24 hrs to cleave it from the CPG. In addition, another portion of the fully protected material was treated with 3:1 ammonium hydroxide/ethanol for 60 min at room temperature. The results are summarized in a PAGE gel and HPLC traces shown in FIGS. 4A and 4B, respectively, which show that the RNA strand synthesized from the ALE monomers is superior (overall yield) to those synthesized from TBDMS and TOM monomers.

Synthesis B

The solid-phase synthesis of r(GCUUGAAGUC-UUUAAUUAA)-d(TT) was performed on an ABI-3400 DNA/RNA synthesizer. A 1 μmol scale was conducted in the trityl-off mode using 500 A 5'-DMTr-dT-Q-linker long chain alkylamine controlled-pore glass (LCAA-CPG). The support was first subjected to a standard capping cycle, CAP A solution (Ac$_2$O/pyr/THF) and Cap B solution (10% 1-methylimidazole in THF) for 3×180 s to acetylate and dry the solid support. RNA synthesis was carried out using 0.1 M solutions of phosphoramidites 13a,b,f,g in dry ACN with 0.25 M DCI as the activator. All other ancillary agents necessary for oligonucleotide synthesis were obtained commercially. The detritylation step used 3% trichloroacetic acid (TCA) for 80 s. Each phosphoramidite coupling step was set for 1 min, or 10 min. The capping step (using CAP A and CAP B) was set for 20 s and the oxidization step using 0.1 M iodine/pyridine/water/THF was 30 s. 2'-O-TBDMS phosphoramidite monomers were used at 0.15 M concentration in acetonitrile (ACN) (Damha, M. J.; K. K. Ogilvie Protocols for Oligonucleotide Analogs, ed.; Humana: Totowa, N.J., 1993).

The RNA synthesized using 2'-O-TOM phosphoramidite monomers were obtained commercially and treated as above except a 0.10 M phosphoramidite concentration in acetonitrile was used, as recommended by Glen Research. Crude RNA synthesized from 2'-O-ACE chemistry was purchased from Dharmacon.

Deprotection of the 2'-O-TOM and 2'-O-TBDMS RNA oligomers from the CPG support was achieved with 29% aq. NH$_3$/ethanol; 3:1; 55° C., 30 min followed by 1 M TBAF in THF (16 h; r.t.). Deprotection of the ALE oligomer was carried out on-column as described above, except that the hydrazine treatment was extended to 4 h to achieve complete deprotection of the mixed sequence. Specifically, after completion of the synthetic cycle, the fully protected ALE oligomer was treated with anhydrous 2:3 v/v NEt$_3$/ACN (1 h; r.t.) through the column to deblock the cyanoethyl phosphate groups. The column was then washed thoroughly with ACN and dried under high vacuum. Next, the N-Lv/dmf and 2'-O-ALE groups were removed simultaneously by passing a solution of 0.5 M NH$_2$NH$_2$—H$_2$O in 3:2 v/v pyr:HOAc, 4 h, r.t. through the column. This was followed by washing the solid support with CH$_2$Cl$_2$ and ACN, and evacuation of trace solvents on high vacuum. At this stage, the naked RNA strand bound to the Q-CPG was transferred to a 1 mL eppendorf tube. The RNA was released from the Q-CPG support using fluoride treatment (1 mL of 1 M TBAF, 16 h, r.t.). The material was then centrifuged (14 000 rpm) and the supernatant was removed. The CPG was subsequently washed 4×250 μL with 1:1 water/ethanol. This material was evaporated to dryness and redissolved in water. It was then passed through a sephadex G-25 column to remove salts and purified further by denaturing polyacrylamide gel electrophoresis (24% acrylamide, 8.3 M urea).

Figure 5:
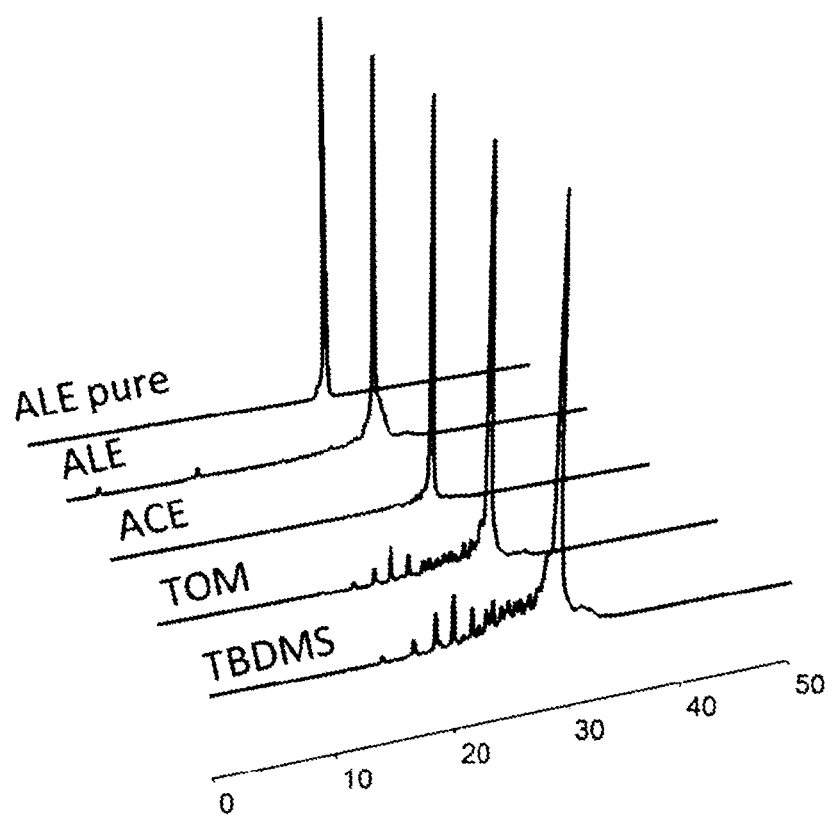
FIG. 5 show the anion exchange HPLC traces of crude antisense siRNA strands synthesized from 2'-O-TBDMS, 2'-O-TOM, 2'-O-ACE, and 2'-O-ALE chemistries. Purified oligomer from 2'-O-ALE chemistry is labeled "ALE pure".
Figure 6A:
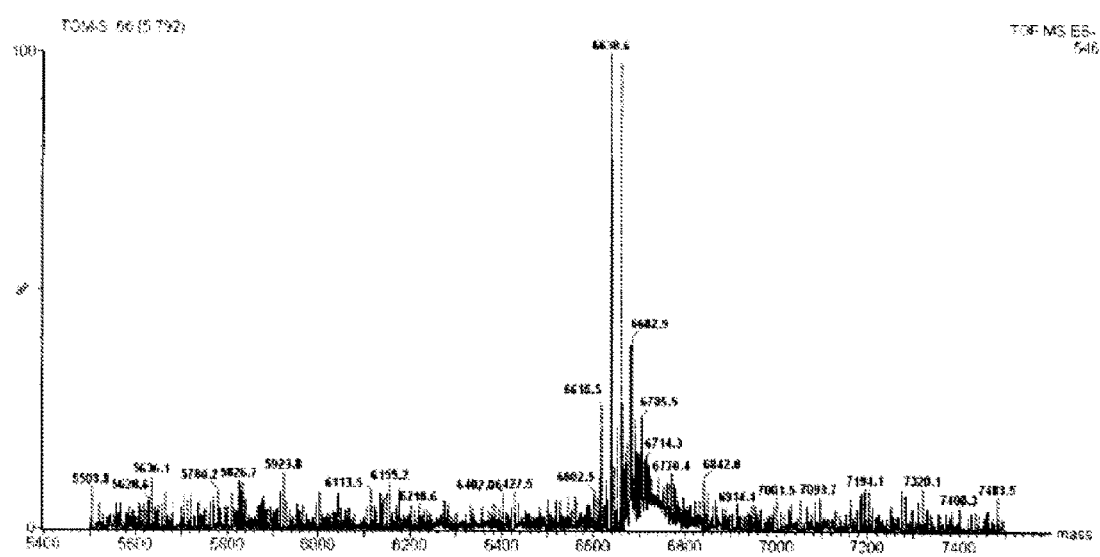
FIG. 6A shows mass spectral data of RNA strands synthesized from 2'-O-TOM.
Figure 6B:
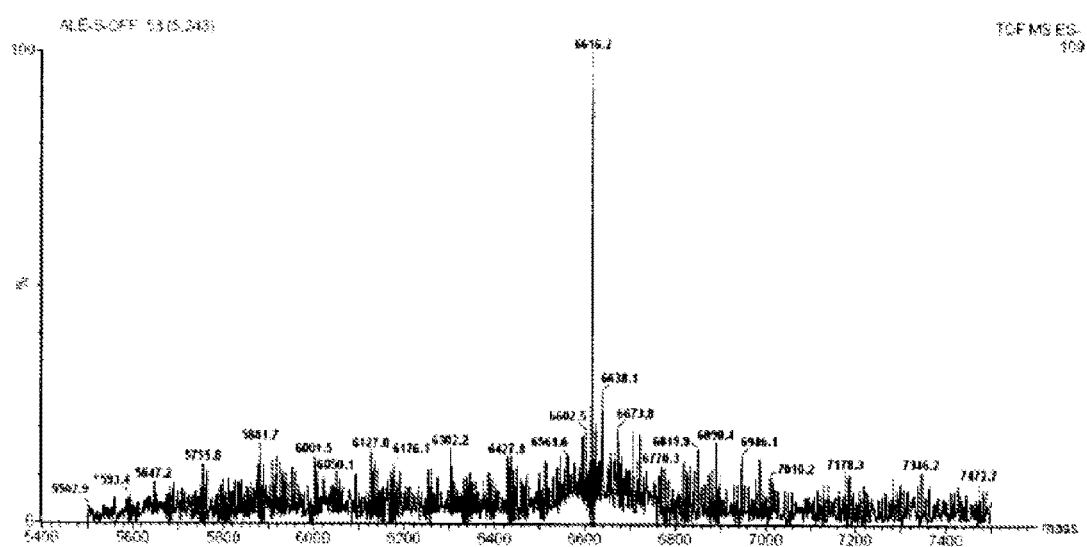
FIG. 6B shows mass spectral data of RNA strands synthesized from 2'-O-TBDMS.
Figure 6C:
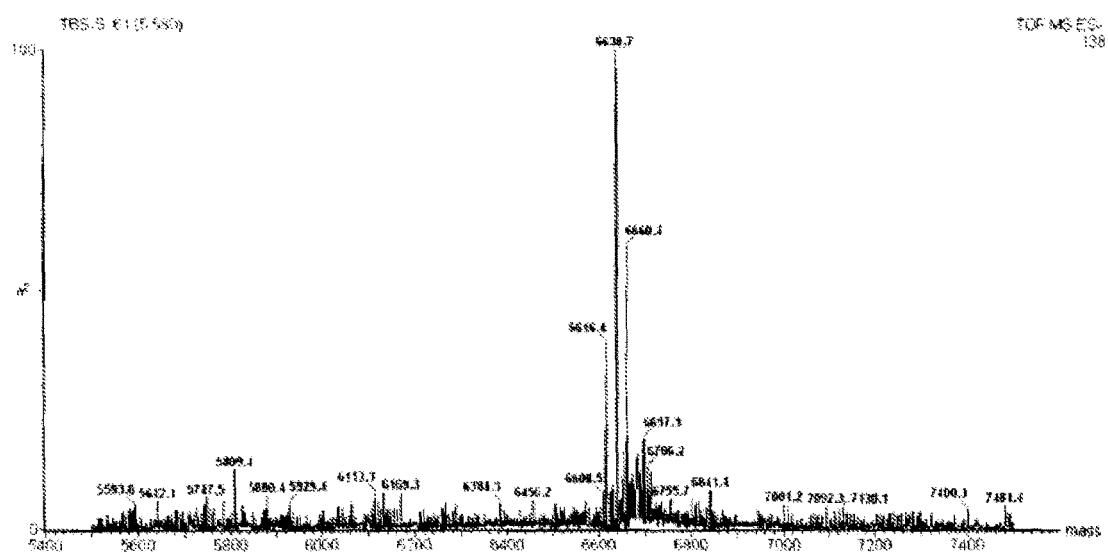
FIG. 6C shows mass spectral data of RNA strands synthesized from 2'-O-ALE.
Figure 6D:
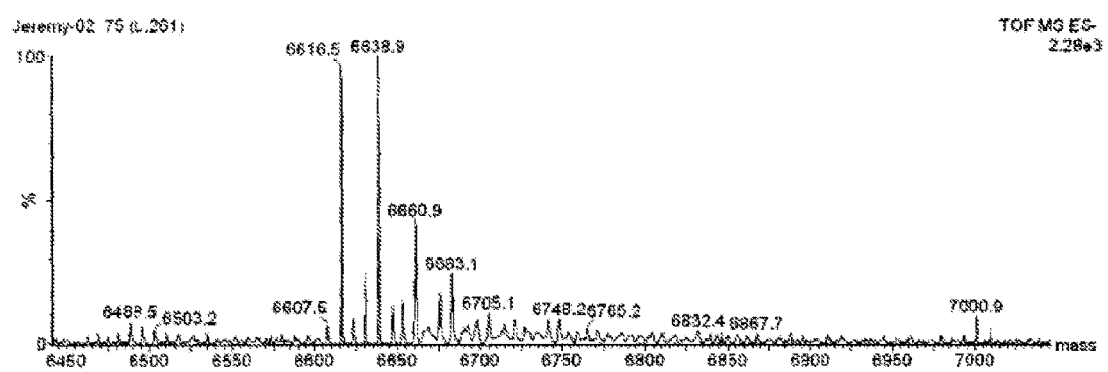
FIG. 6D shows mass spectral data of RNA strands synthesized from 2'-O-ACE monomers.

Coupling data and HPLC profiles obtained for the crude oligomers deprotected under optimum conditions are given in Table 1 and FIG. 5. The quality of the HPLC trace of the ACE oligomer is excellent (purity 81.8%; unknown coupling time), from which an average coupling efficiency of 99% was calculated. At 1 min coupling, average stepwise coupling yield for the 2'-O-ALE monomers, (13a,b,f,h) were higher (97.7%) than those obtained with 2'-O-TOM (96.3%) and 2'-O-TBDMS (94.7%) monomers (Table 2). At longer coupling times (10 min) the values obtained were 98.7, 98.1, and 98.4%, respectively. Careful HPLC and MS analysis of the deprotected oligomers showed in each case that there was no base modification (see Table 6 and FIG. 6 A-D).

TABLE 6

Comparative study of 21-nt RNAs synthesized from various chemistries.[a]

| 2'-O-PG | Found MW[b] | $T_m$ (° C.) | 10 min coupling % purity[c] | Avg. coupling yield[d] | 1 min coupling % purity[c] | Avg. coupling yield[e] |
|---|---|---|---|---|---|---|
| TBDMS | 6616.4 | 59.8 | 70.6 | 98.4 | 45.4 | 96.3 |
| TOM | 6616.5 | 60.1 | 67.2 | 98.1 | 32.0 | 94.7 |
| ACE | 6616.5 | 59.5 | 81.8[f] | 99.0 | n.d. | n.d. |
| ALE | 6616.2 | 59.4 | 76.2 | 98.7 | 61.8 | 97.7 |

[a]Base sequence: r(GCUUGAAGUCUUUAAUUAA)-d(TT);
[b]Calc. molecular weight: 6617 g/mol;
[c]% yield calculated by HPLC (% area of major peak);
[d]Calculated from 10 min. coupling time;
[e]Calculated from 1 min coupling time;
[f]Coupling time unknown.

Figure 7:
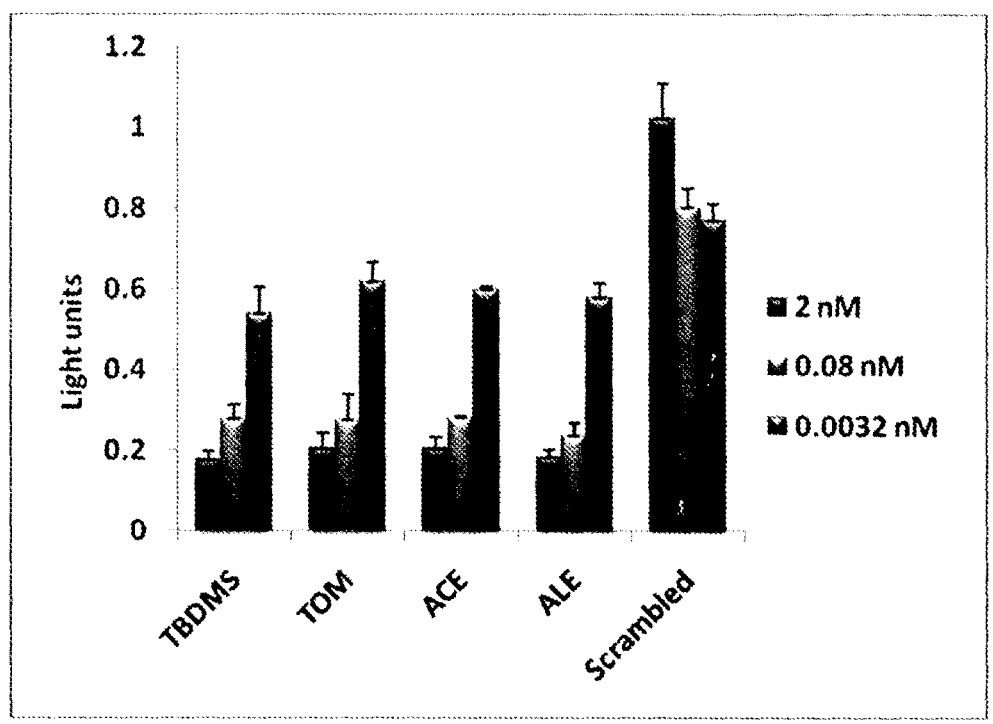
FIG. 7 shows the luciferase gene knockdown by siRNA duplexes (light units are relative to Renilla control). The fully deprotected antisense strands were synthesized by TBDMS, TOM, ACE and ALE chemistries, whereas the complementary sense strand of the siRNA duplex was synthesized by TBDMS chemistry.

As a final check, we evaluated the activity of all RNAs synthesized in an RNAi assay that targets luciferase mRNA (Dowler, T. et al. Nucleic Acids Res 2006, 34, 1669-75). Each of the antisense strands prepared by the various chemistries were allowed to anneal to a common sense strand synthesized via 2'-TBDMS chemistry. As shown in FIG. 7, the siRNA duplex prepared by 2'-O-ALE chemistry had the same gene silencing activity as the siRNA duplexes derived from TBDMS, TOM, and ACE protocols, further confirming the integrity of the synthesized RNA strands.

Synthesis C

In this example, 1 µmol of the sequence 5'-GCU UGA AGU CUU UAA UUA Att-3' (SEQ ID NO: 1) was synthesized on an ABI 3400 using N-FMOC-5'-DMTr-2'-ALE-3'-phosphoramidite monomers 13a, 27-29 and CPG as solid support. The linker attached to the solid support was a light labile tether. Standard oligoribonucleotide synthesis conditions were used with only one minute coupling times and 0.25 M DCI as an activator. Commercially available 2'-TBDMS were also synthesized by standard conditions with one minute coupling times and 0.25 M DCI as an activator for comparison. The 2'-TBDMS oligos were deprotected according to standard protocols. Upon completion of the 2'-ALE RNA synthesis, the material was first treated with 2:3 triethylamine/acetonitrile, 24 hr, followed by treatment with ethylenediamine and ethanol (1:1 v/v) 2 hr, and light (365 nm) for 30 min at r.t. Oligomers were characterized by polyacrylamide gel electrophoresis.

Example 3. Experimental Protocols for the In Situ Light Directed Fabrication of RNA Microarrays General Methods.

All chemicals and solvents were purchased from Sigma-Aldrich including hydrazine hydrate ($NH_2NH_2.H_2O$), triethylamine ($NEt_3$) and acetonitrile (ACN). DNA synthesis reagents were purchased from Glen Research. Cy3-phosphoramidite was also purchased from Glen Research for terminal labeling experiments (0.03 M solution coupling time, 600 s). NPPOC-DNA phosphoramidites used for control experiments and exposure solvent were purchased from Roche NimbleGen. Substrates were prepared by silanizing Superclean glass microscope slides from Arrayit using monohydroxysilane purchased from Gelest Inc. The slides were functionalized with a 2% triethoxysilylpropyl)-4-hydroxybutyramide in 95% EtOH, pH 4-5 (adjusted with glacial acetic acid) for 4 h under agitation. The slides were subsequently washed twice for 20 min in 95% EtOH, pH 4-5 and dried under vacuum at 120° C. for 12 h. After treatment, the slides must be kept in a desiccator for storage.

MAS (Maskless Array Synthesizer) Light Directed Array Synthesis.

Synthesis was carried on a MAS using a Perspective Biosystems Expedite 8909 DNA pump system. The MAS system uses virtual masks generated by computer and imaged by a Texas Instrument's digital light processor (DLP) with dimensions of a 768×1024 array of 13 µm wide micromirrors. An exposure wavelength of 365 nm by a 1000 Hg W lamp (Oriel Instruments, Stratford, Conn.) was used for NPPOC deprotection in Roche NimbleGen. The MAS system used was as described previously (Singh-Gasson et al., 1999, Nature Biotechnology 17: 974-978), with the exception of the RNA monomers being used where appropriate in the synthesis cycle. All phosphoramidites are prepared in the absence of light and diluted under inert atmosphere to prevent moisture contamination. Both DNA and RNA microarrays are prepared with a 3'-$dT_5$ linker on the glass substrate.

DNA Microarrays.

Standard DNA NPPOC-phosphoramidite coupling was conducted at 30 mM concentrations in anhydrous acetonitrile for 60 s with 0.25 M DCI (dicyanoimidazole/ACN) as the activator. Deprotection conditions were optimized for 6 J or 111 s at 54 mW/cm². TAC (tert-butylphenoxyacetyl) anhydride or FastCapA and Cap B (Sigma Aldrich) capping was performed for failed couplings followed by oxidation of the phosphite to the stable phosphate form with 0.02 M solution of aqueous iodine. After completing the stepwise synthesis of the oligomers, a 1:1 solution of ethylenediamine in EtOH for 2 hours was used for base deprotection of standard DNA microarrays, washed with EtOH and dried under Argon (Ar), prior to hybridization experiments.

Coupling Time Optimization-Terminal Labeling.

Figure 8A:
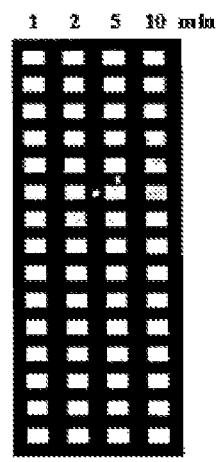
FIG. 8A shows a fluorescence image illustrating the coupling time-Cy3 terminal labeling of rU coupling at 1, 2, 5 and 10 min (lanes 1-4)
Figure 8B:
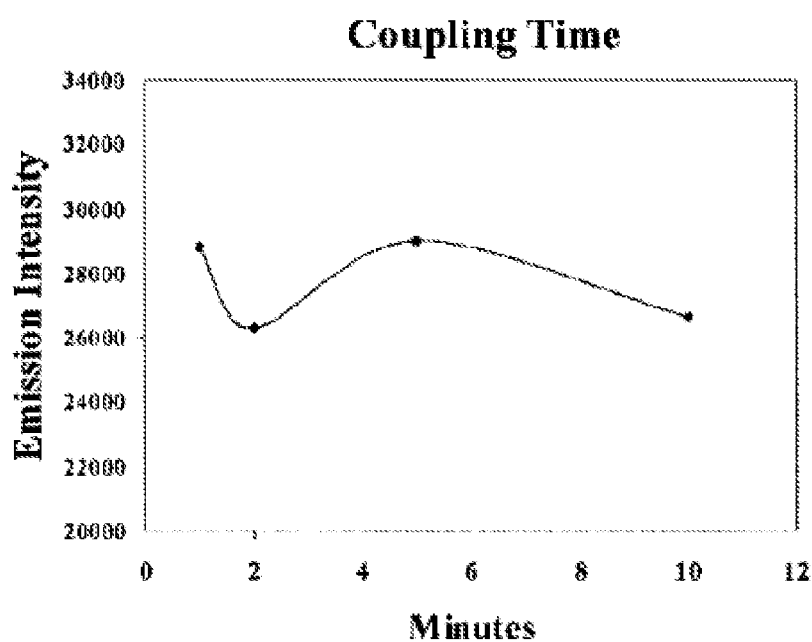

To determine the optimal coupling time, the sequence 3'-d-TTTTT-U10-Ux-Cy3-5' is synthesized, where U10 is a rU 10 mer with 10 min coupling times and Ux is a rU that is coupled at varying times, 1, 2, 5 and 10 min. It is then terminally labeled with Cy3 and evaluated by fluorescence imaging. The scan is shown on the left (FIG. 8A), while the graphical representation (average of all values) is on the right (FIG. 8B). Reactions were conducted at 0.1 M. The emission intensity at each coupling time does not seem to vary significantly. Thus 1 minute coupling times are sufficient for effective coupling of 7.

5'-NPPOC Photodeprotection Analysis

The 5'-NPPOC-2'-ALE RNA 3'-amidite monomers, rA, rC, rG and rU, can be examined to determine the exposure conditions required for 5'-NPPOC deprotection. Arrays can be synthesized with 3'-$dT_5$ linkers followed by coupling of a 5'-NPPOC monomer on silanized slides. Subsequently, the arrays can be subjected to an exposure gradient of UV light, from 0.6J-15J. Following the gradient deprotection, a Cy3-phosphoramidite can be coupled to the terminal position, such that an oligonucleotide in the form 3'-dT5-x-Cy3-5' (x=rA, rC, rG or rU), can be synthesized. The fluorescence intensity of Cy3 on the gradient deprotected array can be quantified to determine the optimal deprotection conditions of each base.

In this example, an exposure gradient of 0-15 J (or 0-250 s, 55 mW/cm$^2$ time of exposure) for the NPPOC deprotection was performed. Each rU monomer coupling was conducted at 10 minute coupling times and 0.1 M phosphoramidite concentration. A rU 20 mer was synthesized where a 0-15 J exposure gradient was employed at each n+1 5'NPPOC deprotection.

Figure 9A:
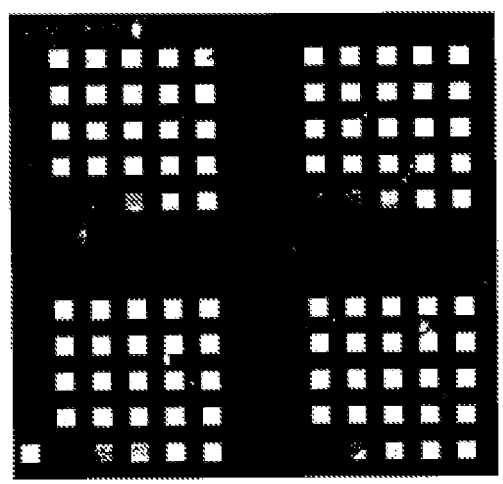
FIG. 9A shows an image illustrating the exposure gradient of $rU_{20}$, 0-15 J of a Cy5 emission scan of $rU_{20}$:$dA_{20}$-Cy5.
Figure 9B:
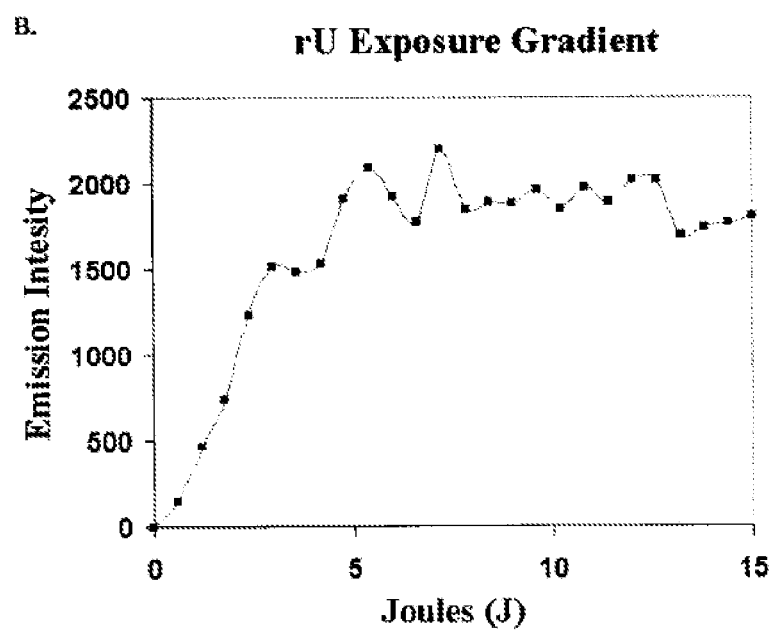
FIG. 9B shows a graphical representation of the exposure gradient.

FIG. 9 shows an image (A) and a graph (B) illustrating the exposure gradient of $rU_{20}$, O-15 J. FIG. 9A, Cy5 emission scan of $rU_{20}$:$dA_{20}$-Cy5. FIG. 9B, Graphical representation of exposure gradient. FIG. 9A shows the hybridization fluorescence scan of a rU-20 mer hybridized to a $dA_{20}$-Cy5. Each quadrant represents the same experiment. Lower left feature of each quadrant (darkest or lowest emission intensity) is 0.6 J of energy followed by an incremental increase in energy by 0.6 J from left to right up to the 25th feature which is 15 J. An average emission intensity profile of the four quadrants is shown in the graphical representation of FIG. 9B. The results indicate that the optimal exposure of the rU NPPOC protecting group occurs at approximately 6.5-7 J. This is similar to the standard deprotection for NPPOC-DNA monomers which is approximately 6 J (data not shown).

Optimization of rU Phosphoramidite (14a) Concentration.

An exposure gradient of O-15 J on a rU 20 mer was performed using 1 minute phosphoramidite coupling times, since coupling time efficiency was evaluated and determined to be optimal under these conditions. However to assess the optimal concentration, the experiment was conducted using 30 mM rU amidite solution instead. The exposure gradient experimental procedure was as described above.

Figure 10A:
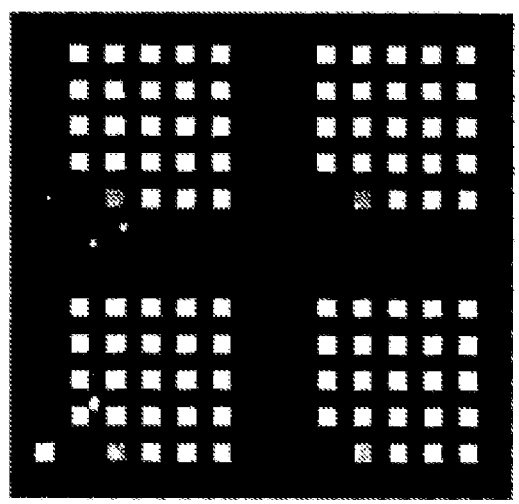
FIG. 10A shows an image illustrating the exposure gradient of $rU_{20}$, 0-15 J. rU coupling time, 1 min at 30 mM concentration of a Cy5 emission scan of $rU_{20}$: $dA_{20}$-Cy5.
Figure 10B:
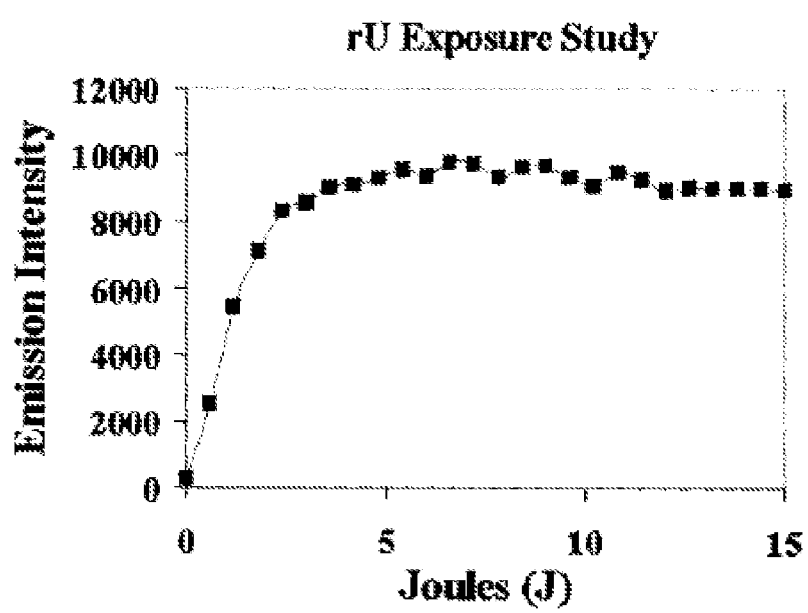
FIG. 10B shows a graphical representation of the exposure gradient.

FIG. 10 shows an image (A) and a graph (B) illustrating the exposure gradient of $rU_{20}$. O-15 J. rU coupling time, 1 min at 30 mM concentration. FIG. 10A, Cy5 emission scan of $rU_{20}$: $dA_{20}$-Cy5. FIG. 10B, Graphical representation of exposure gradient.

The emission intensity values, shown in FIG. 10B, demonstrate sufficient NPPOC photodeprotection at 6.5 J. The emission intensity values are excellent and comparable to that of a DNA exposure gradient control ($dA_{20}$:$dT_{20}$,—data not shown).

In conclusion, the rU NPPOC phosphoramidite shows remarkable similarity to DNA NPPOC phosphoramidites. Reactions conditions require 1 min coupling time, 30 mM concentration and 6.5 J photodeprotection.

Dynamic Range and Sensitivity.

An array consisting of 5 random mixed oligonucleotides can be synthesized (Table 7). Five (5) complementary labeled probes can be hybridized to the array in a range of concentrations from 1 pM to 300 pM. Each oligonucleotide can be repeated 20 times on the array surface. The fluorescence intensity measured following hybridization can be averaged over the 20 features for each oligonucleotide. To determine the relative sensitivity, arrays containing oligonucleotides of the sequences below, can be prepared with DNA NPPOC monomers as a control. The objective of this experiment is to quantify the sensitivity of probe hybridization based on the dynamic range of concentration.

TABLE 7

| Oligonucleotides |
|---|
| Chip Sequences |
| SEQ ID NO: 2 | 5'-CCUGUGCGUUACAGCUACGU-3' |
| SEQ ID NO: 3 | 5'-GGCAGUCUGAAGUUAGUAUA-3' |
| SEQ ID NO: 4 | 5'-CCACUUCAUUUCCUAACAGC-3' |
| SEQ ID NO: 5 | 5'-UACAAGAUUACAAUAUGUGG-3' |
| SEQ ID NO: 6 | 5'-AGCCACGUCUUCAUGGAGGA-3' |
| Complementary Probes |
| SEQ ID NO: 7 | 5'-Cy5-ACGTAGCTGTAACGCACAGG-3' |
| SEQ ID NO: 8 | 5'-Cy5-TATACTAACTICAGACTGCC-3' |
| SEQ ID NO: 9 | 5'-Cy5-GCTGTTAGGAAATGAAGTGG-3' |
| SEQ ID NO: 10 | 5'-Cy5-CCACATATrGTAATCTIGTA-3' |
| SEQ ID NO: 11 | 5'-Cy5-TCCTCCATGAAGACGTGGCT-3' |

RNA Microarrays.

5'-NPPOC-modified phosphoramidites 14a, 14b, 14f and 14h were employed in the synthesis of RNA microarrays. Synthesis was carried on the maskless array synthesizer (MAS) described above with glass substrates ('chips') mounted on a flow cell connected to a DNA synthesizer. To determine the coupling efficiency of the RNA monomers, sequences of one to twelve nucleotides in length were synthesized onto chips and terminally labeled with a Cy3 phosphoramidite. $dT_5$ linker strands made with 5'-O—NPPOC-modified thymine phosphoramidites were used to distance the RNA strand from the chip surface. All the monomers (0.05 to 0.06 M in ACN) were activated with 4,5-dicyanoimidazole (DCI; 0.25M in ACN) and allowed to couple to the support for 10 to 15 minutes. Standard capping ($Ac_2O$) was performed followed by oxidation (0.02M $I_2$/water/pyridine). UV light energy dose of 6.5 J/cm$^2$ at 365 nm was required for a complete exposure of the photolabile 5'-O—NPPOC group (FIGS. 9, 10). Fluorescence intensities from the coupling steps were fit with a single exponential decay to determine average coupling efficiency. Coupling parameters and efficiencies for the four monomers are given in Table 8.

TABLE 8

Microarray synthesis coupling parameters and efficiencies.

| Monomer | Concentration (mM) | Coupling time (min.) | Coupling efficiency (%) |
|---|---|---|---|
| rA, 14f | 50 | 10 | 86 |
| rC, 14b | 50 | 10 | 95 |
| rG, 14h | 60 | 15 | 96 |
| rU, 14a | 50 | 10 | 97 |

Following the determination of coupling efficiencies, two microarrays ($rU_{12}$ and $rA_{12}$), were deprotected. Decyanoethylation was first conducted by immersing the synthesized microarrays in 2:3 $NEt_3$/ACN, 80 min with agitation at room temperature. The slides were rinsed five times in anhydrous ACN and dried under Ar. The 2'-O-ALE protecting groups are removed by treatment with 0.5 M $NH_2NH_2.H_2O$ (3:2 v/v pyr:AcOH), shaken for 1 h at r.t. The slides were washed with 1:1 pyr:AcOH (pH>5) to remove any salts formed on the glass substrate. DNA control experiments ($dA_{10}$:$dT_{10}$ microarray hybridizations) were conducted prior to RNA microarray synthesis to ensure compatibility with deprotection conditions required for RNA (data not shown). Hybridization results indicated no loss in oligonucleotide from the glass substrate when DNA microarrays were exposed to the reagents that remove phosphate and 2'-hydroxyl protecting groups. Following deprotection, the oligonucleotides on the chip were hybridized with either Cy5-labeled $dA_{20}$ or Cy5-labeled $dT_{20}$ (FIG. 11).

Figure 11:
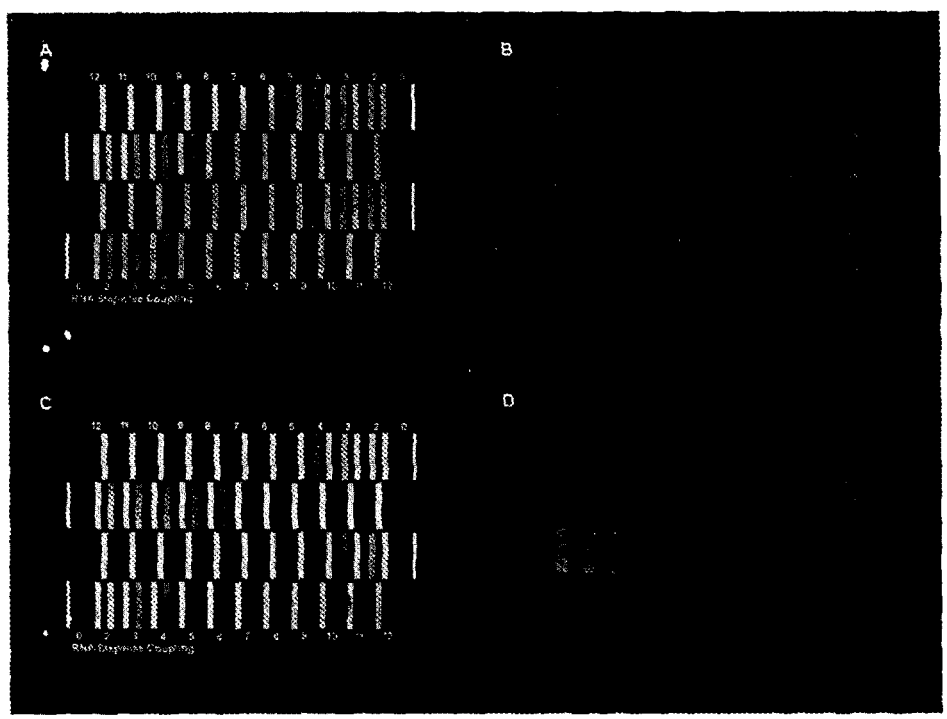
FIG. 11 demonstrates coupling and hybridization of rU and rA microarrays. A. Coupling efficiency microarray for rU with zero (blank) through twelve coupling steps and 5'-terminal Cy3 label. Each coupling step feature includes an adjacent area with the same number of couplings but no terminal label, as well as a one coupling reference. Intensity data was fit with a single exponential to obtain the average coupling efficiency for rU in Table 8. B. The same microarray in A, hybridized with Cy5-labeled $dA_{20}$. C. Equivalent microarray with rA couplings. D. rA chip hybridized with Cy5-labeled $dT_{20}$.

The microarray features shown in the fluorescence micrographs shown in FIG. 11 are arranged in such a way that the length of the oligomers increases progressively (n=0 to 12), that is, the sequences on the chip above or below a numbered label n are: (surface)-$dT_5$-$r_n$, where n is between 0 and 12. Zero coupling means that the area was subject to a complete coupling cycle, but without monomer, and shows that capping on the chip is ~90% efficient. The chip surface corresponding to each "n" labeled coupling step is subdivided into four sections: (1) single RNA coupling ($dT_5$-rN) is followed by (2) a very bright, single terminally-labeled RNA coupling ($dT_5$-rN-Cy3), followed by (3) $dT_5$-$rN_n$ and (4) $dT_5$-$rN_n$-Cy3. The unlabeled regions are used for background subtraction of the fluorescence signal. The numbers and label on the chip have the terminally-labeled, single RNA coupling pattern ($dT_5$-rN-Cy3). Both the terminally labeled and unlabeled n-mers are visible upon hybridization with the probes (Cy5-labeled $dA_{20}$ or Cy5-labeled $dT_{20}$), the longer (and more stable) duplexes provide, as expected, the brightest signal, which gradually decreases as the length of probes decreases.

In the examples of hybridization experiments described above, precautions were taken to ensure an RNase free environment to prevent enzymatic degradation of the RNA microarrays. DPC (diethylpyrocarbonate, Sigma Aldrich) autoclaved $H_2O$ was used in preparation of the hybridization buffer. A TRIS buffer consisting of 40 mM TRIS-HCl, 10 mM $MgCl_2$, pH 7.2 was used in both DNA and RNA hybridization experiments. Hybridizations were performed using adhesive coverslips (GraceBiolabs). A 300 µL solution of 500 nM DNA probes (e.g., $dA_{10}$-5'-Cy5 and $dA_{20}$-5'-Cy5) were hybridized to the respective rU complements. Hybridizations were conducted for 1 h at 4° C. for $rU_{10}$:$dA_{10}$ and ambient temperature for $rU_{20}$:$dA_{20}$. The slides were washed with 300 µL of cold nonstringent (NS) wash buffer (0.5 M NaCl, 0.03 M Phosphate, 0.3 mM EDTA, 0.01% Tween-20) prior to fluorescence scanning. The hybridized chips were scanned and analyzed on an Applied Precision ArrayWorx Biochip reader.

Example 4. Ribonuclease a Substrate RNA Microarray

RNA degradation is an important process as demonstrated by the multiple classes of RNases present in many organisms. In addition to providing a defense against viral RNA, RNases function within the cell to degrade coding or non-coding RNA once these have served their purpose. A biological assay was conducted to demonstrate the value of using RNA microarrays for studying enzyme kinetics and specificity on ribonuclease substrate libraries.

Ribonuclease a Substrate Sequences.

The RNase A family of endoribonucleases cleave optimally after the pyrimidine in sequences of the form pyrimidine-purine-purine. Following this scheme, the enzymatic cleavage activity of RNase A has been measured for several substrates (Kelemen et al, 1999, Nucleic Acids Research, 27, 3696-3701). Table 9 lists the sequences that were chosen from Kelemen et al for the RNase substrate RNA microarray, along with the reference substrate and activity thereof. The primary difference between the microarray and references substrates is the fluorescence detection scheme, which in the case of the microarray is based on a loss of fluorescence from Cy3 following cleavage by RNase, while for the reference substrates, cleavage leads to increased fluorescence from 6-FAM due to separation from a quenching chromophore. In addition, the microarray sequences are tethered to the glass surface with a thymine 15mer. Like the reference substrates, the microarray sequences consist of both RNA and DNA nucleotides, and therefore serves also as a test for the synthesis and deprotection of microarrays containing DNA/RNA chimeric sequences.

TABLE 9

Sequences in RNase A substrate microarray

| Sequence name | Microarray sequence 3' to 5' | Reference substrate 5' to 3' | Reference activity $k_{cat}/K_m$ ($10^7$ $M^{-1}s^{-1}$) |
| --- | --- | --- | --- |
| A | $T_{15}$-dArU-Cy3 | 6-FAM-rUdA-6-TAMRA | 2.5 ± 0.3 |
| B | $T_{15}$-$(dA_2)$rUdA-Cy3 | 6-FAM-dArU$(dA_2)$-6-TAMRA | 3.6 ± 0.4 |
| C | $T_{15}$-$(dA_3)$rU$(dA)_2$-Cy3 | 6-FAM-$(dA)_2$rU$(dA_3)$-6-TAMRA | 4.7 ± 0.6 |
| D | $T_{15}$-$(dA_4)$rU$(dA)_3$-Cy3 | 6-FAM-$(dA)_3$rU$(dA_4)$-6-TAMRA | 4.8 ± 0.5 |

Ribonuclease a Substrate Microarray Synthesis and Deprotection.

The synthesis of this microarray was conducted with uracil NPPOC RNA phosphoramidite along with thymine and adenine NPPOC DNA phosphoramidites. Thymine is used for the 15mer tether as well as a substitute for uracil for four control sequences that are synthesized adjacent to the four RNase substrates listed in Table 9. Following synthesis, RNase substrate microarrays were deprotected in one of two ways. One method was to first deprotect the DNA bases with 1:1 (v/v) ethylenediamine-ethanol for 4 hours, followed by deprotection of the uracil with 2:3 (v/v) triethylamine-acetonitrile (100 min) then 0.5 M hydrazine hydrate in 3:2 (v/v) pyridine-acetic acid (100 min). The second method was to remove all protecting groups with the ethylenediamine-ethanol solution for 4 hours. Both methods lead to microarrays with the same sensitivity to RNase A.

Enzyme Kinetics on the Microarray.

Figure 12:
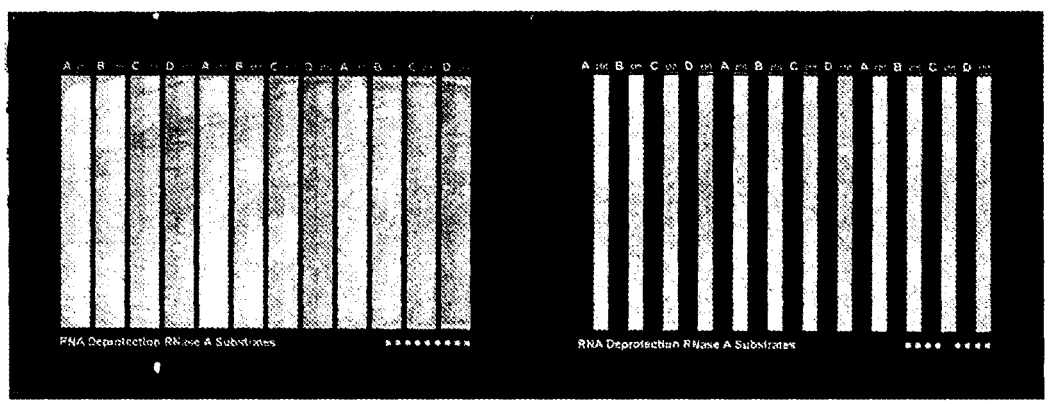
FIG. 12 shows a scanner image of the RNase A substrate microarray before (left) and after exposure to RNase A. Each RNase A substrate is labeled according to the scheme in Table 10 and is adjacent to a control substrate with thymine replacing uracil in the nucleotide sequence.
Figure 13:
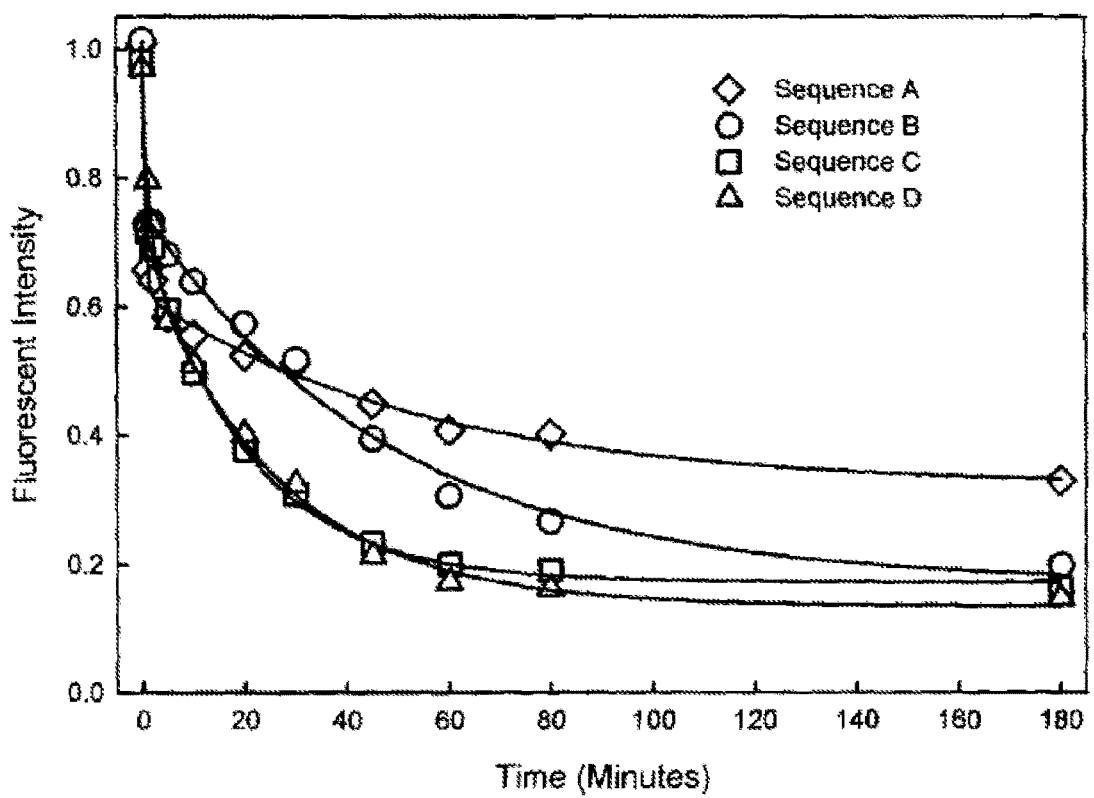
FIG. 13 shows a plot of fluorescent emission intensity from the four RNase A substrates in Table 10, normalized to the control DNA sequences, at various intervals following exposure to a dilute RNase A solution.

Following deprotection, the microarray was immersed in a 50 ml Falcon tube containing 40 ml of 100 nM RNase A in 0.1 M 2-(N-morpholino)ethanesulfonic acid (MES) buffer. The tube was gently mechanically agitated for 1 min and then the microarray was quickly removed and washed in water and immediately dried with Argon. The microarray was then scanned with a GenePix 4000B microarray scanner. This procedure was repeated multiple time with various immersion times in the RNase solution. FIG. 12 shows the initial and terminal scans. The fluorescent data from the scans was then extracted using the GenePix Pro software. The plotted data for all four RNase substrates is shown in FIG. 13, which shows fluorescent intensity from the substrate sequences (normalized to the fluorescent intensity from the corresponding control sequences) as a function of exposure time to the RNase A. FIG. 13 demonstrates that that RNase A acts effectively on RNA microarray substrates with kinetics comparable to those of the reference substrates. The results also indicate that mixed RNA/DNA microarrays have compatible synthesis and deprotection schemes.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of bioengineering, molecular biology, molecular interactions, chemistry, biology, medicine, and medical diagnostics, are within the scope of this invention. All publications, patents, and patent applications cited herein are incorporated by reference in their entirety for all purposes.

What is claimed is:

1. A method of synthesizing an oligoribonucleotide on a solid substrate, the method comprising:

a) immobilizing on the solid substrate a first ribonucleotide monomer comprising the compound of formula (I) to create an immobilized ribonucleotide monomer;

b) removing a protecting group so as to create a deprotected immobilized ribonucleotide monomer;

c) contacting the deprotected immobilized ribonucleotide monomer with a second ribonucleotide monomer comprising the compound of formula (I), under conditions such that the second ribonucleotide monomer couples with the deprotected immobilized ribonucleotide monomer to produce, in situ, the oligoribonucleotide on the solid substrate,
wherein the compound of formula (I) is:

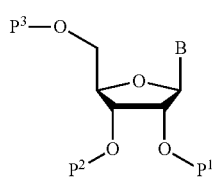

(I)

wherein
B is a member selected from the group consisting of 6-amino-9H-purin-9-yl, 2-amino-1H-purin-6(9H)-on-9-yl, 4-aminopyrimidin-2(1H)-on-1-yl, pyrimidine-2,4(1H,3H)-dion-1-yl, N4-levulinylcytosine, N2-levulinylguanine, N2-(dimethylformamidine)guanine, N2-phenoxyacetylguanine, N6-(tert-butylphenoxyacetyl)adenine, N6-(9-fluorenylmethoxycarbonyl)adenine, N2-(9-fluorenylmethoxycarbonyl)guanine, N4-benzoylcytosine, N6-benzoyladenine, N4-isobutyrylcytosine, N4-acetylcytosine, and N2-isobutyrylguanine;
$P^1$ is hydrogen or —CH$_2$OC(O)CH$_2$CH$_2$C(O)CH$_3$;
$P^2$ is hydrogen or

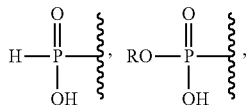

or salts thereof, wherein R is methyl, 2-cyanoethyl, 2-chlorophenyl, or 4-chlorophenyl;
or

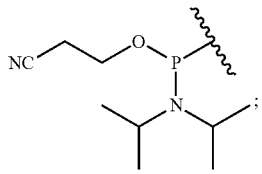 [SMILES: *P(OCCC#N)N(C(C)C)C(C)C]

$P^3$ is hydrogen or an O-protecting group, which is a member selected from the group consisting of:
a. a base labile group selected from —CH$_2$OC(O)CH$_2$CH$_2$C(O)CH$_3$ and —C(O)CH$_2$CH$_2$C(O)CH$_3$;
b. an acid labile group selected from 1-(2-fluorophenyl)-4-methoxypiperidin-4-yl, 1-(4-chlorophenyl)-4-ethoxypiperidin-4-yl, 4-(N-dichloroacetyl-N-methylamino)benzyloxymethyl, dimethoxytrityl and monomethoxytrityl;
c. a reduction labile group selected from 2-tert-butyldithiomethyl and allyl;
d. a fluoride labile group selected from tert-butyldimethylsilane, 2'-O-triisopropylsilyloxymethyl, cyanoethylmethyl, and 2-(4-tolylsulfonyl)ethoxymethyl; and
e. a photolabile group selected from 2-(2-nitrophenyl)propoxycarbonyl, α-methylnitorpiperonyloxycarbonyl, and 5'-O-dimethoxybenzoincarbonate; and
wherein at least one of $P^1$ and $P^3$ is —CH$_2$OC(O)CH$_2$CH$_2$C(O)CH$_3$ as the O-protecting group.

2. The method of claim 1, wherein the first ribonucleotide monomer has a 2'-O-acetal levulinyl ester protecting group and a 5'-2-(2-nitrophenyl)propoxycarbonyl protecting group and the immobilized ribonucleotide monomer is irradiated to remove the 5'-2-(2-nitrophenyl)propoxycarbonyl protecting group.

3. The method of claim 1, wherein the immobilized ribonucleotide monomer is irradiated with light.

4. The method of claim 1, wherein the first ribonucleotide monomer is immobilized to the solid substrate via a linker.

* * * * *

UNITED STATES PATENT AND TRADEMARK OFFICE
CERTIFICATE OF CORRECTION

PATENT NO. : 10,287,313 B2
APPLICATION NO. : 14/983504
DATED : May 14, 2019
INVENTOR(S) : Masad Damha et al.

Page 1 of 1

It is certified that error appears in the above-identified patent and that said Letters Patent is hereby corrected as shown below:

In the Specification

Column 1, Lines 18-21:
Delete the phrase:
"This invention was made with United States government support under grant No. HG002375 awarded by the NIH. The United States government has certain rights in this invention."

And replace with:
--This invention was made with government support under HG003275, GM031892 and GM050942 awarded by the National Institutes of Health. The government has certain rights in the invention.--.

Signed and Sealed this
Twenty-second Day of December, 2020

Andrei Iancu
*Director of the United States Patent and Trademark Office*

```
                         SEQUENCE LISTING

<160> NUMBER OF SEQ ID NOS: 11

<210> SEQ ID NO 1
    <211> LENGTH: 21
    <212> TYPE: DNA
    <213> ORGANISM: Artificial Sequence
    <220> FEATURE:
    <223> OTHER INFORMATION: combined DNA/RNA, bases 1-19 RNA, bases 20,
          21 DNA

<400> SEQUENCE: 1
gcuugaaguc uuuaauuaat t                                                  21

<210> SEQ ID NO 2
    <211> LENGTH: 20
    <212> TYPE: RNA
    <213> ORGANISM: Artificial Sequence
    <220> FEATURE:
    <223> OTHER INFORMATION: Chip Sequence

<400> SEQUENCE: 2
ccugugcguu acagcuacgu                                                    20

<210> SEQ ID NO 3
    <211> LENGTH: 20
    <212> TYPE: RNA
    <213> ORGANISM: Artificial Sequence
    <220> FEATURE:
    <223> OTHER INFORMATION: Chip Sequence

<400> SEQUENCE: 3
ggcagucuga aguuaguaua                                                    20

<210> SEQ ID NO 4
    <211> LENGTH: 20
    <212> TYPE: RNA
    <213> ORGANISM: Artificial Sequence
    <220> FEATURE:
    <223> OTHER INFORMATION: Chip Sequence

<400> SEQUENCE: 4
ccacuucauu uccuaacagc                                                    20

<210> SEQ ID NO 5
    <211> LENGTH: 20
    <212> TYPE: RNA
    <213> ORGANISM: Artificial Sequence
    <220> FEATURE:
    <223> OTHER INFORMATION: Chip Sequence

<400> SEQUENCE: 5
uacaagauua caauaugugg                                                    20

<210> SEQ ID NO 6
```

```
<211> LENGTH: 20
<212> TYPE: RNA
<213> ORGANISM: Artificial Sequence
<220> FEATURE:
<223> OTHER INFORMATION: Chip Sequence

<400> SEQUENCE: 6
agccacgucu ucauggagga                                               20

<210> SEQ ID NO 7
<211> LENGTH: 20
<212> TYPE: DNA
<213> ORGANISM: Artificial Sequence
<220> FEATURE:
<223> OTHER INFORMATION: Probe

<400> SEQUENCE: 7
acgtagctgt aacgcacagg                                               20

<210> SEQ ID NO 8
<211> LENGTH: 20
<212> TYPE: DNA
<213> ORGANISM: Artificial Sequence
<220> FEATURE:
<223> OTHER INFORMATION: Probe

<400> SEQUENCE: 8
tatactaact tcagactgcc                                               20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
gctgttagga aatgaagtgg                                               20

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
ccacatattg taatcttgta                                               20

<210> SEQ ID NO 11
<211> LENGTH: 20
<212> TYPE: DNA
<213> ORGANISM: Artificial Sequence
<220> FEATURE:
<223> OTHER INFORMATION: Probe

<400> SEQUENCE: 11
tcctccatga agacgtggct                                               20
```